US006136550A

United States Patent [19]
Heinemann et al.

[11] Patent Number: 6,136,550
[45] Date of Patent: Oct. 24, 2000

[54] NEURONAL NICOTINIC ACETYLCHOLIHNE RECEPTOR COMPOSITIONS

[75] Inventors: Stephen Fox Heinemann, La Jolla, Calif.; James Warner Patrick, Houston, Tex.; James Richard Boulter, San Diego, Calif.; Evan Samuel Deneris, La Jolla, Calif.; Keiji Wada, Rockville, Md.; Marc Charles Ballivet, Geneva, Switzerland; Daniel Jay Goldman, Ann Arbor, Mich.; John Gerard Connolly; Robert Michael Duvoisin, both of Del Mar, Calif.; Eden Deer Heinemann, San Luis Obispo, Calif.

[73] Assignee: The Salk Institute for Biological Studies

[21] Appl. No.: 08/349,956

[22] Filed: Dec. 6, 1994

Related U.S. Application Data

[62] Division of application No. 07/898,185, Jun. 12, 1992, Pat. No. 5,371,188, which is a continuation of application No. 07/321,384, Mar. 14, 1989, abandoned, which is a continuation-in-part of application No. 07/170,295, Mar. 18, 1988, abandoned.

[51] Int. Cl.$^7$ .......................... G01N 33/566; C12N 15/12
[52] U.S. Cl. ................... 435/7.21; 435/69.1; 435/252.3; 435/320.1; 436/501; 536/23.5
[58] Field of Search ................ 435/69.1, 252.3, 435/320.1, 7.1, 7.21; 536/23.5; 436/501

[56] References Cited

U.S. PATENT DOCUMENTS 4,518,527   5/1985   Numa ..................................... 530/327

OTHER PUBLICATIONS

Mishina et al. "Expression of Functional Acetylcholine receptor . . . ". Nature 307:604–608, Feb. 1984.
Whiting et al. Proc. Natl. Acad. Sci. USA 84:595–599, Jan. 1987.
Boulter et al. "Isolation of a cDNA clone coding fpr a possible neural nicotinic acetylcholine receptor alpha––subunit", Nature 319:368–374, Jan. 1986.
Goldman et al. "Members of a Nicotine Acetylcholine receptor gene family . . . ". Cell 48:204–213, Mar. 1987.
Whiting et al. "Functional acetylcholine receptor in PC12 cells . . . ". Nature 327:515–518, Jun. 1987.
Whiting et al. "Affinity Labeling of Neuronal acetylcholine receptors . . . ". FEBS Letters 23(1):55–60, Feb. 1984.

*Primary Examiner*—John Ulm
*Attorney, Agent, or Firm*—Gray Cary Ware & Freidenrich; Stephen E. Reiter, Esq.

[57] ABSTRACT

The present invention relates to a family of neuronal nicotinic acetylcholine receptors comprised of neuronal agonist and non-agonist binding subunits, and DNA sequences encoding such subunits. These novel neuronal nicotinic acetylcholine receptor subunits include the agonist binding subunits alpha2, alpha3, alpha4, and alpha5, plus non-agonist binding subunits beta2, beta3 and beta4. Representative cDNA clones that contain the DNA sequences of the invention have been deposited with the American Type Culture Collection for patent purposes.

21 Claims, 49 Drawing Sheets

```
                10                        30                              50
GGC ACC GGG GCG CCG CCG CCG CTG CTG CTA CTG CCG CTG CTG CTG CTC CTA GGG ACC GGC
Gly Thr Gly Ala Pro Pro Pro Leu Leu Leu Leu Pro Leu Leu Leu Leu Leu Gly Thr Gly
            70                        90                             110
CTC TTG CCT GCT AGC AGC CAC ATA GAG ACC CGG GCC CAT GCG GAG GAG CGG CTC CTG AAG
Leu Leu Pro Ala Ser Ser His Ile Glu Thr Arg Ala His Ala Glu Glu Arg Leu Leu Lys
            130                       150                            170
AGA CTC TTC TCC GGT TAC AAC AAG TGG TCT CGG CCA GTA GGC AAT ATC TCA GAT GTG GTC
Arg Leu Phe Ser Gly Tyr Asn Lys Trp Ser Arg Pro Val Gly Asn Ile Ser Asp Val Val
            190                       210                            230
CTC GTC CGC TTT GGC TTG TCC ATT GCT CAG CTC ATT GAC GTG GAC GAG AAG AAC CAG ATG
Leu Val Arg Phe Gly Leu Ser Ile Ala Gln Leu Ile Asp Val Asp Glu Lys Asn Gln Met
            250                       270                            290
ATG ACA ACC AAC GTG TGG GTG AAG CAG GAG TGG CAC GAC TAC AAG CTG CGC TGG GAC CCT
Met Thr Thr Asn Val Trp Val Lys Gln Glu Trp His Asp Tyr Lys Leu Arg Trp Asp Pro
            310                       330                            350
GGT GAC TAC GAG AAT GTC ACC TCC ATC CGC ATC CCC TCT GAA CTC ATC TGG AGG CCT GAC
Gly Asp Tyr Glu Asn Val Thr Ser Ile Arg Ile Pro Ser Glu Leu Ile Trp Arg Pro Asp
            370                       390                            410
ATC GTC CTC TAC AAC AAT GCG GAT GGA GAC TTT GCA GTC ACC CAC CTG ACC AAG GCC CAC
Ile Val Leu Tyr Asn Asn Ala Asp Gly Asp Phe Ala Val Thr His Leu Thr Lys Ala His
            430                       450                            470
CTG TTC TAT GAC GGA AGG GTG CAG TGG ACA CCC CCA GCC ATC TAT AAG AGC TCC TGC AGC
Leu Phe Tyr Asp Gly Arg Val Gln Trp Thr Pro Pro Ala Ile Tyr Lys Ser Ser Cys Ser
            490                       510                            530
ATC GAC GTC ACC TTC TTC CCC TTT GAC CAG CAG AAC TGT ACC ATG AAG TTT GGA TCC TGG
Ile Asp Val Thr Phe Phe Pro Phe Asp Gln Gln Asn Cys Thr Met Lys Phe Gly Ser Trp
            550                       570                            590
ACC TAC GAC AAG GCC AAG ATT GAC TTA GTG AGC ATT CAT AGC CGT GTG GAC CAA CTG GAC
Thr Tyr Asp Lys Ala Lys Ile Asp Leu Val Ser Ile His Ser Arg Val Asp Gln Leu Asp
            610                       630                            650
TTC TGG GAA AGT GGG GAG TGG GTC ATC GTG GAT GCT GTG GGC ACC TAC AAC ACC AGG AAG
Phe Trp Glu Ser Gly Glu Trp Val Ile Val Asp Ala Val Gly Thr Tyr Asn Thr Arg Lys
            670                       690                            710
TAC GAG TGC TGT GCC GAG ATC TAT CCT GAC ATC ACC TAT GCC TTC ATC ATC CGA CGC CTG
Tyr Glu Cys Cys Ala Glu Ile Tyr Pro Asp Ile Thr Tyr Ala Phe Ile Ile Arg Arg Leu
            730                       750                            770
CCG CTA TTC TAC ACC ATC AAC CTC ATC ATC CCG TGC CTG CTC ATC TCC TGT CTC ACC GTG
Pro Leu Phe Tyr Thr Ile Asn Leu Ile Ile Pro Cys Leu Leu Ile Ser Cys Leu Thr Val
```

FIG. 2A

```
              790                    810                       830
CTG GTC TTC TAT CTG CCT TCA GAG TGT GGC GAG AAG GTC ACA CTG TGC ATC TCG GTG CTG
Leu Val Phe Tyr Leu Pro Ser Glu Cys Gly Glu Lys Val Thr Leu Cys Ile Ser Val Leu
              850                    870                       890
CTT TCT CTC ACC GTC TTC CTG CTG CTC ATC ACC GAG ATC ATC CCG TCC ACC TCG CTG GTC
Leu Ser Leu Thr Val Phe Leu Leu Leu Ile Thr Glu Ile Ile Pro Ser Thr Ser Leu Val
              910                    930                       950
ATC CCG CTC ATC GGC GAG TAC CTC CTC TTC ACC ATG ATC TTC GTC ACC CTC TCC ATC GTC
Ile Pro Leu Ile Gly Glu Tyr Leu Leu Phe Thr Met Ile Phe Val Thr Leu Ser Ile Val
              970                    990                       1010
ATC ACG GTC TTC GTG CTC AAT GTG CAC CAC CGC TCG CCA CGC ACA CAC ACG ATG CCC GCC
Ile Thr Val Phe Val Leu Asn Val His His Arg Ser Pro Arg Thr His Thr Met Pro Ala
              1030                   1050                      1070
TGG GTG CGT AGA GTC TTC CTG GAC ATC GTG CCT CGC CTC CTC TTC ATG AAG CGC CCC TCT
Trp Val Arg Arg Val Phe Leu Asp Ile Val Pro Arg Leu Leu Phe Met Lys Arg Pro Ser
              1090                   1110                      1130
GTG GTC AAA GAC AAC TGC CGG AGA CTT ATT GAG TCC ATG CAC AAG ATG GCC AAC GCC CCC
Val Val Lys Asp Asn Cys Arg Arg Leu Ile Glu Ser Met His Lys Met Ala Asn Ala Pro
              1150                   1170                      1190
CGC TTC TGG CCA GAG CCT GTG GGC GAG CCC GGC ATC TTG AGT GAC ATC TGC AAC CAA GGT
Arg Phe Trp Pro Glu Pro Val Gly Glu Pro Gly Ile Leu Ser Asp Ile Cys Asn Gln Gly
              1210                   1230                      1250
CTG TCA CCT GCC CCA ACT TTC TGC AAC CCC ACG GAC ACA GCA GTC GAG ACC CAG CCT ACG
Leu Ser Pro Ala Pro Thr Phe Cys Asn Pro Thr Asp Thr Ala Val Glu Thr Gln Pro Thr
              1270                   1290                      1310
TGC AGG TCA CCC CCC CTT GAG GTC CCT GAC TTG AAG ACA TCA GAG GTT GAG AAG GCC AGT
Cys Arg Ser Pro Pro Leu Glu Val Pro Asp Leu Lys Thr Ser Glu Val Glu Lys Ala Ser
              1330                   1350                      1370
CCC TGT CCA TCG CCT GGC TCC TGT CCT CCA CCC AAG AGC AGC AGT GGG GCT CCA ATG CTC
Pro Cys Pro Ser Pro Gly Ser Cys Pro Pro Pro Lys Ser Ser Ser Gly Ala Pro Met Leu
              1390                   1410                      1430
ATC AAA GCC AGG TCC CTG AGT GTC CAG CAT GTG CCC AGC TCC CAA GAA GCA GCA GAA GAT
Ile Lys Ala Arg Ser Leu Ser Val Gln His Val Pro Ser Ser Gln Glu Ala Ala Glu Asp
              1450                   1470                      1490
GGC ATC CGC TGC CGG TCT CGG AGT ATC CAG TAC TGT GTT TCC CAA GAT GGA GCT GCC TCC
Gly Ile Arg Cys Arg Ser Arg Ser Ile Gln Tyr Cys Val Ser Gln Asp Gly Ala Ala Ser
              1510                   1530                      1550
CTG GCT GAC AGC AAG CCC ACC AGC TCC CCG ACC TCC CTG AAG GCC CGT CCA TCC CAG CTT
Leu Ala Asp Ser Lys Pro Thr Ser Ser Pro Thr Ser Leu Lys Ala Arg Pro Ser Gln Leu
```

FIG. 2B

```
       1570                        1590                        1610
CCC GTG TCA GAC CAG GCC TCT CCA TGC AAA TGC ACA TGC AAG GAA CCA TCT CCT GTG TCC
Pro Val Ser Asp Gln Ala Ser Pro Cys Lys Cys Thr Cys Lys Glu Pro Ser Pro Val Ser
       1630                        1650                        1670
CCA GTC ACT GTG CIC AAG GCG GGA GGC ACC AAA GCA CCT CCC CAA CAC CTG CCC CTG TCA
Pro Val Thr Val Leu Lys Ala Gly Gly Thr Lys Ala Pro Pro Gln His Leu Pro Leu Ser
       1690                        1710                        1730
CCA GCC CTG ACA CGG GCA GTA GAA GGC GTC CAG TAC ATT GCA GAC CAC CTC AAG GCA GAA
Pro Ala Leu Thr Arg Ala Val Glu Gly Val Gln Tyr Ile Ala Asp His Leu Lys Ala Glu
       1750                        1770                        1790
GAC ACT GAC TTC TCG GTG AAG GAG GAC TGG AAA TAC GTG GCC ATG GTC ATT GAC CGA ATC
Asp Thr Asp Phe Ser Val Lys Glu Asp Trp Lys Tyr Val Ala Met Val Ile Asp Arg Ile
       1810                        1830                        1850
TTC CTC TGG ATG TTC ATC ATT GTC TGC CTT CTG GGC ACT GTG GGA CTC TTC CTG CCT CCC
Phe Leu Trp Met Phe Ile Ile Val Cys Leu Lue Gly Thr Val Gly Leu Phe Leu Pro Pro
       1870↓                       1890               1917
TGG CTG GCT GCT TGC TGA    TGGCTTCGACAGTGTTCTCAGGCTCACGTCTCCTGCTGACTTTGTTTCCCAG
Trp Leu Ala Ala Cys .
     1943                          1969                       1997
TTTCTTCTCCGCACAAGTTGGCCTCCCTTCATTTATTCCTGTTATTTTGGGCTTCGTGTTATTAATATCCTTCCCTGCC
     2022                          2048
TCTGTGGCGCATTGTAAGTTTTAAAAATTAATAGACCAAAGCC...3'
                                  ------

4-2 cDNA: 3' end
     1867↓                 1884                     1912
CCC TGG CTG GCT GGT ATG ATC TAG    GGACGTGGTGGTGCCCAGCTCCCACATCTCTGTAGGGCCATAC
Pro Trp Leu Ala Gly Met Ile .
           1937                      1963                      1991
GACTCGTCAGTCACCCACATCTTCCAAACCGGCTGACCATGAGACACCCTAGGAGAGAGATGATGCTTCTTGGGAGATG
           2016                      2042                      2070
GAAGTTGGCCCTGGTTCTAGTCAGACTATGGGCGTGGTTGGAGAGAAATGAGGGCTGATACAGTTGCAGGCCGAGTCCC
           2095                      2121                      2149
CATTAAAGTTTCTCCAGAGCAAGTGGCAGTACTCCCTGACTTACAGACAGCACACACCCATCTGTGTCACAGAGAATGA
   ------  2174                      2200                      2228
TCCCGAGTTGATCTCAGTTGTCCTTTGAGGCCATGAAAAATTCATCCACCTTGAGGAACCAGAGCCTCTCATGCTGTGG
           2253                      2279                      2307
GATCAATAAGACCAGGAATCTCCCACTGTGACTCTGCTGGCCACACCCTCTCCCTCCCCAAGAAGTGGTCCCTCATCC
CCCAATTC...3'
```

FIG. 2C

```
....GTGCATGGACTA
                                                     -240
ATAAGTCTCCGGCAGTTGTCTTTGACCACAGAGGGACGAGCGGCCGGCACGCGCGATGAAGTTGGGTGCCGCAGCTCTCGGAGCGGAGGCGCGGCACAGCCGGCGAGCCGCCGCA
                -210                        -180                         -150                            -120
                                                     Met Glu Ile Gly Gly Pro Gly Ala Pro Pro Leu Leu Leu Pro Leu Leu Leu Gly Thr
                                                     ATG GAG ATC GGT GGC CCC GGG GCG GCG CCG CCG CTG CTG CTG CCG CTG CTG CTA GGG ACC
GCGTGTAGAGCCCGCCTCGCGTGCGCC                              1                                                -10
             -90                             -20                                                              -30
                -1 1                                                      10                                                    20
Gly Leu Pro Ala Glu Ser His Ile Glu Thr Arg Ala His Ala Pro Pro Leu Leu Leu Lys Arg Leu Phe Ser Gly Tyr Asn Lys Trp
GGC CTC TTG CCT GCT GAA AGC CAC ATA GAG ACC CGG GCC CAT GCG CCC CCG CTG CTC CTG AAG AGA CTC TTC TCC GGT TAC AAC AAG TGG
         -11                                  1                                             30                          60
                                 30                                              40                                 50
Ser Arg Pro Val Gly Asn Ile Ser Asp Val Val Leu Arg Phe Gly Leu Ser Ile Ala Gln Ile Leu Asp Val Asp Glu Lys Asn Gln
TCT CGG CCA GTA GGC AAT ATC TCA GAT GTG GTC CTC CGC TTT GGC TTG TCC ATT GCT CAG CTC ATT GAC GTG GAC GAG AAG AAC CAG
                            90                                             120                                  150
                        60                                             70                                          80
Met Met Thr Asn Thr Val Trp Val Lys Gln Glu Trp His Asp Leu Arg Trp Asp Pro Gly Tyr Asp Phe Ala Val Asn Val Thr Ser Ile
ATG ATG ACA AAC ACC GTG TGG GTG AAG CAG GAG TGG CAC GAC CTG CGC TGG GAC CCT GGT TAC GAC TTT GCA GTC AAT GTC ACC TCC ATC
                         180                                           210                                     240
                     90                                           100                                             110
Arg Ile Pro Ser Glu Leu Ile Trp Arg Pro Asp Ile Val Leu Tyr Asn Asn Ala Asp Gly Asp Phe Ala Val Thr Leu Thr His Leu Thr Leu Lys Ala
CGC ATC CCC TCT GAA CTC ATC TGG AGG CCT GAC ATC GTC CTC TAC AAC AAT GCG GAT GGA GAC TTT GCA GTC ACC CGT ACC CAC CTG ACC CTG AAG GCC
                         270                                           300                                            330
                     120                                          130                                         140
Gly Arg Val Gln Trp Thr Pro Ala Ile Lys Ser Lys Tyr Asp Val Thr Pro Phe
His Leu Phe Tyr Asp Lys Arg Val Gln Trp Thr Pro Ala Ile Lys Ser Ser Cys Ser Ile Asp Val Thr Phe Phe Pro Phe Asp
CAC CTG TTC TAT GAC AAG AGG GTG CAG TGG ACA CCA GCC ATC AAG TCC AAG TAC GAC TGC TCC AGC ATC GAC GTC ACC TTC TTC CCC TTT GAC
                         360                                          390                                    420
                     150                                          160                                    170
Gln Gln Asn Cys Thr Met Lys Phe Gly Ser Trp Thr Tyr Asp Lys Ala Lys Ile Asp Leu Val Ser Ile His Ser Arg Val Asp Gln Leu
CAG CAG AAC TGT ACC ATG AAG TTT GGA TCC TGG ACC TAC GAC AAG GCC AAG ATT GAC TTA GTG AGC ATT CAT AGC CGT GTG GAC CAA CTG
                         450                                          480                                     510
```

```
Asp Phe Trp Glu Ser  180 Gly Glu Trp Val Ile  Val Asp Ala Val Gly  190 Thr Tyr Asn Thr Arg  Lys Tyr Glu Cys Cys  200 Ala Glu Ile Tyr Pro
GAC TTC TGG GAA AGT      GGG GAG TGG GTC ATC  GTG GAT GCT GTG GGC      ACC TAC AAC ACC AGG  AAG TAC GAG TGC TGT      GCC GAG ATC TAT CCT
                     540                                                570                                           600

Asp Ile Thr Tyr Ala  210 Phe Ile Ile Arg Arg  Leu Pro Leu Phe Tyr  220 Thr Ile Asn Leu Ile  Ile Pro Cys Leu Thr  230 Ser Cys Leu Thr Ile
GAC ATC ACC TAT GCC      TTC ATC ATC CGA CGC  CTG CCG CTA TTC TAC      ACC ATC AAC CTC ATC  ATC CCG TGC CTG ACC      TCC TGT CTC ACC ATC
                     630                                                660                                           690

Val Leu Val Phe Tyr  240 Pro Ser Glu Cys Gly  Lys Val Thr Arg Lys  250 Cys Ile Ser Val Leu  Thr Leu Ser Leu Leu  260 Phe Leu Leu Leu Leu
GTC CTG GTC TTC TAT      CCT TCA GAG TGT GGC  AAG GTC ACA AGG AAG      TGC ATC TCG GTG CTG  ACA CTG CTT TCT CTC      TTC GTG CTG CTC CTC
                     720                                                750                                           780

Ile Thr Glu Ile Ile  270 Ser Thr Ser Leu Val  Ile Pro Leu Ile Pro  280 Gly Tyr Glu Ile Leu  Phe Thr Met Ile Phe  290 Val Phe Leu Ser Ile
ATC ACC GAG ATC ATC      TCC ACC TCG CTG GTG  ATC CCG CTC ATC CCG      GGC GAG TAC CTC CTC  TTC ACC ATG ATC TTC      GTC TTC CTC TCC ATC
                     810                                                840                                           870

Val Ile Thr Val Phe  300 Leu Asn Val His His  Arg Ser Pro Arg Thr  310 Thr Arg Asp Thr Met  Pro Ala Trp Val Arg  320 Val Arg Arg Asp Ile
GTC ATC ACG GTC TTC      CTC AAT GTG CAC CAC  CGC TCG CCA CGC ACG      ACA CGC GAC ACG ATG  CCC GCC TGG GTG GTG      GTG CGT AGA GAC ATC
                     900                                                930                                           960

Val Pro Arg Leu Leu  330 Met Phe Leu Leu Phe  Lys Arg Pro Ser Val  340 Asn Cys Arg Arg Leu  Ile Glu Ser Met His  350 Met Ala Asn Ala
GTG CCT CGC CTC CTC      ATG TTC CTC CTC TTC  AAG CGC CCC TCT GTC      AAC TGC CGG AGA CTT  ATT GAG TCC ATG CAC      ATG GCC AAC GCC
                     990                                                1020                                          1050

Pro Arg Phe Trp Pro  360 Glu Val Gly Glu Pro  Gly Ile Leu Ser Asp  370 Asp Ile Cys Asn Gln  Gly Leu Ser Pro Ala  380 Thr Phe Cys Asn
CCC CGC TTC TGG CCA      GAG GTG GGC GAG CCC  GGC ATC TTG AGT GAC      ATC TGC AAC CAA GGT  CTG TCA CCT GCC CCA      ACT TTC TGC AAC
                     1080                                               1110                                          1140

Pro Thr Asp Thr Ala  390 Val Glu Thr Gln Pro  Thr Cys Arg Ser Pro  400 Leu Glu Val Pro Asp  Lys Thr Ser Lys Thr  410 Val Glu Lys Ala
CCC ACG GAC ACA GCA      GAG GTG ACG CAG CCG  ACG TGC AGG TCA CCC      CTT GAG GTC CCT GAC  AAG ACA TCA AAG ACA      GTT GAG AAG GCC
                     1170                                               1200                                          1230
```

```
                    420                           430                           440
Ser Pro Cys Pro Ser Pro Gly Ser Cys Pro Pro Pro Lys Ser Ser Ser Gly Ala Pro Met Leu Ile Lys Ala Arg Ser Val Gln
AGT CCC TGT CCA TCG CCT GGC TCC TGT CCT CCA CCC AAG AGC AGC AGT GGG GCT CCA ATG CTC ATC AAA GCC AGG TCC AGT GTC CAG
                 1260                          1290                          1320
                    450                           460                           470
His Val Pro Ser Ser Gln Glu Ala Ala Glu Asp Gly Ile Arg Cys Ser Arg Ser Ile Gln Tyr Cys Val Ser Gln Asp Gly Ala Ala
CAT GTG CCC AGC TCC CAA GAA GCA GCA GAA GAT GGC ATC CGC TGC TCT CGG AGT ATC CAG TAC TGT GTT TCC CAA GAT GGA GCT GCC
                 1350                          1380                          1410
                    480                           490                           500
Ser Leu Ala Asp Ser Lys Pro Thr Ser Ser Pro Thr Ser Leu Lys Arg Pro Ser Gln Leu Pro Val Ser Asp Gln Ala Ser Pro Cys
TCC CTG GCT GAC AGC AAG CCC ACC AGC TCC CCG ACC TCC CTG AAG CGT CCA TCC CAG CTT CCC GTG TCA GAC CAG GCC TCT CCA TGC
                 1440                          1470                          1500
                    510                           520                           530
Lys Cys Thr Cys Lys Glu Pro Ser Pro Val Ser Pro Val Thr Ser Leu Lys Ala Gly Gly Thr Lys Ala Pro Gln His Leu Pro Leu
AAA TGC ACA TGC AAG GAA CCA TCT CCT GTG TCC CCA GTC ACT CTC AAG GCG GGA GGC ACC AAA GCA CCT CAA CAC CTG CCC CTG
                 1530                          1560                          1590
                    540                           550                           560
Ser Pro Ala Leu Thr Arg Ala Val Ala Val Gln Gly Val Gln Tyr Ile Ala Asp His Leu Ala Glu Asp Thr Asp Phe Ser Val Lys Glu Asp
TCA CCA GCC CTG ACA CGG GCA GTA GAA GGC GTC CAG TAC ATT GCA GAC CAC CTC GCA GAA GAC ACT GAC TTC TCG GTG AAG GAG GAC
                 1620                          1650                          1680
                    570                           580                           590
Trp Lys Tyr Val Ala Met Val Ile Asp Arg Ile Phe Leu Trp Met Phe Ile Ile Val Cys Leu Leu Gly Thr Val Gly Leu Phe Leu Pro
TGG AAA TAC GTG GCC ATG GTT ATT GAC CGA ATC TTC CTC TGG ATG TTC ATC ATT GTC TGC CTT CTG GGA ACT GTG GGA CTC TTC CTG CCT
                 1710                          1740                          1770
                    600
Pro Trp Leu Ala Gly Met Ile *
CCC TGG CTG GCT GGT ATG ATC TAG  GGACGTGGTGGTGCCAGCTCGTCAGTCCACCCACATCTTCCAAACCGGCTGACCATGAG
                 1800                        1830                                  1860                         1890
ACACCCTAGGAGAGATGATGCTTCTGGGAGATGGAAGTTGGCCCTGGTGTTCTAGTCAGACTATGGGCGTGGTTGGAGAGAAATGAGGGCTGATACAGTTGCAGGCCCAGTCCCATT
       1920                            1950                          1980                          2010
```

FIG. 2F

```
ALPHA4  G T G A P P P L L L P L L L L G T G L L P A S S H
ALPHA3          M G V V L L P P P L S M L M L V L M L L P A A S A
ALPHA1              M E L S T V L L L L G L S S A G L V L G
                              signal peptide ALPHA4  I E T R A H A E E R L K R L F S G Y N K W S R P V G
ALPHA3  - - - - S E A E H R L F Q Y L F E D Y N E I I R P V A
ALPHA1  - - - - S E H E T R L V A K L F E D Y S S V V R P V E

*
ALPHA4  N I S D V V L R F G L S I A Q L I D V D E K N Q M H
ALPHA3  N V S H P V I I Q F E V S M S Q L V K V D E V N Q I H
ALPHA1  D H R E I V Q V T V G L Q L I Q L I N V D E V N Q I V

ALPHA4  T T N V V K Q E W H D Y K L R W D P G D Y E N V T S
ALPHA3  E T N L W L K Q I W N D Y K L K W K P S D Y Q G V E F
ALPHA1  T T N V R L K Q Q W V D Y N L K W N P D D Y G G V K K

ALPHA4  I R I P S E L W R P D I V L Y N N A D G D F A V T H
ALPHA3  M R V P A E K I W K P D I V L Y N N A D G D F Q V D D
ALPHA1  I H I P S E K I W R P D V V L Y N N A D G D F A I V K

ALPHA4  L T K A H L F Y D G R V Q W T P P A I Y K S S C S I D
ALPHA3  K T K A L L L K Y T G E V T W I P P A I F K S S C K I D
ALPHA1  F T K V L L L D Y T G H I T W T P P A I F K S Y C E I I
                          *            ↓
ALPHA4  V T F F P F D Q Q N C T M K F G S W T Y D K A K I D L
ALPHA3  V T Y F P F D Y Q N C T M K F G S W S Y D K A K I D L
ALPHA1  V T H F P F D E Q N C S M K L G T W T Y D G S V V A I

ALPHA4  V S I H S R V D Q L D F W E S G E W V I D A V G T Y
ALPHA3  V L I G S S M N L K D Y W E S G E W A I I K A P G Y K
ALPHA1  N P E S D Q P D L S N F M E S G E W V I K E A R G W K
                    ↓ ↓
ALPHA4  N T R K Y E C C - A E I Y P D I T Y A F I I R R L P L
ALPHA3  H E I K Y N C C - E E I Y Q D I T Y S L Y I R R L P L
ALPHA1  H W V F Y S C C P T T P Y L D I T Y H F V M Q R L P L
                                                    <----

ALPHA4  F Y T I N L I I P C L L I S C L T V L V F Y L P S E C
ALPHA3  F Y T I N L I I P C L L I S F L T V L V F Y L P S D C
ALPHA1  Y F I V N V I I P C L L F S F L T S L V F Y L P T D S
        -----------------MSR I-------------------->

ALPHA4  G E K V T L C I S V L L S L T V F L L L I T E I I P S
ALPHA3  G E K V T L C I S V L L S L T V F L L V I T E T I P S
ALPHA1  G E K M T L S I S V L L S L T V F L L V I V E L I P S
        <----------------MSR II-------------------->

ALPHA4  T S L V I P L I G E Y L L F T M I F V T L S I V I T V
ALPHA3  T S L V I P L I G E Y L L F T M I F V T L S I V I T V
ALPHA1  T S S A V P L I G K Y M L F T M V F V I A S I I T V
        <----------------MSR III---------->
```

FIG.3A

```
ALPHA4   F V L N V H H R S P   R T H T M P   A W V R V F L D I V
ALPHA3   F V L N V H Y R T P   T T H T M P   T W V K A V F L N L L
ALPHA1   I V I N T H H R S P   S T H I M P   E W V R K V F I D T I
         -------->

ALPHA4   P R L L F - - - M K R P S V V K D N C R L I E S M H
ALPHA3   P R V M F - - - M T R P T S G E G D T P K T - - - - -
ALPHA1   P N I M F P S T M K R P S R D K Q E K R I F - - - - -

ALPHA4   K M A N A P R F W P E P V G E P G I L S D I C N Q G L
ALPHA3   - - - - - - - - - - - - R T F Y G A E L S N L N C F S R
ALPHA1   - - - - - - - - - - - - T E D I D I S D I S G K P G

ALPHA4   S P A P T F C N P T D T A V E T Q P T C R S P P L E V
ALPHA3   A D S K S C K E G Y P C Q D G T C G Y C H H R R V K I
ALPHA1   P P P M G F H - - - - - - - - - - - - - - - - - - -

ALPHA4   P D L K T S E V E K A S P C P S P G S C P P P K S S S
ALPHA3   S N F - - - - - - - - - - - - - - S A N L T R S S S
ALPHA1   - - - - - - - - - - - - - - - - - - - - - - - - -

ALPHA4   G A P M L I K A R S L S V Q H V P S S Q E A A E D G I
ALPHA3   S E S V - - - - - - - - - - - - - - - - - - - - - -
ALPHA1   - - - - - - - - - - - - - - - - - - - - - - - - -

ALPHA4   R C R S R S I Q Y C V S Q D G A A S L A D S K P T S S
ALPHA3   - - - - - - - - - - - - - - - - - - - - - - - - -
ALPHA1   - - - - - - - - - - - - - - - - - - - - - - - - -

ALPHA4   P T S L K A R P S Q L P V S D Q A S P C K C T C K E P
ALPHA3   - - - - - - - - - - - - - - - - - - - - - - - - -
ALPHA1   - - - - - - - - - - - - - - - - - - - - - - - - -

ALPHA4   S P V S P V T V L K A G G T K A P P Q H L P L S P A L
ALPHA3   - - - - - - - - - - - - - N A V L S L S A L S P E I
ALPHA1   - - - - - - - - - - - - - S P L I K H P E V
                                              <--------

ALPHA4   T R A V E G V Q Y I A D H L K A E D T D F S V K E D W
ALPHA3   K E A I Q S V K Y I A E N M K A Q N V A K E I Q D D W
ALPHA1   K S A I E G V K Y I A E T M K S D Q E S N N A A E E W
         amphipathic helix-------------->

ALPHA4   K Y V A M V I D R I F L W M F I I V C L L G T V G L F
ALPHA3   K Y V A M V I D R I F L W V F I L V C I L G T A G L F
ALPHA1   K Y V A M V M D H I L L G V F M L V C L T G T L A V F
                                         <----------MSR IV----------

ALPHA4   L P P W L A G M I
ALPHA3   L Q P L M A - R D D T
ALPHA1   A G R L I E L H Q Q G
         -->
```

FIG.3B

FIG. 4A
Clone 4-1;
Antisense
FIG. 4B
Clone 4-1;
Sense
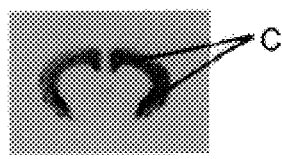
C
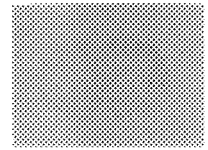
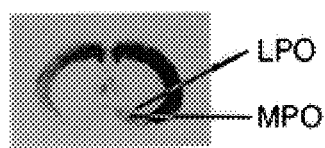
LPO
MPO
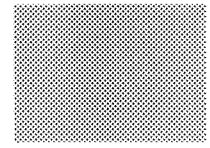
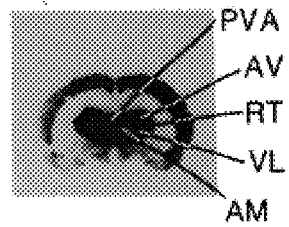
PVA
AV
RT
VL
AM
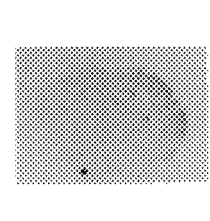
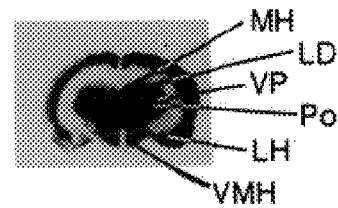
MH
LD
VP
Po
LH
VMH
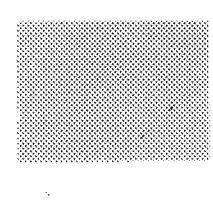
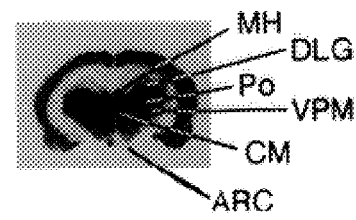
MH
DLG
Po
VPM
CM
ARC
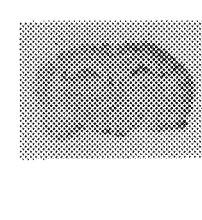
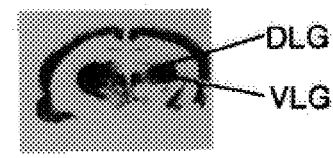
DLG
VLG
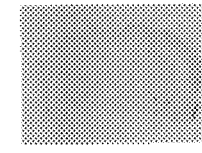
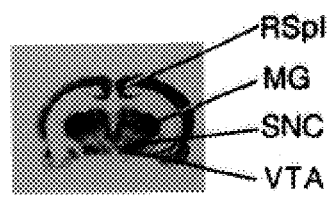
RSpl
MG
SNC
VTA
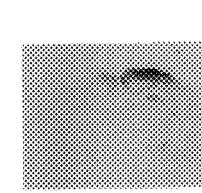

PROBE: Alpha 4

PROBE: Alpha 3

```
     -179
5'........ GGGGAACACAACCGGGACCGGCAAGAAGCCGGACCTCCCCTCGTTGCAGGAACTGCCGTTCAGTGAGCACTTTAGACC
                                                                                      -1
TGGAGGCCGGCCGAGCCCACCCGGGAGCAGGGCGGCCTGCGCGGGCTTCAGCACCGGACAGCCCTAGTATCCGAGAGGCTGCCGCT
                                                                               -100

ATG CTG GCT TGC ATG GCC GGG CAC TCC AAC TCA ATG GCG CTG TTC AGC TTC CTT CTT TGG CTG TGC TCA GGG
Met Leu Ala Cys Met Ala Gly His Ser Asn Ser Met Ala Leu Phe Ser Phe Leu Leu Trp Leu Cys Ser Gly
 1                                          30                                          150

GTT TTG GGA ACT GAC ACA GAG GAG CAT CTC CTA GTG GAG CAT CTC TTA CTC ATG GCG CTG TTC AGC TAT AAC AAG CTG ATT CGT
Val Leu Gly Thr Asp Thr Glu Glu His Leu Leu Val Glu His Leu Leu Leu Met Ala Leu Phe Ser Tyr Asn Lys Leu Ile Arg
26          90                              120
```

| | | | | | | | | | |
|---|---|---|---|---|---|---|---|---|---|
| TTT Phe 176 | CGC Arg | TCA Ser | TGG Trp | ACC Thr | TAC Tyr | GAC Asp | CGT Arg | ACT Thr | GAG Ile | ATT Glu | GAC Asp | CTG Leu | GTG Val | CTC Leu | AAA Lys | AGT Ser | GAT Asp | GTG Val | GCC Ala | AGT Ser | CTG Leu | GAT Asp | GAC Asp | TTC Phe |

(Figure 7C: DNA/protein sequence listing, codons 176–351)

```
GAG GCG GTT TTC TTC CGT GAA GGT CCT GCG GCT GAC CCA TGC TTT GTC AAC CCT GCA TCA GTG CAG GGC
Glu Ala Val Phe Phe Arg Glu Gly Pro Ala Ala Asp Pro Cys Phe Val Asn Pro Ala Ser Val Gln Gly
376                    1140                             1170                            1200

TTG GCT GGG GCT TTC CGA GCT TTC CGA GAG CCC ACT GCA GCC CGG GGC TCT CGC CCA TGC AGC TGT GGC CTC
Leu Ala Gly Ala Phe Arg Ala Phe Arg Glu Pro Thr Ala Ala Arg Gly Ser Arg Pro Cys Ser Cys Gly Leu
401                                    1230                             1260                   1350

CGG GAA GCA GTG GAT GGC GTA CGC TTC ATT GCG GAC CAC ATG AGT CGA GAG GAT GAC CAG AGT GTG AGG GAG
Arg Glu Ala Val Asp Gly Val Arg Phe Ile Ala Asp His Met Ser Arg Glu Asp Asp Gln Ser Val Arg Glu
426                    1290                             1320

GAC TGG AAA TAC GTT GCC ATG GTG ATC GAC CGC CTG TTC CTG TGG ATC TTT GTC TGT GTC TTT GGG ACC
Asp Trp Lys Tyr Val Ala Met Val Ile Asp Arg Leu Phe Leu Trp Ile Phe Val Cys Val Phe Gly Thr
451                                    1380                             1410                   1500

GTC GGC ATG TTC CTG CAG CCT CTC TTC CAG AAC TAC ACT GCC ACT ACC TTC CTC CAC CCT GAC CAC TCA GCT CCC
Val Gly Met Phe Leu Gln Pro Leu Phe Gln Asn Tyr Thr Ala Thr Thr Phe Leu His Pro Asp His Ser Ala Pro
476                    1440                             1470

AGC TCC AAG TGAGGTCTCATTCATTTGCAGCTCCTCACCCGTGACCCCTGCGGTTCAGTACTGGGTGCAAGATGATCTCTCCCACTCCACTGA
Ser Ser Lys                                                                                   1596
501
                                                                                              1695
AGCCTGCTTCACACCTCCGTTCACACATAGTCCTCCAGCCTGGAGGCTGGACCCGCTGCCTTGTGGTCGAGCCTTCTCCTTCCCTCTGAGCTCGTTCA
                                                                                              1794
GGCAGGAGTGCCAATGGTGGGGGCCACGGCTGGTAAGTAGAGGCCAGAGATCACAGAGCCACCTACCCCGATGAGGTGCTGGAGAAGGCGCCAAGAAAG
                                                                                              1893
AGACAGAGTTATCTGTGACCTCCAAGTCATCGGAGAGTCTCAGACTCTGGCAGAGTGCGGTAGTACTTGGCGCCACCCA
                                                                                              1992
CTTAAGTGAGCGACGACACTGGTCTGGGAGGACTCGAAGTGTTGGGGAGCTCTCTTGGGAGCTCGGTCTCCCACCCTGTACCCTCAGAGGGCTCCAGACCCGG
           2017
GCTTCAGGTTCCCTTCTGCCAGTGC........3'
```

FIG.10A
ANTISENSE
FIG.10B
SENSE
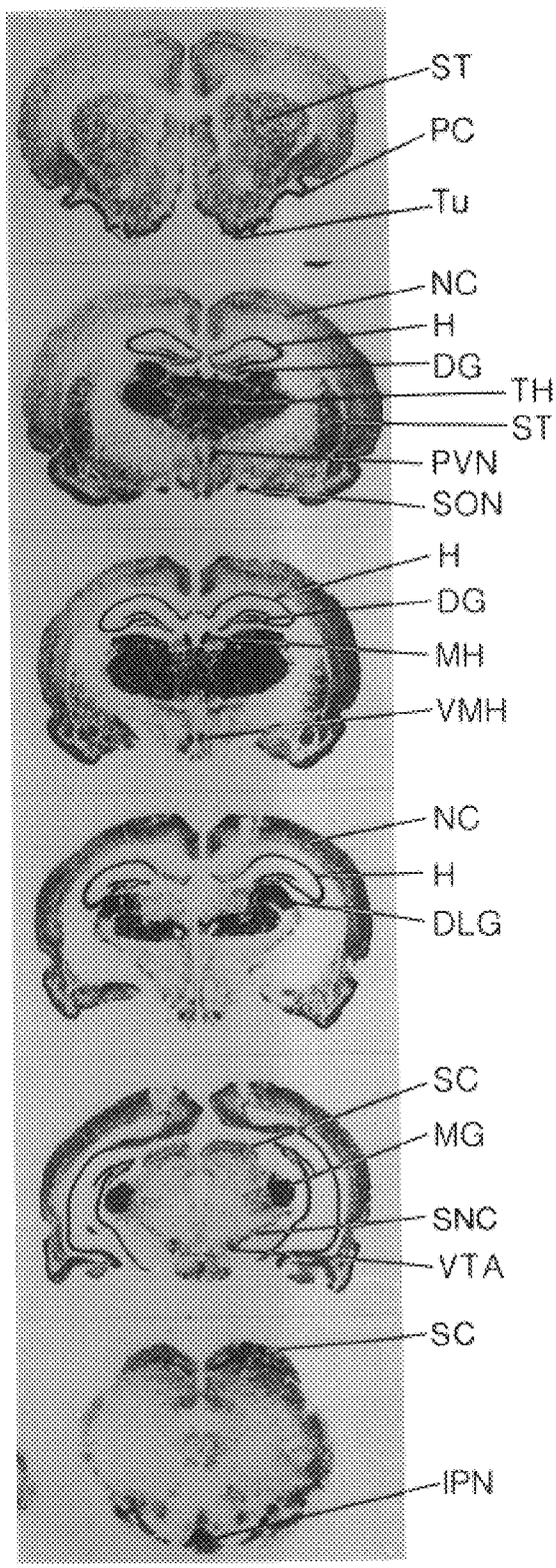
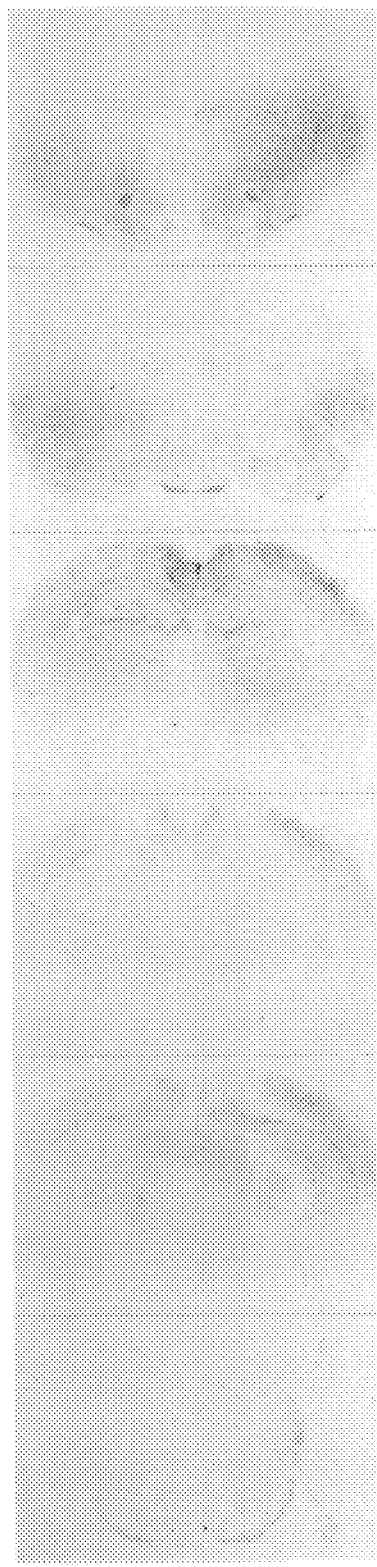

FIG. 11

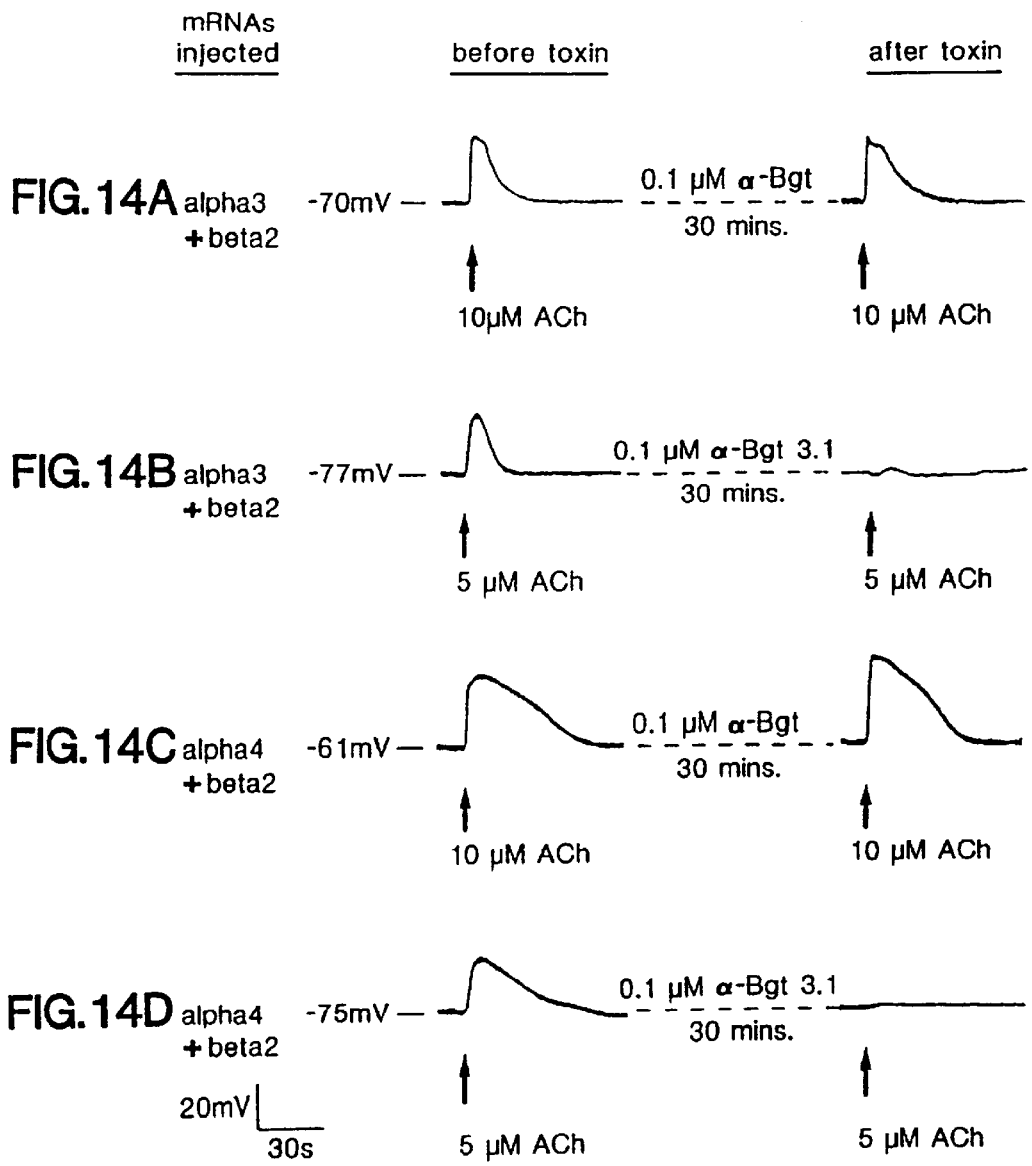

FIG. 15C

```
270                              300                              330
ATC TGG ATC CCA GAC ATT GTC CTC TAC AAC AA gtaaga.......ctcttcccag T GCA GAT GGG GAG TTT GCG GTG ACC CAC ATG ACC AAG
Ile Trp Ile Pro Asp Ile Val Leu Tyr Asn As                        n Ala Asp Gly Glu Phe Ala Val Thr His Met Thr Lys
90                                                                100                                  110

360                              390                              420
GCT CAC CTC TTC TTC ACG GGC GTG CAC TGG GTG CCC CCA GCC ATC TAC AAG AGC ATC GAT GTG ACC TTC CCC TTC
Ala His Leu Phe Phe Thr Gly Val His Trp Val Pro Pro Ala Ile Tyr Lys Ser Ile Asp Val Thr Phe Pro Phe
    120                              130                              140

450                              480                              510
GAC CAG CAG AAC TGC AAG ATG TTT GGC TCC TGG ACA TAT GAC AAG GCC ATC GAT CTG GAG CAG ACA GAG AGG GTG GAC CTG
Asp Gln Gln Asn Cys Lys Met Phe Gly Ser Trp Thr Tyr Asp Lys Ala Ile Asp Leu Glu Gln Thr Arg Val Asp Leu
    150                              160                              170

540                              570                              600
AAG GAC TAC TGG GAG AGT GGC GCC ATT ATC AAT GCC ACC GGA CTG CCG CTG TTC TAT AAC AGT TAT AAG AAG TAC ATC CCA GAG ATC
Lys Asp Tyr Trp Glu Ser Gly Ala Ile Ile Asn Ala Thr Gly Leu Pro Leu Phe Tyr Asn Ser Tyr Lys Lys Tyr Ile Pro Glu Ile
    180                              190                              200

630                              660                              690
CCC GAT GTC ACC TAC TAC TTT GTG GCC CGG CTG CCG CTG TTC TAT ACC AAC CTC ATC ATC CCA TGC ATC CTC TGC CTC
Pro Asp Val Thr Tyr Tyr Phe Val Ala Arg Arg Leu Pro Leu Phe Tyr Thr Asn Leu Ile Ile Pro Cys Ile Leu Cys Leu
    210                              220                              230

720                              750                              780
ACT GTG CTC GTG TTC TAC CTG CCT TCC GAG TGT GGA GAG AAG ATC ACG CTG CTA TCT CTC ACT GTC CTG CTG
Thr Val Leu Val Phe Tyr Leu Pro Ser Glu Cys Gly Glu Lys Ile Thr Leu Leu Ser Leu Thr Val Leu Leu
    240                              250                              260

810                              840                              870
CTC ATC ACG GAG ATC ATC CCG ACC TCG CTG GTC CCA CTG ATC GGC TAC GAG GTG GGC TAC CTG CTC TTC ACC ATG ATC GTC ATG ATC GTC CTC TCT
Leu Ile Thr Glu Ile Ile Pro Thr Ser Leu Val Pro Leu Ile Gly Tyr Glu Val Gly Tyr Leu Leu Phe Thr Met Ile Val Phe Leu Ser
    270                              280                              290
```

FIG. 15D

```
ATC GTT ATC ACA GTC TTC GTG CTC AAT GTA CAC CAC CGC TCC CCC AGC ACC CAC AAC ATG CCC AAC TGG GTA AGG GTA GCC CTG CTA GGC
Ile Val Ile Thr Val Phe Val Leu Asn Val His His Arg Ser Pro Ser Thr His Asn Met Pro Asn Trp Val Arg Val Ala Leu Leu Gly
                                     300                           310                           320

CGG GTG CCC AGG TGG CTG ATG AAC CGG CCC CTG CCA CCT ATG GAG CTC ATG GGC TCC GAT CCG TCC AGC CTC AAG CTG GAT CCC TCA TAC CAT
Arg Val Pro Arg Trp Leu Met Asn Arg Pro Leu Pro Pro Met Glu Leu Met Gly Ser Asp Pro Ser Ser Leu Lys Leu Asp Pro Ser Tyr His
                  330                           340                           350

TGG CTA GAG ACT AAC ATG GAT GCT GGA GAA AGG GAG GAG ACA GAG GAA GAA GAT GAA GAA ATA TGT GTG TGT GCA GGC
Trp Leu Glu Thr Asn Met Asp Ala Gly Glu Arg Glu Glu Thr Glu Glu Glu Asp Glu Glu Ile Cys Val Cys Ala Gly
                  360                           370                           380

CTT CCA GAC TCT TCG ATG GGT GTC CTC TAT GGC CAT GGC GGT CTG CAT CTG AGA GCC ATG GAG ACC CCA TCC CAG GCT
Leu Pro Asp Ser Ser Met Gly Val Leu Tyr Gly His Gly Gly Leu His Leu Arg Ala Met Glu Thr Pro Ser Gln Ala
                  390                           400                           410

AGC GAG ATT CTG CTG TCA CCT CAA ATA CAG AAA GCA CTA GAA GGT GTA CAC TAC ATT GCT GAC CGT CTG AGG TCT GCT GAC TCT
Ser Glu Ile Leu Leu Ser Pro Gln Ile Gln Lys Ala Leu Glu Gly Val His Tyr Ile Ala Asp Arg Leu Arg Ser Ala Asp Ser
                  420                           430                           440

1350                           1380
TCG gtgagt........ctaacttcag GTG AAG GAA GAC TGG AAG TAT GTG GCC ATG GTG GAC CGG ATA TTC CTC TGG CTG TTC ATT ATC
Ser                          Val Lys Glu Asp Trp Lys Tyr Val Ala Met Val Asp Arg Ile Phe Leu Trp Leu Phe Ile Ile
                                             450                           460

1470
GTC TCG TTC CTG GGG ACC ATC GGA CTC TTC CTT CCT CCA TTC CTG GCT GGA ATG ATC TAA CTTCATGTCCTTCATGTTGGCTCCAAGGTGGCCTTCGTA
Val Cys Phe Leu Gly Thr Ile Gly Leu Phe Leu Pro Pro Phe Leu Ala Gly Met Ile *
                  470                           480

1500
ACTATCTTCTAGTCTCTTCTGTGAATGAGCCATCTCTGTGAATACTCTTTTGAC........
                                       1530
```

FIG.17A
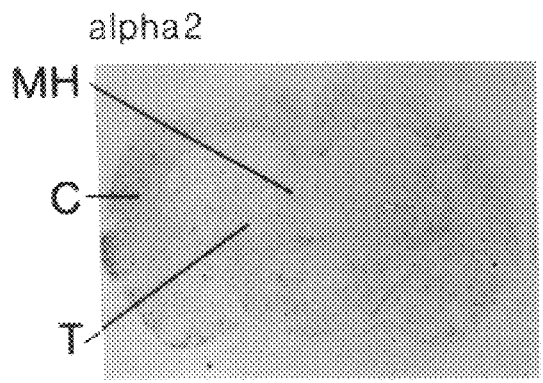
alpha2
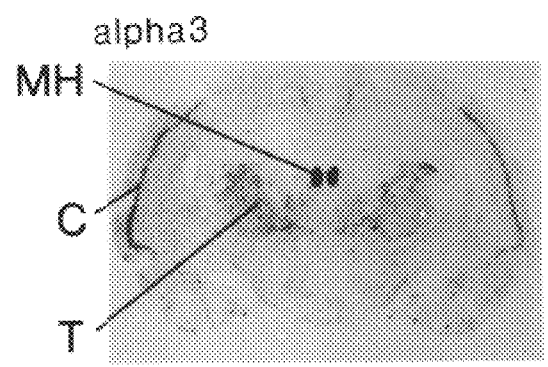
alpha3
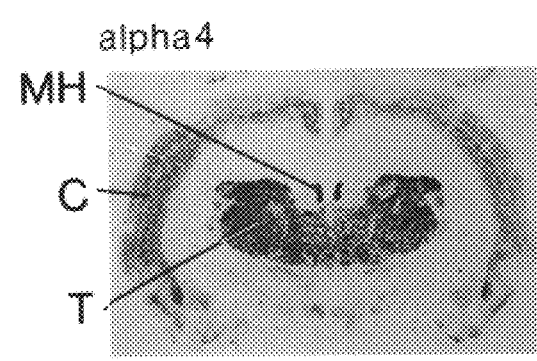
alpha4
FIG.17B
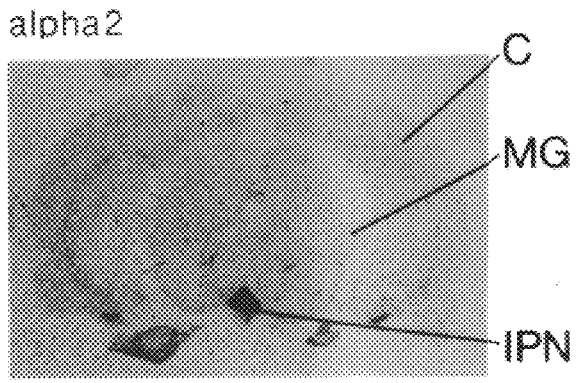
alpha2
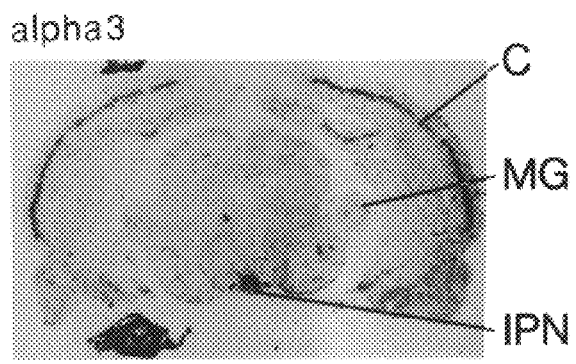
alpha3
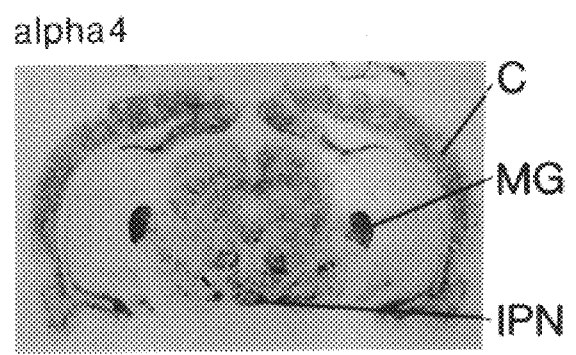
alpha4

```
5'.........GACAGACATT
                                      -240                -220                -200                -180                -160                -140
TGTCGTCATCAGCTGATTATTTCATCAGGCAGCTGGTCACGGTCCCCTGGTTTCATCAGGCTTTGAACCACTCACATTTGTTTTTTAAACCCTGATCCTTCCAGTGAAACACT

-30
CTGCCCTTGAAAGGAAAATGTCTCTCTGAAGCAGACGTC ATG ACA GGC TTC CTA AGG GTC TTC TTG GTT CTC AGT GCC ACT CTC TCA GGT TCC TGG GTG
          -120                     -100      Met Thr Gly Phe Leu Arg Val Phe Leu Val Leu Ser Ala Thr Leu Ser Gly Ser Trp Val
                                                                                   -20                                          -40

-10                                1                                        10                                          20
Thr Leu Thr Ala Gly Leu Ser Ser Val Ala Glu His Glu Asp Ala Leu Leu Arg His Leu Phe Gln Gly Tyr Gln Lys Trp Val
ACT CTT ACG GCC ACT GGA CTC AGC GTC GCT GAA CAC GAA GAC GCA CTC CTC AGA CAT TTG TTC CAA GGT TAC CAG AAA TGG GTC
                 -20                                         20                                                            60

30                                          40                                        50
Arg Pro Val Leu Asn Ser Ser Asp Ile Ile Lys Val Tyr Phe Gly Leu Lys Ile Ser Gln Leu Val Asp Val Asp Glu Lys Asn Gln Leu
CGC CCT GTG TTG AAT TCC AGT GAC ATC ATA AAA GTG TAT TTT GGA TTA AAA ATA TCC CAG CTT GTG GAT GTG GAT GAA AAG AAT CAG CTG
                80                                     100                                    120                                  140

60                                           70                                      80
Met Thr Thr Asn Val Trp Leu Lys Gln Glu Leu Arg Trp Asn Pro Glu Glu Tyr Gly Gly Ile Asn Ser Ile Lys
ATG ACA ACA AAT GTG TGG CTG AAG CAG GAA CTG AGA TTA CGC CAA GAC TTA CGT TGG AAT CCG GAA GAA TAT GGT GGA ATT AAT TCG ATA AAG
                160                                      180                                     200                                      240

90                                       100                                        110
Val Pro Ser Glu Ser Leu Trp Leu Pro Asp Ile Val Leu Phe Glu Asn Ala Asp Gly Arg Phe Glu Gly Ser Leu Met Thr Lys Ala Ile
GTT CCA TCA GAA TCG CTC TGG CTC CCG GAC ATA GTT CTC TTT GAA AAT GCT GAC GGA CGT TTT GAG GGC TCC CTC ATG ACC AAG GCC ATT
                260                                      280                                    300                                     320

120                                     130                                       140
Val Lys Ser Ser Gly Thr Val Ser Trp Thr Pro Pro Ala Ser Tyr Lys Ser Ser Cys Thr Met Asp Val Thr Phe Phe Pro Phe Asp Arg
GTG AAG TCC AGT GGA ACC GTC AGC TGG ACT CCT CCC GCC AGC TAC AAG AGT TCC TGC ACC ATG GAT GTC ACA TTT TTC CCG TTC GAC AGG
               340                                      360                                       380                                       420
```

FIG. 19A

```
                                                    150                           160                           170
Gln Asn Cys Ser Met Lys Phe Gly Ser Trp Thr Tyr Asp Gly Thr Met Val Asp Leu Ile Leu Ile Asn Glu Asn Val Asp Arg Lys Asp
CAG AAC TGC TCG ATG AAG TTT GGA TCC TGG ACT TAC GAC GGT ACC ATG GTT GAC CTC ATT CTA ATC AAT GAA AAC GTT GAC CGG AAA GAC
                                440                           460                           480                           500

180                           190                                       200
Phe Phe Asp Asn Gly Glu Trp Glu Ile Leu Asn Ala Lys Gly Met Lys Gly Asn Arg Arg Glu Gly Phe Tyr Ser Tyr Pro Phe Val Thr
TTT TTT GAT AAC GGA GAG TGG GAG ATA CTC AAC GCA AAG GGG ATG AAG GGC AAC AGA AGA GAA GGC TTT TAC TCC TAT CCG TTT GTT ACC
                                520                           540                           560                           580                           600

210                           220                           230
Tyr Ser Phe Val Leu Arg Arg Leu Pro Leu Phe Tyr Thr Leu Phe Leu Ile Ile Pro Cys Leu Gly Leu Ser Phe Leu Thr Val Leu Val
TAC TCT TTT GTC CTG AGA CGC CTG CCC TTG TTT TAC ACG CTC TTT TTG ATA ATC CCC TGC CTG GGG TTG TCT TTT CTC ACG GTC CTG GTG
                                620                           640                           660                           680

240                           250                           260
Phe Tyr Leu Pro Ser Asp Glu Gly Glu Gly Lys Leu Ser Leu Ser Thr Val Leu Val Ser Leu Thr Val Phe Leu Leu Val Ile Glu Glu
TTC TAC CTA CCC TCG GAC GAA GGG GAA GGG AAA CTC TCA TTA TCC ACC GTT TTG GTC TCT TTG CTT CTT TTA GTG ATT GAA GAA
                                700                           720                           740                           760                           780

270                           280                           290
Ile Ile Pro Ser Ser Lys Val Ile Pro Leu Ile Gly Tyr Leu Leu Phe Ile Met Ile Phe Val Thr Leu Ser Ile Ile Val Thr
ATA ATC CCG TCC TCT AAG GTC ATC CCC CTC ATT GGC GAG TAC CTG CTC TTC ATT ATG ATT TTT GTC ACG CTG TCT ATT ATC GTC ACG
                                800                           820                           840                           860

300                           310                           320
Val Phe Val Ile Asn Val His His Arg Ser Ser Ser Thr Tyr His Pro Met Ala Pro Trp Val Lys Arg Leu Phe Leu Gln Arg Leu Pro
GTT TTT GTA ATT AAT GTC CAC CAC AGA TCT TCC TCC ACG TAC CAT CCC ATG GCC CCC TGG GTG AAG AGG CTG TTT CTA CAA AGA CTC CCG
                                880                           900                           920                           940                           960

330                           340                           350
Arg Trp Leu Cys Met Lys Asp Pro Met Asp Arg Phe Ser Phe Pro Asp Gly Lys Glu Ser Asp Thr Ala Val Arg Gly Lys Val Ser Gly
AGA TGG CTT TGC ATG AAG GAC CCC ATG GAC CGC TTC TCT TTC CCG GAT GGA AAG GAG AGT GAT ACA GCC GTG AGG GGG AAA GTC TCA GGC
                                980                           1000                          1020                          1040
```

FIG. 19B

```
                                                                          380
                                                       370        Ser Arg
                                              Leu Glu Lys Ala Ser Ile Arg Tyr Ile TCG AGG
                            360         Val Leu Val Ala Phe CTC GAG AAG GCC TCC ATC AGA TAC ATT       1140
Lys Arg Lys Gln Thr Pro Ala Ser Asp Gly Glu Arg GTC GTC GCT TTC                          1120
AAA AGG AAA CAG ACT CCC GCC AGC GAT GGA GAA AGA      1100
                      1060                 1080
                                                                                         410
                                     390                            400                  Leu Phe
                            His Phe Ile Ser Gln Val Val Gln Asp Trp Lys Phe Val Ala Gln Val CTC TTT
His Val Lys Lys Glu CAC TTC ATC AGC CAG GTA GTG CAA GAC TGG AAA TTT GTG GCT CAA TTC CTG TGG CTG TTT
CAT GTG AAA AAG GAA                  1160            1180                1200             1220
        1140

420                430
                                     Ile Leu Ile Phe Ile Pro Ala Leu Lys Met Trp Ile His Arg Phe His
Leu Ile Ala Ser Val Leu Gly Ser CTG ATT TTT ATT CCA GCC TTG AAG ATG TGG ATA CAT CGT TTC CAC TAG GAGCCACTCTCTGGACCCA
CTG ATA GCT TCT GTG TTG GGT TCC                   1280                                         1320
            1240            1260                                               1300

TTTAGAGACATACATAGAGACAATCCCACCTTAGGACTGACAGCGGCTGGCATGCTGACAGGAAGACAGAGCCATGCAATCGTAGTGGTGCCCTTGTCTTGTCCTGGGAGCTTTCTGTG
                       1340                  1360                1380                  1400                  1420                 1440

AATGCAGGGCACTGAGAGAATGTGGGTTTGAGTTAGTGAGATGGTAGTGGCTGCTCCATTAGAGACGTCTCCAATTTGGAGACGTAGTTGGGCAATTGTATATGTTATGTGGAGTTCCTGAAC
                       1460                  1480                1500                  1520                  1540                 1560

TACTCCCTCTGCTCATCCTGAACGCACTGGGCACTGGGCTATTCTCTAGCAGTGCGTGAACGCATTTGACAATAGTTCAGGAATTACGCAGTACAACTCTCCACACAGG
                       1580                  1600                1620                  1640                  1660                 1680

TCAAATTGCCACTTGTCAACGAGTGTCCCACAAATAGGGTCATTGAAGATGACCTTGAATGGCTATGACAGTTCTCAAGGCAGTGTTACTGAAGTTGCTCACTGACCTGCGAAC
                       1700                  1720                1740                  1760                  1780                 1800

TTTTCGAATGCAGGTAGGAACTCGGGTGATTTCTAGCTTGCTGTAAGGTTCATCAAAATAACTACCCCAGAAAAACAGCCATTCGCTAGTAGAACTGTATTATTCACACACATCTC
                       1820                  1840                1860                  1880                  1900

TTTTTTTTCCC........3'
   1930
```

```
                                                                340                                  350                                  360
Val Arg Val Pro His Pro Ser Gln Leu His Leu Ala Thr Ala Asp Thr Ala Ala Thr Ser Ala Leu Gly Pro Thr Ser Pro Ser Asn Leu
GTC AGG GTC CCT CAT CCC AGC CAG CTG CAC TTG GCC ACA GCT GAT ACT GCA GCC ACC TCT GCC TTA GGC CCC ACC AGC CCA TCC AAC CTC
                   1020                                      1040                                   1060                                  1080

370                                  380                                  390
Tyr Gly Ser Ser Met Tyr Phe Val Asn Pro Val Pro Ala Ala Pro Lys Ser Ala Val Ser Ser His Thr Ala Gly Leu Pro Arg Asp Ala
TAT GGG AGT TCC ATG TAC TTT GTG AAC CCT GTC CCT GCC GCT CCT AAG TCT GCA GTC AGC TCC CAC ACA GCA GGC CTC CCC AGG GAT GCC
         1100                                    1120                                 1140                                 1160

400                                  410                                  420
Arg Leu Arg Ser Ser Gly Arg Phe Arg Glu Asp Leu Gln Glu Ala Leu Glu Gly Val Ser Phe Ile Ala Gln His Leu Glu Ser Asp Asp
CGT CTG AGG TCC TCC GGG AGG TTC CGG GAA GAT CTA CAG GAA GCA TTA GAG GGT GTC AGC TTC ATC GCC CAG CAT CTG GAG AGC GAT GAC
   1180                               1200                                  1220                                  1240                            1260

430                                  440
Arg Asp Gln Ser                                Val Ile Glu Asp Trp Lys Phe Val Ala Met Val Val Asp Arg Leu Phe Leu Trp
CGA GAT CAA AGT gtagtcactg...          ...ttgtctgcag GTC ATC GAG GAC TGG AAG TTC GTC GCG ATG GTT GTT GAC CGC CTG TTC TGG
      1280                                           1300                                   1320

450                                  460                                  470
Val Phe Val Phe Val Cys Ile Leu Gly Thr Met Gly Leu Phe Leu Pro Pro Leu Phe Gln Ile His Ala Pro Ser Lys Asp Ser *
GTG TTC GTG TTT GTG TGT ATT CTG GGC ACC ATG GGG CTC TTC CTG CCA CCC CTT TTC CAG ATC CAC GCA CCC TCC AAG GAC TCC TAG GCT
      1340                                  1360                                  1380                                  1400                              1420

ACCCGGCNTGTCTCGGGNNCCGGAAGTAGTGAGATGAGATATGAGAAGCGGTGGGAAGCAGGGCCGTGTCTCTTNGGGCTACCCGGCCTGTCTGCTCGGGCCCCGGGAAGTAGTGAGATGATGA
                                1440                                     1460                                    1480                                    1500                                  1520

GAAGCGGTGGGAAGCAGGGCCGTGTCTTCGG...3'
                  1540
```

FIG. 24C

```
CGTTGCTCGGCCCCTCGGGGTCCGGAGTTATCCGGAGGCCCGTCGCGGGGCGATGGCGGTGCGGGGTCCGGGCGGGCCGGTGCGGCTGCTCTTG
-180                    -160                    -140                    -120                    -100
```

```
                                        -10                                                    -1 1
Arg Gly Thr Pro Gly Leu Pro Glu Leu Ser Ser Ala Ala Lys
CGG ACC CCG GGA TTG CCT GAA CTA TCC TCT GCT GCC AAA
                                                        1
```

Met Val Gln Leu Leu Ala Gly Arg Trp Arg Pro Thr Gly Ala Arg Arg Gly Leu Pro Glu Leu Ser Ser Ala Ala Lys
ATG GTG CAG CTG CTG GCA GGG CGC TGG CGG CCG ACC GGG GCG CGG CGG GGA TTG CCT GAA CTA TCC TCT GCT GCC AAA
-80                    -60                    -40                    -20                    -1 1

20                              30
His Glu Asp Ser Leu Phe Arg Asp Leu Phe Glu Asp Tyr Glu Arg Trp Val Arg Pro Val Glu His Leu Ser Asp Lys Ile Lys
CAT GAA GAC AGC TTG TTT AGG GAT TTA TTT GAA GAT TAC GAA AGG TGG GTT CGT CCT GTG GAA CAC CTG AGC GAC AAG ATA AAA
                        20                              40                              60

40                              50                                      60
Phe Gly Leu Ala Ile Ser Gln Leu Val Asp Val Asp Glu Lys Asn Gln Leu Met Thr Thr Asn Val Trp Leu Lys Gln Glu Ile Asp
TTT GGC CTT GCG ATA TCT CAG GAT GTG GAT GAG AAA AAC CAG CTG ATG ACG AAC GTC TTG AAG CAG GAA ATA GAT
100                     120                     140                     160                     180

70                              80                              90
Val Lys Leu Arg Trp Asn Pro Asp Tyr Gly Gly Ile Ile Lys Ile Ile Arg Pro Ser Asp Ser Leu Trp Ile Pro Asp Ile Val Leu
GTG AAA TTG AGA TGG AAT CCT GAT TAT GGT GGG ATA ATT AAG ATT ATA CGT CCT TCG GAC TCC CTG TGG ATC CCA GAC ATC GTT TTG
        200                     220                     240                     260

100                             110                             120
Phe Asp Asn Ala Asp Gly Arg Phe Glu Gly Ala Ser Thr Lys Thr Val Val Arg Tyr Asn Gly Thr Val Thr Trp Thr Pro Ala Asn
TTC GAT AAT GCA GAT GGA CGA CGT GAA GGG GCC AGC ACG AAA ACA GTT GTC AGG TAC AAC GGC ACT GTC ACG TGG ACG CCA GCA AAC
280                     300                     320                     340                     360

140                             150
Tyr Lys Ser Ser Cys Thr Ile Asp Val Thr Phe Phe Pro Phe Asp Leu Gln Asn Cys Ser Met Lys Phe Gly Ser Trp Tyr Asp Gly
TAC AAA AGT TCT TGC ACC ATC GAC GTT ACC TTT TTC CCG TTT GAT CTC CAA AAT TGT TCC ATG AAA TTC GGC TCG TAC GAT GGA
        380                     400                     420                     440

160                             170                             180
Ser Gln Val Asp Ile Ile Leu Glu Glu Gln Asp Val Asp Arg Asp Thr Phe Phe Asp Asn Gly Glu Trp Glu Ile Met Met Gly
TCC CAG GTT GAT ATC ATC CTA GAG GAA CAA GAT GTC GAC AGA GAC ACA TTT TTC GAC AAT GGA GAG TGG GAA ATC ATG AGC GGG
460                     480                     500                     520                     540

190                             200                                      210
Ser Lys Gly Asn Arg Thr Asp Ser Cys Cys Trp Tyr Pro Tyr Ile Thr Tyr Ser Phe Val Ile Lys Arg Leu Pro Leu Phe Thr Leu
AGC AAG GGG AAC CGG ACG GAC AGT TGC TGC TGG TAC CCC TAC ATC ACG TAC TCC TTT GTG ATT AAG CGG CTG CCT CTC TTC ACC TTG
                560                     580                     600                     620
```

FIG. 25A

```
Phe Leu Ile Ile Pro Cys Ile Gly Leu Ser Phe Leu Thr Val Val Phe Tyr Leu Pro Ser Asn Glu Gly Lys Ile Ser Leu Cys
TTT CTT ATT ATC CCC TGC ATT GGG TCA TTT CTG ACT GTG GTT TTC TAT CTC CCT TCA AAC GAG GGT GAA AAG ATT AGC CTC TGC
        640              220              230                      700              240                  720

Thr Ser Val Leu Val Ser Leu Leu Thr Val Phe Leu Leu Val Ile Glu Glu Pro Ser Ser Lys Val Ile Pro Leu Ile Gly Glu
ACC TCA GTG CTC GTC TCT CTG ACT GTG TTC CTT TTG GTA ATC GAA GAG CCA TCA TCT TCC AAA GTC ATA CCC CTG ATT GGG GAG
            740              250              260              780              270                  800

Tyr Leu Val Phe Thr Met Ile Phe Val Thr Ile Met Val Thr Val Pro Ser Ile Asn Ile His His Arg Ser Ser Thr His
TAC TTG GTG TTC ACC ATG ATT TTC GTG ACC CTA ATT ATG GTG ACT GTC CCA TCC ATC AAC ATC CAC CAC CGG TCT TCC ACA CAC
        820              280              290              860              300                      900

Asn Ala Met Ala Pro Trp Val Arg Lys Ile Phe Leu His Lys Leu Cys Met Arg Ser His Ala Asp Arg Tyr Ile Arg Phe Thr
AAC GCT ATG GCG CCC TGG GTT CGT AAG ATA TTT CTC CAC AAG CTC TGC ATG AGA AGT CAT GCG GAT AGG TAC ATC CGC TTC ACT
            920              310              320              980              330                1080

Gln Arg Glu Ala Glu Gly Ser Arg Gly Ala Ala Leu Asp Cys Ile Arg Tyr Ile Thr Arg His
CAG AGA GAA GCC GAG AGT GCT GGA GCC GCA CTC GAT TGC ATT CGC TAC ATC ACG AGG CAC
1000             340              350              1060             360

Val Val Lys Glu Asn Asp Val Val Glu Val Val Asp Trp Lys Phe Ile Ala Gln Val Leu Asp Arg Met Phe Leu Trp Phe Leu
GTC GTG AAA GAG AAC GAC GTC GAG GTT GTT GAA GAT TGG AAA TTC ATA GCC CAA GTC CTT GAT CGG ATG TTT TTG TGG ACG TTT CTT
        1100             370              1120             380                      1160             390

Leu Val Ser Ile Ile Gly Leu Gly Leu Phe Val Pro Val Ile Tyr Lys Ala Asn Ile Ile Val Pro Val His Ile Gly Asn Thr
CTG GTG TCA ATC ATT GGG CTT TTA GTT CCT GTT ATT TAT AAA TGG GCC AAT ATA ATA GTC CCA CAC ATT GGA AAC ACA
1180             400              1200             410              1240             420              1260
```

FIG. 25B

```
Ile Lys *
ATT AAG TGA AACCAAGAAATTACCCTGTGGAATTTAGTGAGCAGTCATGCAGCTCTTAGGACATGTATGCTGTTATGGAAATGTGAAGGTAGTTACAATTTGACATAGGCTATAACA
    1280                 1300                 1320                 1340                 1360                 1380
GATTAGCAATTTCTAACATTGGCTTAATGTTGTCCATTAGAACTGCAGTAATAACCTCAAATAGCAACAACACATTGTCTGCTGCACTAGTGAAGGCCTAGTGCATCCTGGCAA
       1400                 1420                 1440                 1460                 1480                 1500
ACCCTACCAATTGCAACCAATGATGAAGGCCATCCTTGGAGTGCTGGAAAACTCAACTGTATTTGAAGACTATTAAAACTCCCCCAAATTTAGTAGGAACATATATGTGTGGTT
       1520                 1540                 1560                 1580                 1600                 1620
TTGAATTTCAGAATGGGTCTTTGGGTCTTGTTAAATTGTCTGGGCTAGCACAAAACCTCCTGAGTAGCTGGGACCATGGTGTGCTCCACTTGCCCTGTCTGTATTCACAGATATA
       1640                 1660                 1680                 1700                 1720
AAATACATCATTATTTATAGGAGGTAGGCCCATTACTTGGTTTAATAATAACTTAGGTCAGTTTAATTATAACCTTATGTCAGCTAATGTTCTATGCTGTGAAGAGACATC
       1760                 1780                 1800                 1820                 1840
ATGACCATCAACTCTTATAAAGAAACATTTCATCAGTGCTGGCTTACAGTTTTTGAGGTTTAGCCAATTATCACAGTGAAAGCATGATAGCATCCAGGTAGACATAATGCTGGATCC
       1880                 1900                 1920                 1940                 1960
AGGAGTTCTCTACATCTGATCAGCAGGAAGCAGGAAGAGAGAGCCACTGGCTTGAGACATCTGAAACCTCAAAGCCCACCTCCAGTGACACACTTCCCCCAACAAGCC
       2000                 2020                 2040                 2060                 2080
ACACCTCCTAATAGTGCCACTTGCTGGTGATCAAGCATTCAGTCTACGAGAGCCATTCCTATCCAAACCACACTTAATAGGATGCTATTCTTTACTGACATTTTAATAAG
       2100                 2120                 2140                 2160                 2180                 2200
CGACAAATGGTAACTAGAAACATCGTAGGCCACTTACTTCTTTATATGGTAATATGGATTGGCTTTATATAACTAGTTTTACAGCCTATCTGAAACATGTAACAGGCAACTCTG
       2220                 2240                 2260                 2280                 2300                 2320
CAGACACATTCTTGTAATGACTTTATAATCCTGCAGTGCCATGTTCTGGTAATGACTTCAGTCTCGTCACACTCTCCGGTTAGTAGACATTTATGTACATCGCGTATCCCTG
       2340                 2360                 2380                 2400                 2420                 2440
ATTTCAGAGCAACTGTGCAGTTGCACCTGCACAGGTTCCCACCTCAACGGGATGCATGAATAATTCTGTGGAAAACCATTCTGAGCTGGATACGGTGCCTCATACCTGTCA
       2460                 2480                 2500                 2520                 2540                 2560
TGTCTACTTTCAGGAGGCAGAGGCAGGGAATTGCTGTGAGTTGTTGGTCAGCCTGGGTTACATATGAGACCCTGTCTCAGAAAAACAAACAAAACTTCCCCTGTCAGTTGATATAAG
       2580                 2600                 2620                 2640                 2660                 2680
CACACTGTCATATCCGAATTGGGGATCCTCTAGAGTCGACCTGCAGGCATGCAAGCTTGGCGTAATCATGGTCATAGCTGTTTCCTGTGAATTGTTATCCG
       2700                 2720                 2740                 2760                 2780
```

FIG. 25C

BETA2    MLACMAGHSNSMALFSFSLLWLCSGVLGTDTEERLVEHLLDPSRYNKLIRPATNGSELVTVQLMVSLAQLISVHEREQIMTTNVWLTQEWEDYRLTWKPEDFDNMKKV
BETA3    MTGFLRVFLVLSATLSGSWVTLTATAGLSSVAEHEDALLRHLFQGYQKWVRPVLNSSDIIKVFFGLKISQLVDVDEKNQLMTTNVWLKQEWTDQKLRWNPEEYGGINSI
BETA4           MRGTPLLLVSLFSLLQDGDCRLANAEEKLMDDLLNKTRYNNLIRPATSSSQLISRLELSLSQLISVNEREQIMTTSIWLKQEWTDYRLAWNSSCYEGVNIL
                ├─── SIGNAL PEPTIDE ───┤

BETA2    RLPSKHIWLPDVVLYNNADGMYEVSFYSNAVVSYDGSIFWLPPAIYKSACKIEVKHFPFDQQNCTMKFRSWTYDRTEIDLVLKSDVASLDDFTPSGEWDIIALPGRRNE
BETA3    KVPSESLWLPDIVLFENADGRFEGSLMTKAIVKSSGTVSWTPPASYKSSCTMDVTFFPFDRQNCSMKFGGSWTYDGTMVDLILINENVDRKDFFDNGEWEILNAKGMKGN
BETA4    RIPAKRVWLPDIVLYNNADGHYEVSVYTNVIVRSNGSIQWLPPAIYKSACKIEVKHFPFDQQNCTLKFRSWTYDHTEIDMVLKSATAIMDDFTPSGEWDIVALPGRRTV
                                              *

BETA2    NPDDS  TYVDITYDFIIRRKPLFYTINLIIPCVLITSLAILVFLLISKIVPPTSLDVPLVGKYLMFTMVLVTFSIVTSVCVLNVH
BETA3    RREGFYSPFVTYSFVLRRLPLFYTLFLIIPCLGLSFLTVLVFYLPSDEGEKLSLSTSVLVSLTVFLLVIEEIIPSSKVIPLIGEVLLFIMIFVTLSIIVTVFVINVH
BETA4    RPQDP  SYVDVTYDFIIKRKPLFYTINLIIPCVLITSLAILVFLLISKIVPPTSLDIPLIGKYLLFTMVLVTFSIVTTVCVLNVH
                ├──── MSR I ────┤                              ├──── MSR II ────┤                 ├──── MSR III ────┤

BETA2    HRSPTT  HTMAPWVKVVFLEKLPTLLFLQQPRHRCARQRLRLRRQREREGEAVFFREGPAADPCSCSVGPCSCG
BETA3    HRSSSTYHPMAPWVKRLFLQRLPRWLCMCKDPMDRFSFPDGKESDTAVRGKVSGKRKQTPASDGERVLVAFLEK
BETA4    HRSPST  HTMASWVKECFLHKLPTFLFMKRPGLEVSLVRVPHPSQLHLATADTAATSALGPTSPSNLYGSSMYFVNPVPAAPKSAVSSHTAG  LPRDRARLRS

BETA2           LREAVDGVRFIADHMRSEDDQSVREDWKYVAMVIDRLFLWIFVCVFGTVGMFLQPLFQNYTATTFLHPDHSAPSSK*
BETA3    ASESIRYISRHVKKEHFISQVVQDWKFVAQVLDRIFLWLFLIASVLGSILIFIPALKMWIHRFH*
BETA4    SGRFREDLQEALEGVSFIAQHLESDDRDQSVIEDWKFVAMVVDRLFLWVFVCVLGLFLWVFVFVCILGTMGLFLPPLFQIHAPSKDS*
                                            ├──── MSR IV ────┤

FIG.26

```
ALPHA2       MTLSHSALQFWTHLYLWCLLLVPAVLTQQGSHTHAEDRLFKHLFGGYNRWARPVPNTSDVVIRFGLSIAQLIDVEKNQMTTNVWLKQEWNDYKLRWDPAEF
ALPHA3            MGVLLPPPLSMLMLVLMLLPAASASEAEHRLFQYLFEDYNELIRPVANVSHPVIIQFEVSMSQLVKVDEVNQIMETNLWLKQIWNDYKLKWKPSDV
ALPHA4  MEIGGPAPPPLLLLLLGTGLLPASSHIETRAKALEERLLKRLFSGYNKMSRPVGNISDVVLRFGLSIAQLIDVDEKNQMTTNVVKQEWHDYKLRWDPGDY
ALPHA5          MVQLLAGRWRPTGARRGTAGGLPELSSAAKHEDSLFRDLFEDYERWVRPVEHLSDKIKIKFGLAISQLVDVDEKNQLMTTNVWLKQEWIDVKLRWNPDDY
                  SIGNAL PEPTIDE

ALPHA2  GNVTSLRVPSEMIWIPDIVLYNNADGEFAVTHMTKAHLFFTGTVHWVPPAIYKSSCSIDVTFFPFDQQNCKMKFGSWTYDKAKIDLEQMERTVDLKDYWESGEWAII
ALPHA3  QGVEFMRVPAEKIWKPDIVLYNNADGDFQVDDKTKALLKYTGEVTMIPPAIFKSSCKIDVTYFPFDYQNCTMKFGSWSYDKAKIDLVLIGSSMNLKDYWESGEWAII
ALPHA4  ENVTSIRIPSELIWRPDIVLYNNADGDFAVTHLTKAHLFYDGRVQWTPPAIYKSSCSIDVTFFPFDQQNCTMKFGSWTYDKAKIDLVSIHSRVDQLDFWESGEWVIV
ALPHA5  GGIKIIRVPSDSLWIPDIVLFDNADGRFEGAS  TKTVRYNGTVTWTQPANYKSSCTIDVTFFPFFDLQNCSMKFGSWTYDGSQVDIILEDQDVDRTDFFDNGEWEIM

ALPHA2  NATGTYNSKKYDCCAEIYPDVTYFVIRRLPLFYTINLIIPCLLISCLTVLVFYLPSECGEKITLCISVLLSLTVFLLITEIIPSTSLVIPLIGEYLFTMIFVTL
ALPHA3  KAPGYKHEIKYNCCEEIYQDITYSLYIRRLPLFYTINLIIPCLLISFLTVLVFYLPSDCGEKVTLCISVLLSLTVFLLVITETIPSTSLVIPLIGEYLLFTMIFVTL
ALPHA4  DAVGTYNTRKYECCAEIYPDITYAFIIRRLPLFYTINLIIPCLLISCLTVLVFYLPSECGEKVTLCICSVLLSLTVFLLLIITEIIPSTSLVIPLIGEYLFTMIFVTL
ALPHA5  SAMGSKGNRTDSCCW   YPYITYSFVIKRLPLFYTLFLIIPCIGLSFLTVVVFYLPSNEGEKISLCTSVLVSLTVFLLVIEEIIPSSKVIPLIGEYLVFTMIFVTL
                                                    MRS I                                  MRS II                MRS III

ALPHA2  SIVITVFLNVHHRSPSTHNMPN   WVRVALLGRVPRWLMMNRPLPPMELHGSPDLKLSPSYHWLETNMDAGEREETEEEEEEDENICVCAGLPDSSMGVLYGHGGL
ALPHA3  SIVITVFLNVHYRTPTTHTMPT   WVKAVFLNLLPRVMFMTRPTSGEGDTPKTRIFYGAELSNLNCFSRADSKSCKEGYPCQDGTCGYCHRRVKISNFSANLITRSS
ALPHA4  SIVITVFLNVHHRSPRTHTMPA   WVRRVFLDIVPRLLFMKRPSVVKDNCRRLIESMHKMANAPRFWPEPVGEPGILSDICNQGLSPAPTFCNPTDTAVETQPTCRS
ALPHA5  SIMVTVFAINIHHRSSSTHNAMAPWVRKIFLHKLPKLLCMRSHADRYFTQREEAESGAGPKSRNT
                                                                                                            MRS IV

ALPHA2  HGGLHLRAMEPETKTPSQA
ALPHA3  SESVNAVL
ALPHA4  PPLEVPDLKTSEVEKASPCPSPGSCPPPKSSSGAPMLIKARSLSVQHVPSSQEAAEDGIRCRSRSIQYCVSQDGAASLADSKPTSSPTSLKARPSQLPVSDQASPCK

ALPHA2        SEILLSPQIQKALEGVHYIADRLRSEDADSSVKEDWKYVAMVVDRIFLWLFIIVCFLGTIGLFLPPFLAGMI*
ALPHA3        SLSALSPEIKEAIQSVKYIAENMKAQNVAKEIQDDWKYVAMVIDRIFLWVFILVCILGTAGLFLQPLMARDDT*
ALPHA4  CTCKEPSPVSPVTVLKAGGTKAPPQHLPLSPALTRAVEGVQYIADHLKAEDTDFSVKEDWKYVAMVIDRIFLWMFIIVCLLGTVGLFLPPWLAGMI*
ALPHA5      LEAALDCIRYITRHVVKENDVREVVEDWKFIAQVLDRMFLWTFLLVSIIGTGLFVPVFINGPI*
                                                                 MSR IV
```

FIG. 27

NEURONAL NICOTINIC ACETYLCHOLIHNE RECEPTOR COMPOSITIONS

This application is a divisional of U.S. Ser. No. 07/898,185, filed Jun. 12, 1992, now U.S. Pat. No. 5,371,188, which is a continuation of U.S. Ser. No. 07/321,384, filed Mar. 14, 1989, now abandoned, which was a continuation-in-part of U.S. Ser. No. 07/170,295, filed Mar. 18, 1988, now abandoned.

This invention was made with government support under several grants from the National Institutes of Health and the United States Army.

FIELD OF THE INVENTION

The present invention relates generally to neuronal nicotinic acetylcholine receptor genes and proteins. More particularly, the invention relates to a family of novel mammalian neuronal nicotinic acetylcholine receptor genes and proteins. The receptor proteins are comprised of agonist binding subunits and non-agonist binding subunits. Agonist binding subunits of the invention include the neuronal agonist subunits referred to herein as alpha2, alpha3, alpha4, and alpha5; non-agonist binding subunits include beta2, beta3 and beta4. The invention further relates to novel DNA sequences that encode these receptor protein subunits.

BACKGROUND OF THE INVENTION

Most theories on how the nervous system functions depend heavily on the existence and properties of cell to cell contact known as synapses. For this reason, the study of synapses has been a focal point for neuroscience research for many decades.

Because of its accessibility to biochemical and electrophysiological techniques, and because of its elegant, well defined structure, the neuromuscular synapse (also known as the neuromuscular junction), which occurs at the point of nerve to muscle contact, is one of the most studied and best understood synapses. At the neuromuscular junction, the nerve cell releases a chemical neurotransmitter, acetylcholine, which binds to nicotinic acetylcholine receptor proteins located on post-synaptic muscle cells. The binding of acetylcholine results in a conformational change in the nicotinic acetylcholine receptor protein. This change is manifested by the opening of a transmembrane channel in the receptor which is permeable to cations. The resulting influx of cations depolarizes the muscle and ultimately leads to muscle contraction.

Biological and structural studies have shown that the nicotinic acetylcholine receptor in muscle is a glycoprotein composed of five subunits with the stoichiometry $\alpha\alpha\beta\lambda\delta$ (alpha-alpha-beta-gamma-delta). From these same studies, it is known that each of the subunits has a mass of about 50–60 kilodaltons and is encoded by a separate gene. In vitro reconstitution experiments have shown that this $\alpha\alpha\beta\lambda\delta$ complex is a functional receptor containing both ligand binding sites and a ligand-gated transmembrane channel. (For a review, see Karlin, et al., 1986 and McCarthy, et al., 1986.)

It is now known that a variety of neurotransmitters and neurotransmitter receptors exist in the central and peripheral nervous systems. Despite this knowledge, there is still little understanding of the diversity of receptors for a particular neurotransmitter, or of how this diversity might generate different responses to a given neurotransmitter, or to other modulating ligands, in different regions of the brain. On a larger scale, there is little appreciation of how the use of a particular synapse makes it more or less efficient, or how long-term changes in neuronal circuits might be accomplished by the modification of synapses.

An understanding of the molecular mechanisms involved in neurotransmission in the central nervous system is limited by the complexity of the system. The cells are small, have extensive processes, and often have thousands of synapses deriving from inputs from many different parts of the brain. In addition, the actual number of neurotransmitter receptors is low, making their purification difficult, even under the best of circumstances. Consequently, neither cellular nor biochemical approaches to studying neurotransmission in the central nervous system has been particularly fruitful. This is unfortunate because it is quite probable that the treatment of dementia, Alzheimer's disease and other forms of mental illness will involve modification of synaptic transmission with specific drugs.

Nicotinic acetylcholine receptors found at the vertebrate neuromuscular junction, in vertebrate sympathetic ganglia and in the vertebrate central nervous system can be distinguished pharmacologically on the basis of ligands that open or block the ion channel. For example, the elapid $\alpha$-neurotoxins that block activation of nicotinic acetlycholine receptors at the neuromuscular junction do not block activation of neuronal nicotinic acetylcholine receptors found on several different cell lines.

To gain access to the neuronal acetylcholine receptors, traditional biochemical and neurophysiological methods have been abandoned in favor of the newer methods of molecular biology. More specifically, using molecular cloning techniques, our group first isolated complementary DNA clones encoding the acetylcholine receptor expressed in the Torpedo fish electric organ, a highly enriched source of receptor (see Ballivet, et al., 1983 and Patrick, et al., 1983) were isolated. The cDNA clones isolated from the fish electric organ were then used in nucleic acid hybridization experiments to obtain cDNA and genomic clones for the subunits of the acetylcholine receptor expressed in mouse skeletal muscle.

The availability of cDNA clones encoding the muscle nicotinic receptor made it possible to extend these studies in the important direction of neuronal receptors. More specifically, based on the assumption that the neuronal nicotinic receptors are evolutionarily related to the muscle receptors, and that this relationship will be reflected at the genetic level by nucleotide sequence homology, the cDNA clones encoding the muscle nicotinic receptor were used to screen rat and mouse cDNA and genomic libraries for related neuronal mRNAs or genes. This method has resulted in the isolation of several neuronal cDNA clones that have significant sequence homology with the muscle acetylcholine clones. Clones, which encode the neuronal nicotinic acetylcholine receptor subunit proteins referred to as alpha2, alpha3, alpha4, alpha5, and beta2, beta3 and beta4, are disclosed in the present specification.

These neuronal clones encode a family of acetylcholine receptors having unique pharmacological properties. In this regard, the realization that the nicotinic acetylcholine receptors are much more diverse than previously expected offers an opportunity for a level of pharmaceutical intervention and a chance to design new drugs that affect specific receptor subunits. Such subtypes make it possible to observe the effect of a drug substance on a particular subtype. Information derived from these observations will allow the development of new drugs that are more specific, and therefore have fewer unwanted side effects.

In addition, the availability of these neuronal receptors makes it possible to perform initial in vitro screening of the drug substance. While it is true that the drug eventually has to work in the whole animal, it is probable that useful drugs are being missed because conventional screening is limited to average composite effects. Consequently, the ability to screen drug substances in vitro on a specific receptor subtype(s) is likely to be more informative than merely screening the drug substance in whole animals.

Both the receptor subunit genes and proteins of the present invention can be used for drug design and screening. For example, the cDNA clones encoding the alpha2 through alpha5 and beta2 through beta4 receptor subunits can be transcribed in vitro to produce mRNA. This mRNA, either from a single subunit clone or from a combination of clones, can then be injected into oocytes where the mRNA will direct the synthesis of the receptor molecule(s). Alternatively, the clones may be placed downstream from appropriate gene regulatory elements and inserted into the genome of eukaryotic cells. This will result in transformed cell lines expressing a specific receptor subtype, or specific combinations of subtypes. The derived cell lines can then be produced in quantity for reproducible quantitative analysis of the effects of drugs on receptor function.

PUBLICATIONS

Some of the information disclosed in this specification has been published:

The study disclosed in Experimental Section I was published Mar. 27, 1987 as: Goldman, D., Deneris, E., Luyten, W., Kochhar, A., Patrick, J., and Heinemann, S. (1987). Members of a Nicotinic Acetylcholine Receptor Gene Family Are Expressed in Different Regions of the Mammalian Central Nervous System. *Cell* 48, 965–973.

The study disclosed in Experimental Section II was published Mar. 18, 1988 as: Deneris, E. S., Connolly, J., Boulter, J., Wada, E., Wada, K., Swanson, L., Patrick, J., and Heinemann, S. (1988). Primary Structure and Expression of Beta 2: A Novel Subunit of Neuronal Nicotinic Acetylcholine Receptors. *Neuron,* 1, 45–54.

The study disclosed in Experimental Section III was published in November, 1987 as: Boulter, J., Connolly, J., Deneris, E., Goldman, D., Heinemann, S., and Patrick, J. (1987). Functional Expression of Two Neuronal Nicotinic Acetylcholine Receptors from cDNA Clones Identifies a Gene Family. *Proc. Natl. Acad. Sci., USA* 84, 7763–7767.

The study disclosed in Experimental Section IV was published as: Wada, K., Ballivet, M., Boulter, J., Connolly, J., Wada, E., Deneris, E. S., Swanson, L. W., Heinemann, S., and Patrick, J. (1988). Isolation and Functional Expression of a Gene and cDNA Encoding the Alpha2 Subunit of a Rat Neuronal Nicotinic Acetylcholine Receptor. *Science,* 330–334.

BRIEF DESCRIPTION OF THE DRAWINGS

The following is a brief description of the drawings. More detailed descriptions are found in the Experimental Sections of this specification.

The drawings comprise 29 Figures, of which:

Experimental Section I

Figure 1:
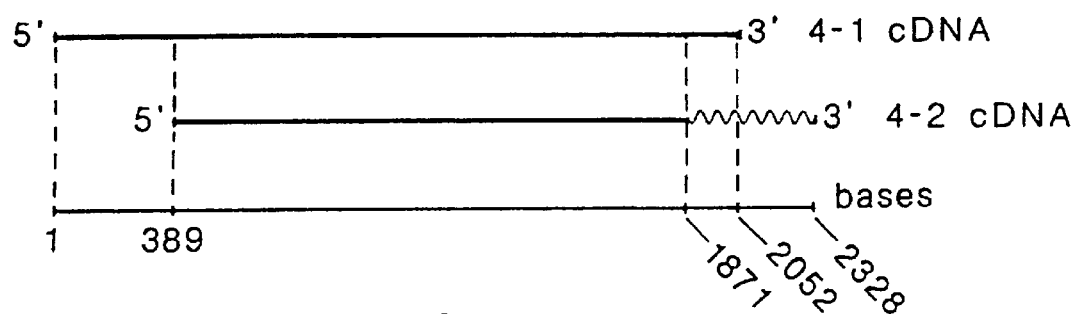

FIG. 1 is a schematic drawing that illustrates the relationship of neuronal nicotinic acetylcholine receptor alpha subunit cDNA clones 4.1 and 4.2 to each other.

FIGS. 2A to 2F comprises schematic drawings that show the nucleotide and predicted primary protein sequence of cDNA clones for neuronal nicotinic acetylcholine receptor alpha subunits 4.1 and 4.2.

FIGS. 3A and 3B comprises a schematic drawing that shows the alignment of deduced amino acid sequences for acetylcholine receptor alpha subunits from the mouse muscle cell line, BC3H-1 (alpha1, clone BMA407) (Boulter, et al., 1985), the rat neuronal cell line, PC12 (alpha3, clone PCA48) (Boulter, et al., 1986) and the rat brain (alpha4, clone 4.2).

FIG. 4 (A & B) is composed of two photographs of sectioned brain tissue that was used to map brain areas expressing RNA homologous to clones alpha 4.1 and alpha 4.2.

FIG. 5 (A & B) is composed of two photographs of sectioned brain tissue used to compare alpha3 and alpha4 gene expression in rat brains by in situ hybridization.

Figure 6A:
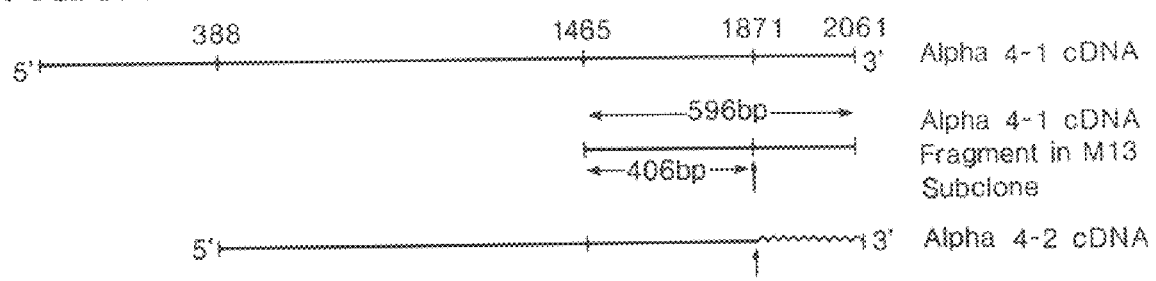
Figure 6B:
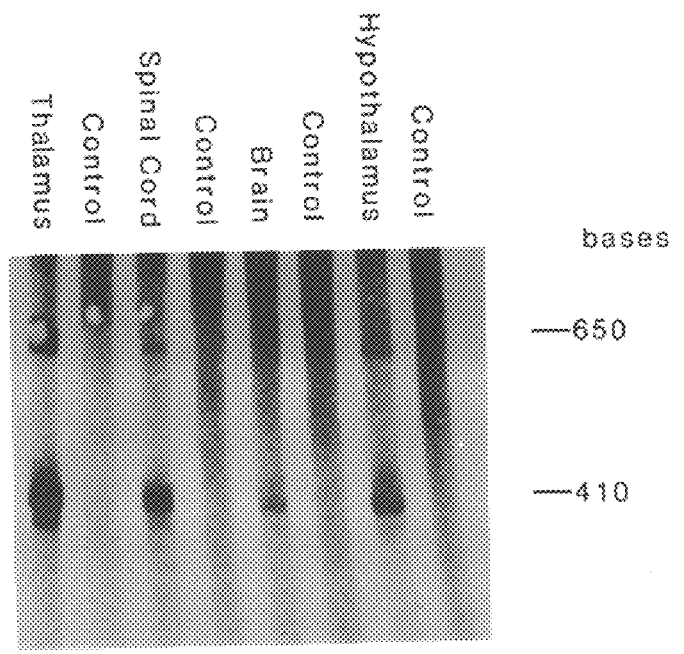

FIG. 6 (A & B) is composed of a drawing and a photograph, respectively, that illustrate the effects of a S1 nuclease protection experiment on cDNA from alpha clone 4.1.

Experimental Section II

FIGS. 7A to 7D is composed of two sets of drawings: 7A shows the relationship and lengths of the beta2 clones; 7B to 7D show the nucleotide sequence of the beta2 cDNAs and the deduced amino acid sequence.

FIG. 8 is a schematic drawing that shows the amino acid alignment of the beta2 subunit with the mouse muscle and rat neuronal alpha subunits.

Figure 9A:
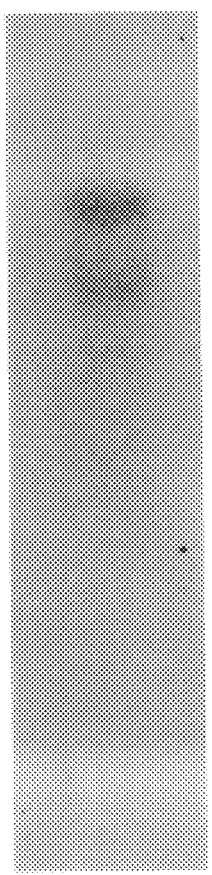

FIG. 9 (A & B) is composed of two photographs that show Northern blot analysis (A) of poly(A)$^+$ RNA isolated from PC12 cells and (B) Poly(A)$^+$ RNA isolated from an area of the thalamus that includes the medial habenular nucleus (lane 1) and from the spinal cord (lane 2).

FIG. 10 (A & B) is composed of two photographs of brain tissue sections that illustrate in situ hybridization analyses using beta2 sense and antisense RNA strands.

Experimental Section III

FIG. 11 is a schematic drawing that shows a comparison of amino acid sequences of the mouse muscle (alpha1) and two neuronal (alpha3 and alpha4) nicotinic acetylcholine receptor alpha subunits.

Figure 12:
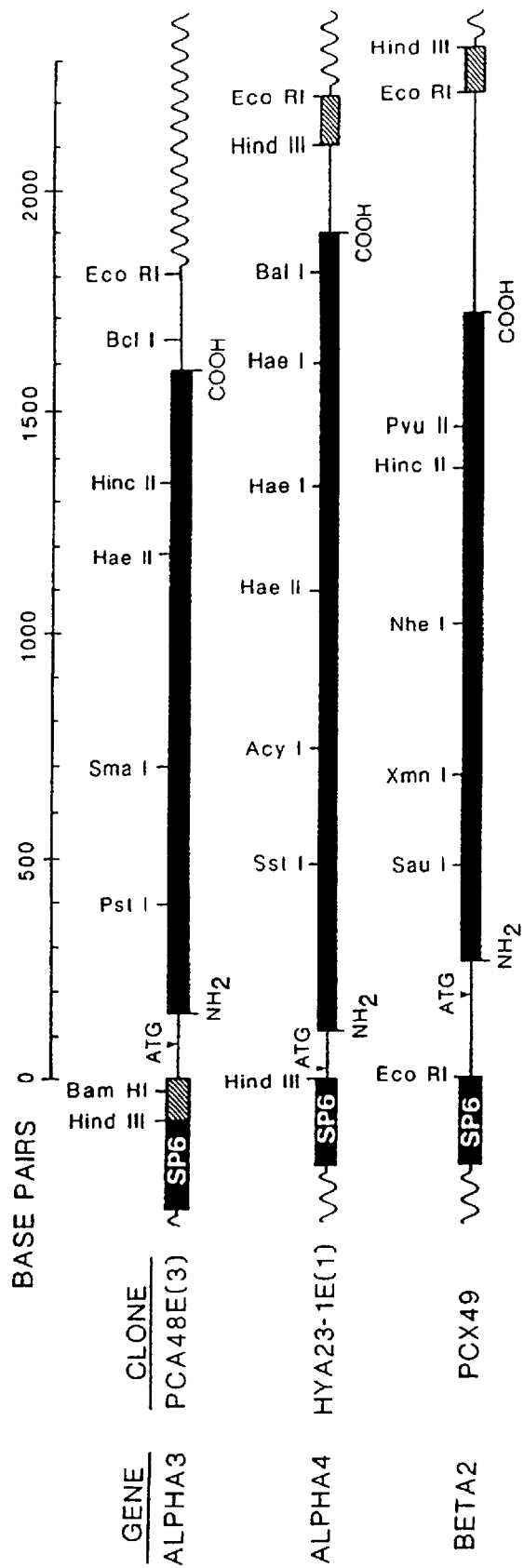

FIG. 12 is a schematic drawing showing restriction maps of the expressible cDNA clones encoding neuronal alpha subunits derived from the alpha3 gene (PCA48(E)3) and the alpha4 gene (HYA23-1(E)1) and the clone PCX49 derived from the beta2 gene.

FIG. 13 (A, B & C) is composed of three drawings that show voltage traces obtained from 5 different *Xenopus* oocytes injected with RNA derived from the neuronal alpha and beta genes.

FIG. 14 (A, B, C & D) is composed of four drawings that show voltage tracings which illustrate the effect of two different neurotoxins on the activation by acetylcholine of two neuronal nicotinic acetylcholine receptor subtypes.

Experimental Section IV

FIGS. 15A to 15F is composed of three schematic drawings: 15A and 15B respectively show the restriction enzyme maps of rat genomic DNA and cDNA encoding the alpha2 protein; 15C to 15F show the nucleotide sequences of the alpha2 genomic DNA with the deduced amino acid sequence.

FIG. 16 is a schematic drawing which shows alignment of the amino acid sequences of mouse muscle alpha subunit (alpha1) and rat neuronal alpha subunits (alpha2, alpha3 and alpha4).

FIG. 17 (A & B) is composed of two photographs that show a comparison of the distribution of alpha2, alpha3 and alpha4 transcripts by in situ hybridization histochemistry.

Experimental Section V

FIG. 18 (A & B) is composed of two schematic drawings that relate to the beta3 cDNA clones. (A) shows the relationship and partial restriction endonuclease map of cDNA clones τ ESD-7, τ HYP630, τ HYP504, and τ 51. (B) illustrates the expression construct, pESD76, in plasmid vector pSP64.

FIGS. 19A to 19C is a schematic drawing that shows the nucleotide sequence and deduced primary structure of the beta3 protein.

FIG. 20 is a schematic drawing that shows alignment of the amino acid sequences of the beta3 subunit with neuronal nAChR subunits rat beta2, alpha2, alpha3 and alpha4-1 subunits.

Figure 21:
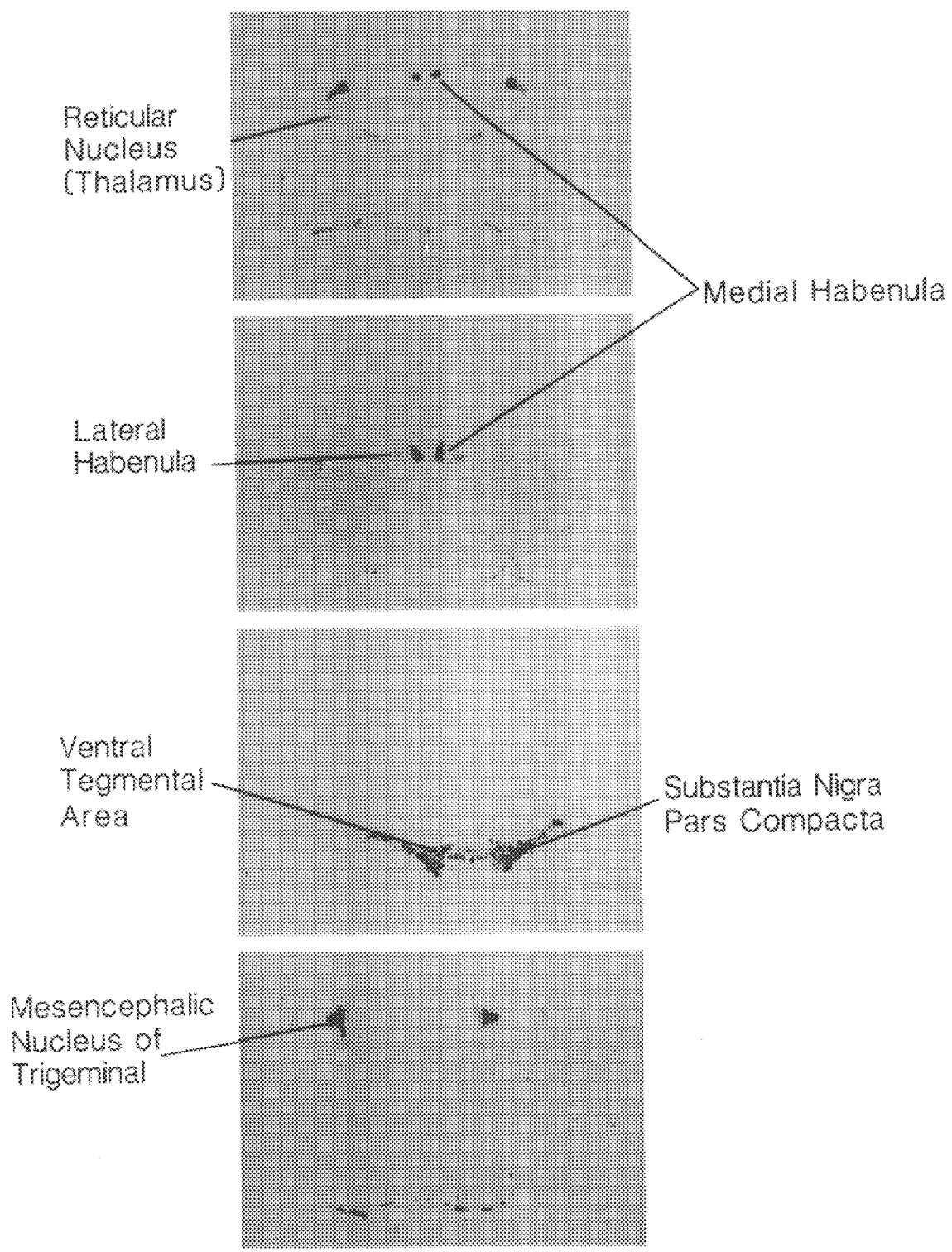

FIG. 21 is a photograph that shows localization of beta3 transcripts in the rat forebrain and midbrain by in situ hybridization histochemistry.

Figure 22:
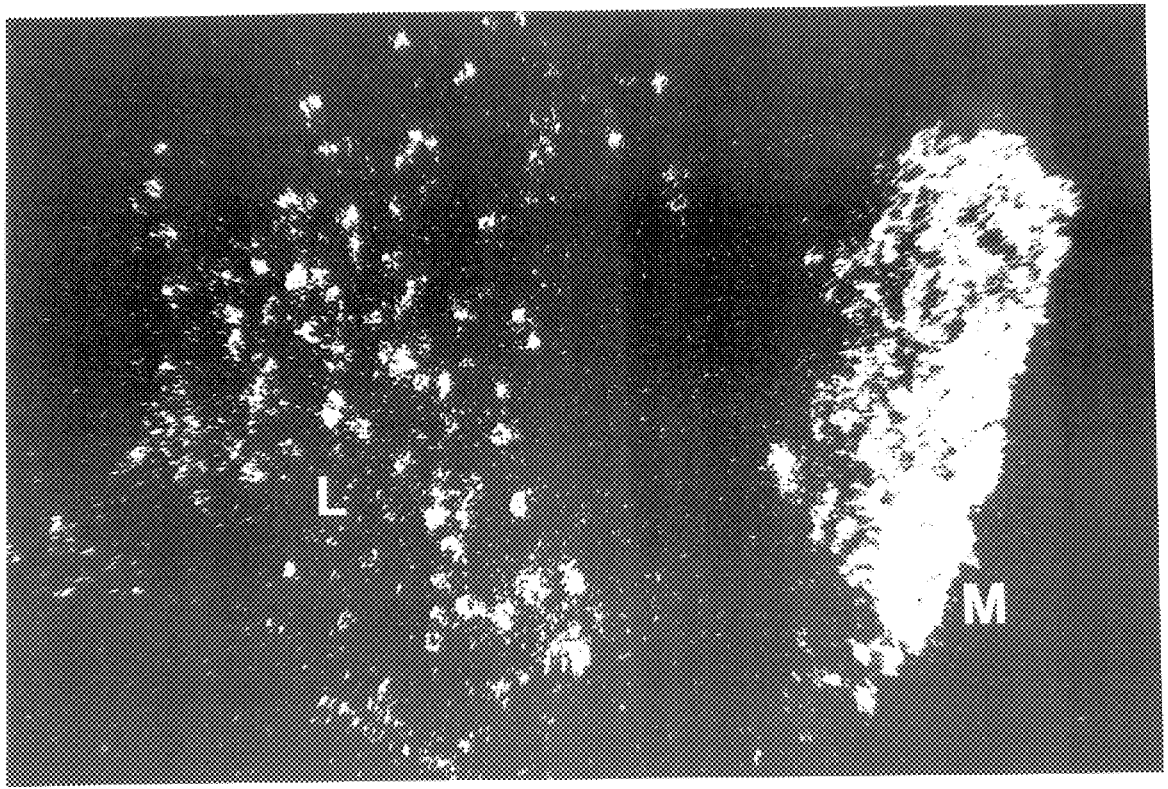

FIG. 22 is a darkfield photomicrograph of the habenular nuclei from rat brain.

Experimental Section VI

Figure 23:
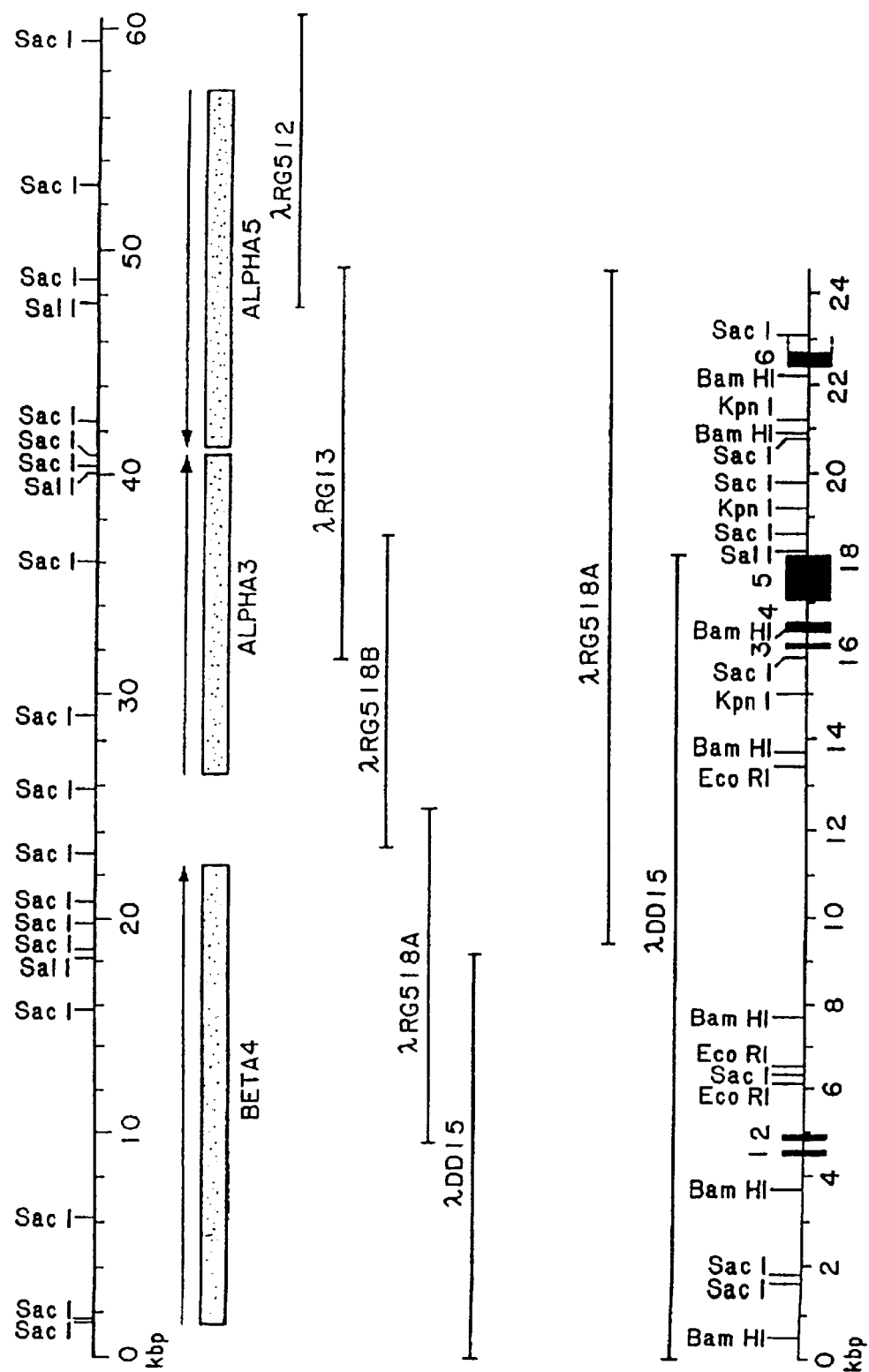

FIG. 23 is a schematic drawing that shows a partial restriction endonuclease map and orientation of transcription units for rat genomic clones encoding members of the nicotinic acetylcholine receptor-related gene family.

FIGS. 24A to 24C is a schematic drawing that shows the nucleotide sequence and deduced primary structure of the beta4 gene.

FIGS. 25A to 25C is a schematic drawing that shows the nucleotide sequence and deduced primary structure of the alpha5 gene.

FIG. 26 is a schematic drawing that shows a comparison of the aligned amino acid sequences for the beta2, beta3 and beta4 genes.

FIG. 27 is a schematic drawing that shows a comparison of the aligned amino acid sequences for the alpha2, alpha3, alpha4 and alpha5 genes. Sequences were aligned as in FIG. 26.

Figure 28:
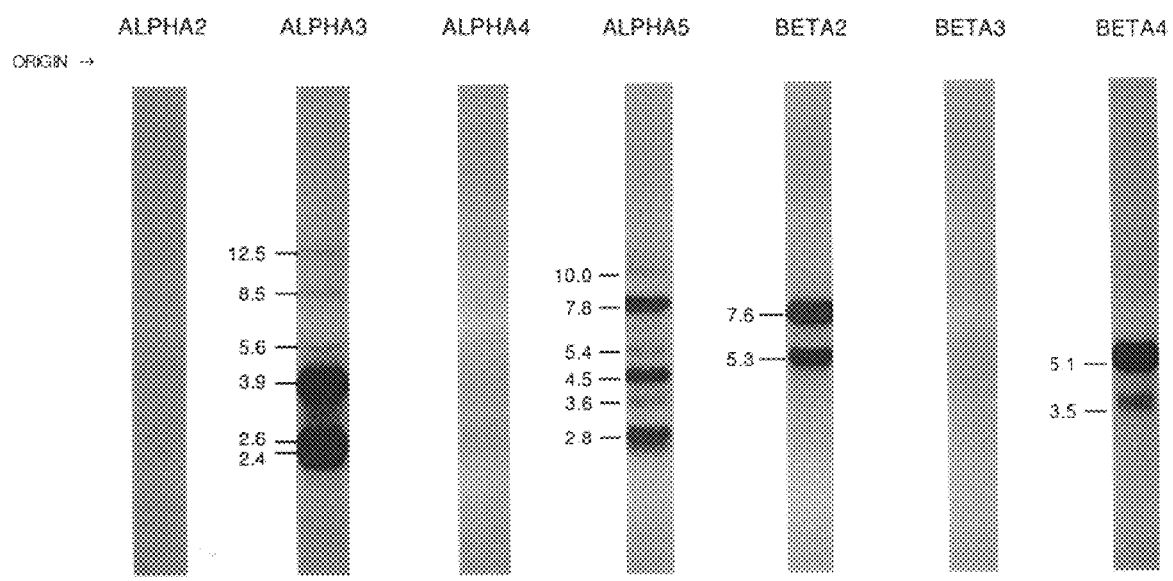

FIG. 28 is a photograph that shows autoradiograms of Northern blot hybridization analysis of PC12 poly (A+) RNA using radiolabeled probes prepared from all identified members of the rat nicotinic acetylcholine receptor-related gene family.

Figure 29:
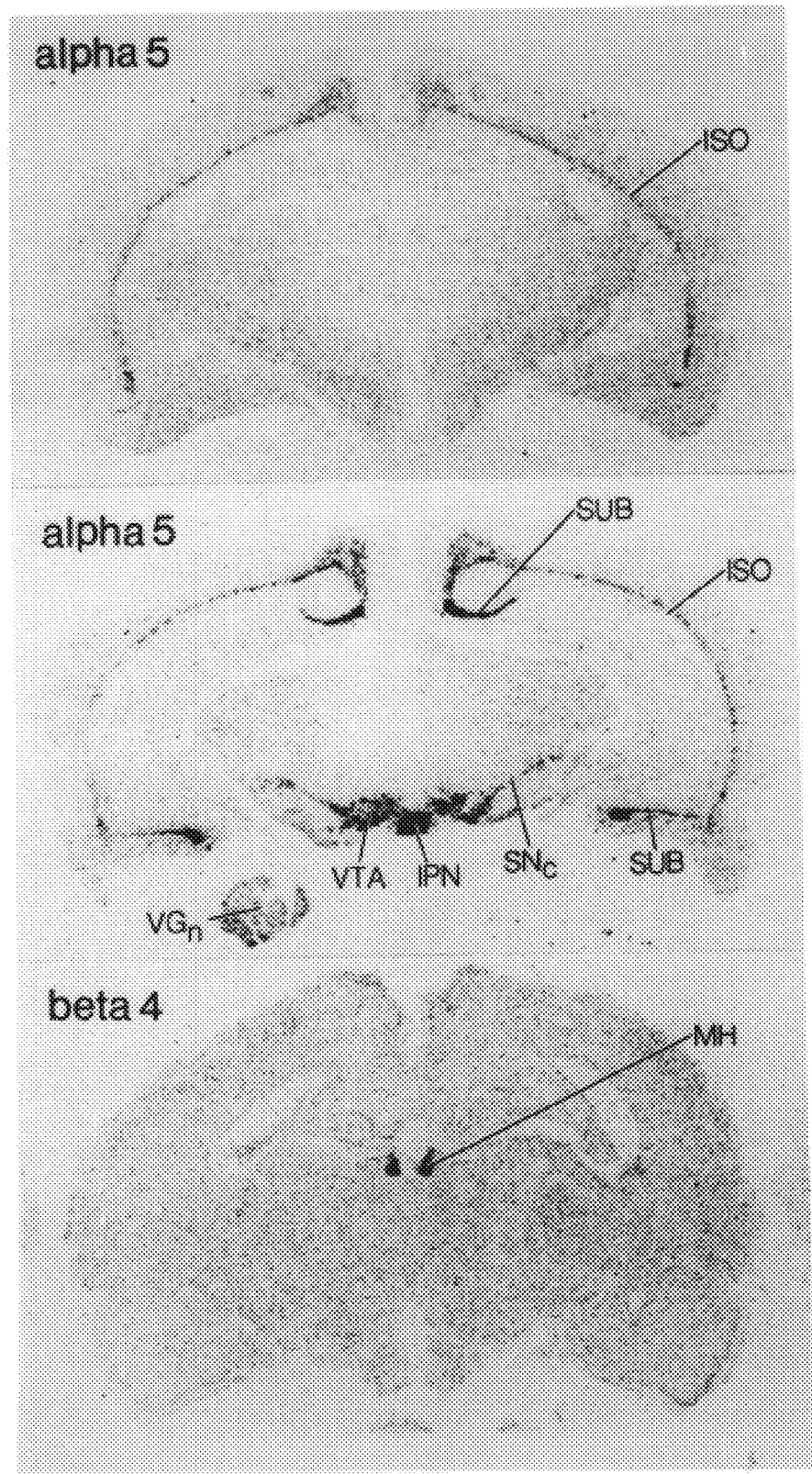

FIG. 29 is a photograph showing in situ hybridization autoradiograms that illustrate the distribution of alpha5 and beta4 transcripts in coronal sections of the rat brain.

DEFINITIONS

In the present specification and claims, reference will be made to phrases and terms of art which are expressly defined for use herein as follows:

As used herein, nAChRs means neuronal nicotinic acetylcholine receptor.

As used herein, AChR means nicotinic acetylcholine receptor.

As used herein, an agonist binding subunit is a subunit of the acetylcholine receptor that contains a binding site for the neurotransmitter, acetylcholine and its analogs. According to the nomenclature used herein, a putative neuronal nAChR subunit identified by cDNA cloning is given the name "alpha" if the Torpedo alpha subunit cysteines 128, 142, 192, and 193 are conserved. Agonist binding subunits of the present invention include: alpha2, alpha3, alpha4 (alpha4.1 and alpha4.2) and alpha5.

As used herein, a non-agonist binding subunit is a subunit of the acetylcholine receptor that does not bind agonists such as acetylcholine, nicotine, and analogs thereof, and also does not bind competitive antagonists. According to the nomenclature used herein, a putative neuronal nAChR subunit identified by cDNA cloning is given the name "beta" if only the Torpedo 128 and 142 cysteines are conserved. Non-agonist binding subunits include beta2, beta3 and beta4.

As used herein, the term antagonist refers to a substance that interferes with receptor function. Antagonists are of two types: competitive and non-competitive. A competitive antagonist (or competitive blocker) competes with the neurotransmitter for the same binding site. In the case of acetylcholine, an example of such an antagonist is 3.1 bungarotoxin. A non- competitive antagonist or blocker inactivates the functioning of the receptor by binding to a site other than the acetylcholine binding site.

As used herein, alpha1 refers to a gene which encodes an agonist binding subunit of the same name. This gene is expressed in skeletal muscle. (See Noda, et al., 1983; Merlie, et al., 1984; Boulter, et al., 1985; and Goldman, et al. 1985.)

As used herein, alpha2 refers to a gene, which has been identified in chick and rat, that encodes a neuronal agonist binding subunit of the same name. (See Experimental Section IV of the specification; also see Mauron, et al., 1985.) DNA coding for the alpha2 subunit has been deposited with the ATCC; the DNA (designated as pHYP16) has been accorded ATCC No. 67646.

As used herein, alpha3 refers to a gene that encodes a neuronal agonist binding subunit of the same name. This subunit is expressed in the PC12 cell line and various regions of the rat brain. (See Boulter, et al., 1986 and Goldman, et al., 1986.) DNA coding for the alpha3 subunit has been deposited with the ATCC; the DNA (designated as pPCA48) has been accorded ATCC No. 67642.

As used herein, alpha4 refers to a gene that encodes a neuronal agonist binding subunit of the same name. The cDNA clones encoding the proteins referred to herein as alpha4.1 and 4.2 are both derived from the alpha4 gene. DNAs coding for the alpha4.1 and 4.2 trancripts have been deposited with the ATCC. The alpha4.1 DNA (designated as pHYA23-1(E)1) has been accorded ATCC No. 67644; the alpha4.2 DNA (designated as pHIP3C(3) has been accorded ATCC No. 67645. [Clone pHIP3C(3) is a longer version of clone pHYA11, which is referred to in other parts of this specification as a clone for alpha4.2. Therefore, the DNA sequence of pHYA11 is encompassed within clone pHIP3c (3).]

As used herein, alpha5 refers to a gene encoding a neuronal agonist binding subunit of the same name. DNA coding for the alpha5 subunit has been deposited with the ATCC; the DNA (designated as PC1321) has been accorded ATCC No. 67652.

As used herein, beta1 refers to a gene encoding a non-agonist binding subunit of the same name. This subunit is expressed in the Torpedo electric organ and mammalian muscle receptors.

As used herein, beta2 refers to a gene encoding a neuronal nicotinic acetylcholine non-agonist binding subunit of the same name. DNA coding for the beta2 subunit has been deposited with the ATCC; the DNA (designated as pPCX49) has been accorded ATCC No. 67643.

As used herein, beta3 refers to a gene encoding a neuronal nicotinic acetylcholine non-agonist binding subunit of the same name. DNA coding for the beta3 subunit has been deposited with the ATCC; the DNA (designated as ESD76) has been accorded ATCC No. 67653).

As used herein, beta4 refers to a gene encoding a neuronal nicotinic acetylcholine non-agonist binding subunit of the same name. DNA coding for the beta4 subunit has been deposited with the ATCC; the DNA (designated as pZPC13) has been accorded ATCC No. 67893).

As used herein, MBTA means 4-(N-maleimido) benzyltrimethylammonium iodide (MBTA)

As used herein, PC12 refers to the rat adrenal chromaffin tumor cell line, PC12. This cell line expresses a "ganglionic" nicotinic acetylcholine receptor of the type found in sympathetic neurons (Patrick and Stallcup, 1977b).

As used herein, CAT means chloramphenicol acetyltransferase.

As used herein, COS means monkey kidney cells which express T antigen (Tag). See Gluzman, *Cell,* 23:175 (1981).

Use of the phrase "substantial sequence homology" in the present specification and claims means that DNA, RNA or amino acid sequences which have slight and non-consequential sequence variations from the actual sequences disclosed and claimed herein are considered to be equivalent to the sequences of the present invention, and as such are within the scope of the appended claims. In this regard, "slight and non-consequential sequence variations" mean that "homologous" sequences (i.e., the sequences that have substantial sequence homology with the DNA, RNA, or proteins disclosed and claimed herein) will be functionally equivalent to the sequences disclosed and claimed in the present invention. Functionally. equivalent sequences will function in substantially the same manner to produce substantially the same compositions as the nucleic acid and amino acid compositions disclosed and claimed herein.

Use of the phrase "substantially pure" in the present specification and claims as a modifier of DNA, RNA, polypeptides or proteins means that the DNA, RNA, polypeptides or proteins so designated have been separated from their in vivo cellular environments through the efforts of human beings; as a result of this separation, the substantially pure DNAs, RNAs, polypeptides and proteins are useful in ways that the non-separated, impure DNAs, RNAs, polypeptides or proteins are not.

The amino acids which comprise the various amino acid sequences appearing herein may be identified according to the following three-letter or one-letter abbreviations:

| Amino Acid | 3 Letter Abbreviation | 1 Letter Abbreviation |
|---|---|---|
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| L-Histidine | His | H |

-continued

| Amino Acid | 3 Letter Abbreviation | 1 Letter Abbreviation |
|---|---|---|
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| 1-Serine | Seri | S |
| L-Threonine | Thr | T |
| L-Tryptophan | Trp | W |
| L-Tyrosine | Tyr | Y |
| L-Valine | Val | V |

The nucleotides which comprise the various nucleotide sequences appearing herein have their usual single-letter designations (A, G, T, C or U) used routinely in the art.

In present specification and claims, references to Greek letters are written as both as alpha, beta, etc., and as α, β, etc.

DEPOSITS cDNA clones comprising neuronal nicotinic acetylcholine receptor genes alpha2 (clone pHYP16), alpha3 (clone pPCA48), alpha4.1 (clone pHYA23-1(E)1), alpha4.2 (clone pHIP3C(E)3), alpha5 (clone PC1321), beta2 (clone pPCX49), beta3 (clone ESD76) and beta4 (clone pZPC13), all of which are in *E. coli* HB101, have been deposited at the American Type Culture Collection, 10801 University Boulevard, Manassas, Va., 20110U.S.A. (ATCC) under the terms of the Budapest Treaty on the International Recognition of Deposits of Microorganisms for Purposes of Patent Procedure and the Regulations promulgated under this Treaty. Samples of the cloned genes are and will be available to industrial property offices and other persons legally entitled to receive them under the terms of said Treaty and Regulations and otherwise in compliance with the patent laws and regulations of the United States of America and all other nations or international organizations in which this application, or an application claiming priority of this application, is filed or in which any patent granted on any such application is granted.

The ATCC Deposit Numbers for the eight deposits are as follows:

alpha2 clone pHYP16 ATCC No. 67646
alpha3 clone pPCA48 ATCC No. 67642
alpha4.1 clone pHYA23-1(E)1 ATCC No. 67644
alpha4.2 clone pHIP3C(3) ATCC No. 67645
alpha5 clone PC1321 ATCC No. 67652
beta2 clone pPCX49 ATCC No. 67643
beta3 clone EDS76 ATCC No. 67653
beta4 clone pZPC13 ATCC No. 67893

SUMMARY OF THE INVENTION

The invention discloses a new family of neuronal nicotinic acetylcholine receptors and genes that encode these receptors. More specifically, in one aspect, the present invention comprises substantially pure double-stranded DNA sequences wherein the sense strand of the sequence encodes the amino acid sequence of a mammalian neuronal nicotinic acetylcholine receptor subunit selected from the group consisting of alpha2, alpha4, alpha5, beta2, beta3 and beta4.

In another aspect, the invention comprises substantially pure single-stranded DNA sequences and mRNA transcribed therefrom wherein the sequences encode amino acid sequences of a mammalian neuronal nicotinic acetylcholine receptor subunit selected from the group consisting of alpha2, alpha4, alpha5, beta2, beta3 and beta4.

In another aspect, the invention comprises substantially pure DNA sequences encoding the neuronal nicotinic acetylcholine receptor subunits of the present invention. Clones representative of such sequences have been deposited with the American Type Culture Collection for patent purposes. The cDNA clones of the invention include representative clones: alpha2 clone pHYP16 (ATCC No. 67646), alpha3 clone pPCA48 (ATCC No. 67642), alpha4.1 clone pHYA23-1(E)1 (ATCC No. 67644), alpha4.2 clone pHIP3C(3) (ATCC No. 67645), alpha5 clone PC1312 (ATCC No. 67652), beta2 clone pPCX49 (ATCC No. 67643), beta3 clone ESD76 (ATCC No. 67653) and beta4 clone (ATCC No. 67893). DNA sequences from such clones can be used as probes to identify and isolate other neuronal nicotinic acetylcholine receptors from cDNA libraries.

In still another aspect, the invention comprises a cell, preferably a mammalian cell, transformed with DNA sequences of the invention.

Still further, the invention comprises novel neuronal nicotinic acetylcholine receptors made by expression of DNA sequences of the invention, or translation of the corresponding mRNAs. Such novel receptors include-the individual alpha2, alpha4.1, alpha4.2, alpha5, beta2, beta3 and beta4 receptor subunits, plus functional subunit combinations including, but not limited to, alpha2+beta2 subunits, alpha3+beta2 subunits, alpha4+beta2 subunits, alpha2+beta4 subunits, alpha3+beta4 subunits, and alpha4+beta4 subunits.

Still further the invention comprises DNA, RNA and proteins that are functionally equivalent to the DNAs, RNAs and proteins of the present invention. Such functionally equivalent DNAs, RNAs and proteins will function in substantially the same manner as the DNAs, RNAs and proteins of the invention.

DETAILED DESCRIPTION OF THE INVENTION

The present invention is the discovery and isolation of DNA segments that encode receptor subunits that, in combination, comprise a new family of nicotinic acetylcholine receptors that are expressed in the brain and nerve cells. To gain access to these new neuronal receptor gene encoding segments, molecular cloning techniques were used to first isolate complementary DNA clones coding for the acetylcholine receptor expressed in the Torpedo fish electric organ. (see Ballivet, et al., 1983 and Patrick, et al., 1983). The cDNA clones isolated from the electric organ were then used in nucleic acid hybridization experiments to obtain cDNA and genomic clones for the subunits (referred to as the alpha (α), beta (β), gamma (λ), and delta (δ) subunits) of the acetylcholine receptors expressed in mouse skeletal muscle.

The availability of cDNA clones encoding the muscle nicotinic receptor made it possible to extend these studies in the medically important direction of neuronal receptors. Using a cDNA clone encoding a mouse muscle nicotinic acetylcholine receptor alpha subunit as a hybridization probe, rat and mouse cDNA and genomic libraries were screened for related mRNAs or genes. These DNA sequences were then used to further probe for related neuronal subunit sequences. This method resulted in the isolation of cDNA sequences that had significant sequence homology with the probes. Eight of these related sequences, which code for neuronal nicotinic acetylcholine receptor subunits referred to herein as alpha2, alpha3, alpha4 (as represented by alpha4.1 and alpha4.2 sequences), alpha5, beta2, beta3, and beta4 are disclosed and discussed in the present specification.

As a result of work done at the Molecular Neurobiology Laboratory at the Salk Institute for Biological Studies and elsewhere, it is now believed that there is a family of genes related to the alpha agonist binding subunit of acetylcholine receptors found at the neuromuscular junction. The first three identified members of this agonist binding alpha gene family are: alpha1, which is expressed in Torpedo electric organ and mammalian skeletal muscle (Noda, et al., 1983; Merlie, et al., 1984; Boulter, et al., 1985; Goldman, et al., 1985); alpha2, which was initially identified as a gene in chick (Mauron, et al., 1985) and suspected of being one in rat (Nef, et al., 1986); and alpha3, which is expressed in the PC12 cell line and various regions of the rat brain (Boulter, et al., 1986; Goldman, et al., 1986). As this specification discloses (see Experimental Section I), the alpha4 gene (encoding clones alpha4.1 and 4.2) represents the fourth member of this alpha subunit gene family, while alpha5 represents the fifth.

Also as a result of work done at the Molecular Neurobiolgy Laboratory at the Salk Institute, it is now believed that there is a family of genes related to the non-agonist binding beta subunit of the acetylcholine receptors found at the neuromuscular junction. The first identified member of this gene family was beta1, which is a non-agonist binding subunit of the Torpedo electric organ and mammalian muscle receptors. In this specification, the existence of three more members of this non-agonist binding gene family are disclosed: these new members are beta2, beta3 and beta4.

The polypeptides encoded by the alpha2, alpha3, alpha4 and alpha5 genes have features found in the non-neuronal alpha subunits of the Torpedo electric organ and mammalian muscle nicotinic acetylcholine receptors. (See FIGS. 15C (parts 1–3) and 2A (parts 1–3).) One of these features, which was observed originally in the alpha1 subunit, is the presence of two adjacent cysteine residues in the presumed extracellular domain of the protein. These two cysteine residues, which have been shown to be close to the agonist-binding site (Kao, et al., 1984; Kao and Karlin, 1986), are a feature common to the agonist-binding alpha1 subunits, but not the beta, gamma, and delta subunits of the electric organ and mammalian muscle receptors.

Turning now to the new neuronal subunits of the present invention, because of their structural and sequence homology, and the presence of the conserved cysteines, it is proposed that the alpha2, alpha3, alpha4 and alpha5-genes encode agonist-binding subunits of neuronal receptors. On the contrary, because the new receptor subunits referred to as beta2, beta3 and beta4 lack these two binding domain cysteine residues, it is believed that beta2, beta3 and beta4 genes encode are non-agonist binding subunits.

As the results in the following Experimental Sections demonstrate, the beta2 and beta4 polypeptides can functionally substitute for the muscle beta1 subunit in a nicotinic acetylcholine receptor. (See especially, Experimental Sections II–VI.) As is also shown in the Experimental Sections, expression studies reveal that at least three different types of functional neuronal nicotinic acetylcholine receptors are produced upon co-injection into oocytes of beta2 or beta4 mRNAs and each of the neuronal alpha2, alpha3 and alpha4 mRNAs. (See Experimental Sections II–IV.) These results, together with the distribution of alpha2, alpha3, alpha4, alpha5 and beta2, beta3 and beta4 transcripts in the brain (see Experimental Sections), are consistent with the premise that different neuronal nicotinic acetylcholine receptors are comprised of at least one beta subunit in combination with different agonist-binding alpha subunits.

The results disclosed in the following Experimental Sections also show that neuronal nicotinic acetylcholine receptors differ from mammalian muscle nicotinic receptors in that they can be constituted from only two different gene products (alpha and beta). This is significant since, in all experiments reported to date, nicotinic acetylcholine receptors have been formed with αβλδ subunits, αβδ subunits, αβδ subunits, or αλδ subunits, but not with any pairwise combinations (Kurosaki, et al., 1987). In sharp contrast, the alpha2, alpha3 and alpha4 neuronal receptors can be constituted with only two different types of polypeptide chains, one derived from a specific alpha gene and one derived from a beta gene.

Representative cDNA clones that encode the new neuronal nicotinic acetylcholine receptor subunits of the present invention have been deposited with the ATCC for patent purposes. These DNAs include alpha2 clone pHYP16 (ATCC No. 67646), alpha3 clone pPCA48 (ATCC No. 67642), alpha4.1 clone pHYA23-1(E)1 (ATCC No. 67644), alpha4.2 clone pHIP3C(3) (ATCC No. 67645), alpha5 clone PC1321 (ATCC No. 67652), beta2 clone pPCX49 (ATCC No. 67643), beta3 clone ESD76 (ATCC No. 67653) and beta4 clone (ATCC No. 67893). The DNA and amino acid sequences for alpha4.1 and alpha 4.2 are shown in FIGS. 2A to 2F respectively; the sequences for beta2 are shown in FIGS. 7B to 7D; the sequences for alpha2 are shown in FIG. 15C to 15F; the sequences for beta3 are shown in FIGS. 19A to 19C; the sequences for beta4 are shown in FIGS. 24A to 24C; and the sequences for alpha5 are shown in FIGS. 25A to 25C.

The cDNAs that encode neuronal nicotinic acetylcholine receptors of the present invention can be used as probes to find other members of the neuronal nicotinic acetylcholine receptor gene family. When the cDNAs are used for this purpose, it is preferable to use as probes those sequences that are most highly conserved within this gene family, i.e., those that show the greatest homology. (The highly conserved sequences are thought to encode portions of the receptor subunits that comprise the transmembrane regions and therefore contribute to the transmembrane channel. Therefore one can assume that cognate genes will also contain sequences that are closely related to the transmembrane region.)

Hybridization methods are well known to those skilled in the art of molecular biology. See for example, Nef, et al., (1986) and Benton and Davis, 1977); also see the hybridization procedures and conditions in the vaious experimental sections of this specification.

Turning now to the specific experimental sections, details of the new alpha4 gene (and the alpha4.1 and 4.2 polypeptides encoded thereby) are disclosed in Experimental Section I. DNA analysis of the 4.1 and 4.2 cDNA clones reveals that they differ slightly in their nucleotide and amino acid sequences. A possible explanation for these differences is that the respective mRNAs arise from one gene by alternative splicing of a single primary transcript. Such a mechanism would provide another means for generating receptor diversity in the brain.

In Experimental Section I, as well as in Experimental Sections IV and VI, in situ hybridization is used to show that the pattern of alpha2, alpha3, alpha4 and alpha5 expression in the brain is different. It is reasonable to assume that the properties of a receptor are determined by the primary structure of the receptor protein. Thus, it is believed that the various neuronal alpha subunits have different functional properties in the different brain regions.

In Experimental Section II, the primary structure of the beta2 subunit is disclosed. Although this polypeptide is homologous to the neuronal alpha subunits, it lacks the two adjacent cysteine residues, shown to be near the agonist-binding site. In this respect, the beta2 subunit is similar to the beta, gamma, and delta subunits of the electric organ and muscle receptors.

In Experimental Section II, additional evidence that the neuronal beta2 subunit can functionally substitute for the muscle beta subunit in a nicotinic receptor is provided. In addition, as is detailed, expression studies have shown that at least three types of functional neuronal nicotinic acetylcholine receptors are produced upon co-injection of beta2 mRNA and each of the neuronal alpha2, alpha3, and alpha4 mRNAs. (Similar results are found with beta4) These data, together with the distribution of beta2 and beta4 transcripts in the brain, are consistent with the premise that different neuronal nicotinic acetylcholine receptors are composed of beta subunits and different agonist-binding alpha subunits.

In Experimental Section III, additional details of the new neuronal nicotinic acetylcholine receptors are described. For example, it is shown that heterogeneous functional receptors constituted from at least one beta2 subunit and neuronal alpha3 or alpha4 subunits have pharmacological characteristics of ganglionic nicotinic acetylcholine receptors, i.e., they are blocked by the ganglionic nicotinic receptor blocker bungarotoxin 3.1, but not by the neuromuscular junction nicotinic receptor blocker, α-bungarotoxin. Of particular note is the fact that alpha2 in conjunction with beta2 produces a receptor that has pharmacological characteristics unlike the foregoing, namely, this receptor is not blocked by either bungarotoxin 3.1 or α-bungarotoxin.

In Experimental Section IV, among other things, the results of in situ brain hybridization histochemical studies are disclosed which show that alpha2 mRNA is expressed in a small number of regions, in contrast to the wide distribution of the other known neuronal agonist-binding subunits (e.g., alpha3 and alpha4). These studies also show that alpha2, alpha3 and alpha4 transcripts are co-expressed with beta2 transcripts in many brain regions. These results suggest that the functional combinations observed in oocytes may also occur in vivo. However, the studies also show that in some regions, beta2 and alpha2, alpha3 and alpha4 transcripts are not co-expressed. This observation raises the possibility of the existence of other alpha-type and beta-type subunits.

In Experimental Section V isolation and characterization of the beta3 clone is disclosed. This clone encodes a protein that has structural features found in other nicotinic acetylcholine receptor (nAchR) subunits. More specifically, two cysteine residues that correspond to cysteines 128 and 142 of the Torpedo nAchR alpha subunit are present in beta3. Absent from beta3 are two adjacent cysteine residues that correspond to cysteines 192 and 193 of the Torpedo alpha subunit. In situ hybridization histochemistry, performed using probes derived from beta3 cDNAs, demonstrated that the beta3 gene is expressed in the brain. Thus, beta3 is the fifth member of the nAchR gene family that is expressed in the brain. The pattern of beta3 gene expression partially overlaps with that of the neuronal nAchR subunit genes alpha3, alpha4, or beta2. These results lead to the conclusion that the beta3 gene encodes a neuronal nAchR subunit.

In Experimental Section IV features of the beta4 clone are disclosed. This clone encodes a protein that also has structural features found in other nicotinic acetylcholine receptor (nAchR) subunits. More importantly, when mRNA from this clone was injected into oocytes in various pairwise combinations of alpha2, alpha3, alpha4 and alpha5 transcripts, it was found that beta 4 can also functionally substitute for the muscle beta unit just as the neuronal beta2 subunit can do. Thus, beta4 is the sixth member of the nAchR gene family.

Without further elaboration, it is believed that one of ordinary skill in the art can, using the preceding description, and the following Experimental Sections, utilize the present invention to its fullest extent. The material disclosed in the experimental sections, unless otherwise indicated, is disclosed for illustrative purposes and therefore should not be construed as being limiting in any way of the appended claims.

EXPERIMENTAL SECTION I

MEMBERS OF A NICOTINIC ACETYLCHOLINE RECEPTOR GENE FAMILY ARE EXPRESSED IN DIFFERENT REGIONS OF THE MAMMALIAN CENTRAL NERVOUS SYSTEM

INTRODUCTION

Nicotinic acetylcholine receptors found in the peripheral and central nervous systems differ from those found at the neuromuscular junction. Our group isolated a cDNA clone encoding our alpha subunit of a neuronal acetylcholine receptor expressed in both the peripheral and central nervous systems (Boulter, et al., 1986). In this experimental section, the isolation of a cDNA encoding the alpha subunit of a second acetylcholine receptor expressed in the central nervous system is reported. Thus, it is clear that there is a family of genes coding for proteins with sequence and structural homology to the alpha subunit of the muscle nicotinic acetylcholine receptor. Members of this gene family are expressed in different regions of the central nervous system and, presumably, code for subtypes of the nicotinic acetylcholine receptor.

A cDNA clone encoding a mouse muscle nicotinic acetylcholine receptor alpha subunit was used as a hybridization probe to identify putative neural nicotinic acetylcholine receptor encoding cDNA clones. One such clone was isolated from a cDNA library prepared using RNA isolated from the rat pheochromocytoma cell line, PC12. This clone encodes a protein with considerable sequence and structural homology to the alpha subunit of the acetylcholine receptor found at the neuromuscular junction (Boulter, et al., 1986). Analysis of genomic restriction fragments that hybridize to this clone suggested that there is a family of related genes. The first three identified members of this gene family to be identified are:. alpha1, which is expressed in skeletal muscle (Noda, et al., 1983; Merlie, et al., 1984; Boulter, et al., 1985; Goldman, et al., 1985); alpha2, which has been identified as a gene in chick and rat (Mauron, et al., 1985); and alpha3, which is expressed in the PC12 cell line and various regions of the rat brain (Boulter, et al., 1986; Goldman, et al., 1986). The differential expression in the mammalian central nervous system of a fourth member of this alpha subunit gene family, alpha4 is disclosed here.

RESULTS

Genes Encoding Nicotinic Acetylcholine Receptor Alpha Subunits Are Expressed In The Mammalian CNS Our group has shown that radioactive probes prepared from cDNA clones encoding the mouse muscle and rat neuronal acetylcholine receptor alpha subunits hybridize to RNA species present in poly(A)$^+$ RNA purified from rat brain hypothalamus, hippocampus and cerebellum (Boulter, et al., 1986). To determine the identity and functional significance of these hybridizing RNA species, poly(A)$^+$ RNA from the rat hypothalamus and hippocampus was purified and cDNA libraries in λgt10 were prepared as previously described (Gubler and Hoffmann, 1983; Huynn, et al., 1985). These libraries were screened with probes derived from a cDNA encoding the-mouse muscle acetylcholine receptor alpha subunit (alpha1) (Boulter, et al., 1985) and a cDNA encoding the alpha3 gene product (Boulter, et al., 1986). Seven clones (three from the hippocampus library and four from the hypothalamic library) that contained inserts which hybridized to both probes were studied. These seven clones were determined to contain related inserts, on the basis of restriction enzyme analysis and partial sequence analysis, and were analyzed further.

These clones fall into two classes. Clone 4.1, typical of the first class, is 2052 nucleotides long, with an open reading frame of 1875 base pairs. Clone 4.2.is representative of the second class and is 1938 nucleotides long, with an open reading frame of 1524 base pairs. FIG. 1 illustrates the relationship of these two clones to each other.

DNA sequence analysis of these two clones reveals that they differ in two respects. First, clone 4.2 starts at nucleotide 389 of clone 4.1 and secondly, clones 4.2 and 4.1 differ in their 3' ends starting with nucleotide 1871 of clone 4.1 (FIG. 2A (parts 1–3) and 2B (parts 1–3). The sequences between bases 389 and 1871 of clone 4.1 are identical to the bases from the 5' end to base 1482 of clone 4.2. A possible mechanism that accounts for the difference at their 3' end is that their respective mRNAs arise from one gene by alternative splicing of a single primary transcript. This is supported by the presence of the trinucleotide CTG at the proposed splice site (position 1868–1870). This trinucleotide is commonly found on the exon side of exon/intron borders. The dinucleotides CT (clone 4.1) or GT (clone 4.2) which are adjacent to this trinucleotide in the cDNA clones are often found on the exon side of intron/exon borders (Breathnach and Chambon, 1981). It is proposed, therefore, that clones 4.1 and 4.2 are derived from a common gene, which is referred to as alpha4.

Based on the predicted alpha4 amino acid sequence (FIG. 2A (parts 1–3) and 2B (parts 1–3)) and its alignment with alpha1 and alpha3 (FIG. 3 (parts 1–3)), it is not possible to unambiguously assign the N-terminus of the mature alpha4.1 protein. The Ala residue aligned with the Ser that is thought to form the N-terminus of the mature alpha1 sequence cannot be the N-terminal residue of alpha4.1 since it is preceded by an Arg. The signal peptidase requires (among other things) the presence of an uncharged amino acid with a small side-chain preceding the peptide bond which it cleaves. Based on the sequence patterns around signal sequence cleavage sites (von Heljne, 1983; Perlman and Halvorson, 1983) the site predicted to be the best substrate for the signal peptidase in the alpha4.1 leader sequence would be between Ser and His; another possible site is between Thr and Arg (FIG. 3 (parts 1–3)). Although clone 4.1 lacks an initiator methionine, it has a hydrophobic leader sequence characteristic of secreted or membrane-spanning proteins (FIG. 3 (parts 1–3)). In contrast, clone 4.2 lacks coding sequences corresponding to the first 129 amino acids encoded by clone 4.1 (FIG. 1). The nucleotide sequences in the region where alpha4.1 and alpha4.2 overlap encode proteins that are identical (FIGS. 1, 2A (parts 1–3) and 2B parts (1–3)). The protein encoded by clone 4.2 is longer by 1 amino acid at the C- terminus than the protein encoded by clone 4.1. Furthermore, the last 2 amino acids of 4.1 (Ala-Cys) are different in 4.2 (Gly-Met), resulting in a total of 3 unique amino acids at the C-terminus of clone 4.2 (FIG. 2A (parts 1–3) and 2B (1–3)).

Based on homology with the muscle (alpha1) and the previously described neuronal (alpha3) alpha subunit protein (FIG. 3 (parts 1–3)), it is proposed that the proteins encoded by clones 4.1 and 4.2 are also alpha subunits of a new class of nicotinic acetylcholine receptors. However, the best evidence that the alpha4 gene encodes a nicotinic acetylcholine receptor alpha subunit is derived from the conservation of structural domains present in the muscle alpha subunit. Specifically, these domains are: (1) four hydrophobic, putative trans-membrane domains; (2) an amphipathic helix just prior to the fourth hydrophobic domain; and (3) an extracellular domain which contains two features common to all alpha subunits sequenced to date: (a) four cysteine residues at positions 128, 142, 192 and 193, (the residue number corresponds to the numbering system adopted for the muscle alpha subunit (Boulter, et al., 1985)) of which the latter two are in the vicinity of the acetylcholine binding site on the muscle receptor (Kao, et al., 1984) (see arrows in FIG. 3 (parts 1–3); and (b) a potential N-linked glycosylation site at position Asn141. The protein encoded by clone 4.1 has a second potential glycosylation site at Asn24 (see asterisks in FIG. 3 (parts 1–3). This glycosylation site is also found in the alpha3 gene product (FIGS. 3A and 3B (parts 1–3). Thus, both neural receptors contain a potential glycosylation site at Asn24 not seen in any of the muscle receptors sequenced to date.

It is interesting that the proposed membrane spanning regions are markedly conserved. These domains exhibit amino acid homologies ranging from 50–100% between alpha4 and either the alpha1 or alpha3 gene products. In contrast, the region thought to be cytoplasmic (between membrane spanning regions III and IV), exhibits little or no conservation with respect to alpha1 and alpha3 (FIGS. 3A and 3B (parts 1–3). However, in this putative cytoplasmic region there is a potential phosphorylation site that is conserved between alpha3 and alpha4: KSSS and RSSS (FIGS. 3A and 3B (parts 1–3); a similar sequence is phosphorylated in the Torpedo nicotinic acetylcholine receptor (Safran, et al., 1986). There is evidence that phosphorylation of the Torpedo, acetylcholine receptor isolated from the electric organ increases the rate of desensitization (Huganir, et al., 1986). The neuronal alpha subunits, alpha3 and alpha4, have much longer putative cytoplasmic regions than the muscle receptor alpha subunit (alpha1). Overall, the proteins encoded by clones 4.1 and 4.2 (alpha4) exhibit 57% amino acid sequence identity with the protein encoded by the alpha3 gene and 50% identity with the muscle alpha subunit (alpha1).

The proteins derived from the alpha4 gene and encoded by clones 4.1 and 4.2 are proposed to be alpha subunits of nicotinic acetylcholine receptors. This proposal is based on the conservation of the proposed structural domains in the muscle nicotinic acetylcholine receptor alpha subunit and on the high degree of homology between the protein sequences encoded by clones 4.1 and 4.2 and the muscle receptor alpha subunit sequence. Based on this homology, clones 4.1 and 4.2 have been classified as two members of the fourth class of alpha subunit encoding genes (alpha4).

Expression of the Alpha4 Gene in the Central Nervous System

An analysis of brain regions expressing RNA homologous to clone 4.1 was performed by in situ hybridization to rat brain sections using radiolabeled antisense RNA made from clone 4.1 (FIG. 4A). The result of these experiments showed that clone 4.1 antisense probe hybridizes to the neocortex, many thalamic nuclei, medial habenula, ventral tegmental area, substantia nigra pars compacta, lateral (dorsal part) and medial geniculate nuclei, and throughout the hypothalamus (FIG. 4A). A control probe, made from the sense strand of clone 4.1, exhibited little hybridization to these areas of the brain (FIG. 4B). This sense strand probe was used as a measure of nonspecific hybridization. No hybridization above background was observed to the hippocampus when using the antisense strand probe. However, since the 4.1 cDNA was found in a cDNA library prepared using RNA derived from the hippocampus, the gene encoding this cDNA may also be expressed in this region of the rat brain, albeit at low levels.

Figure 5A:
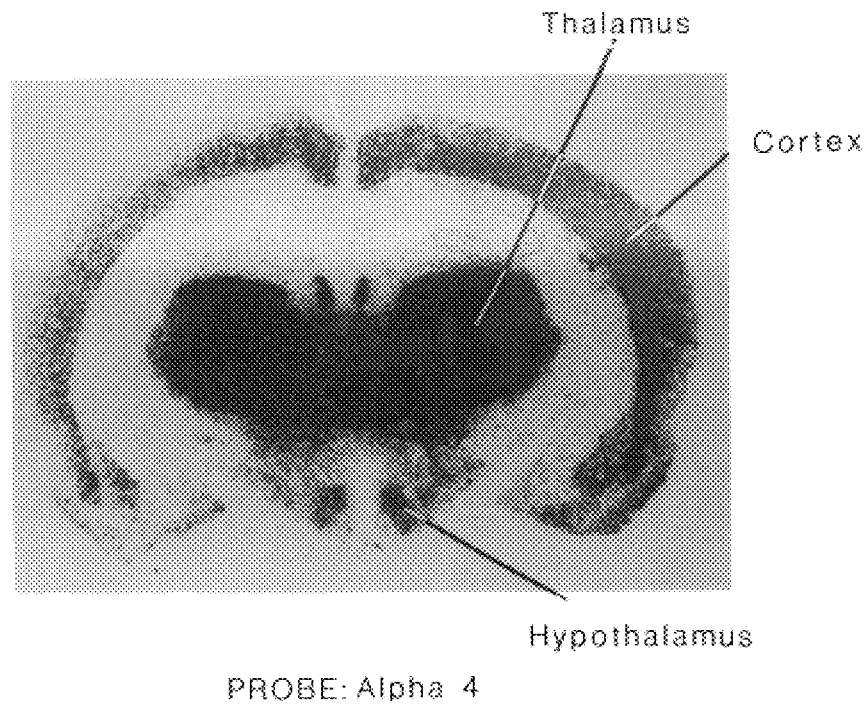
Figure 5B:
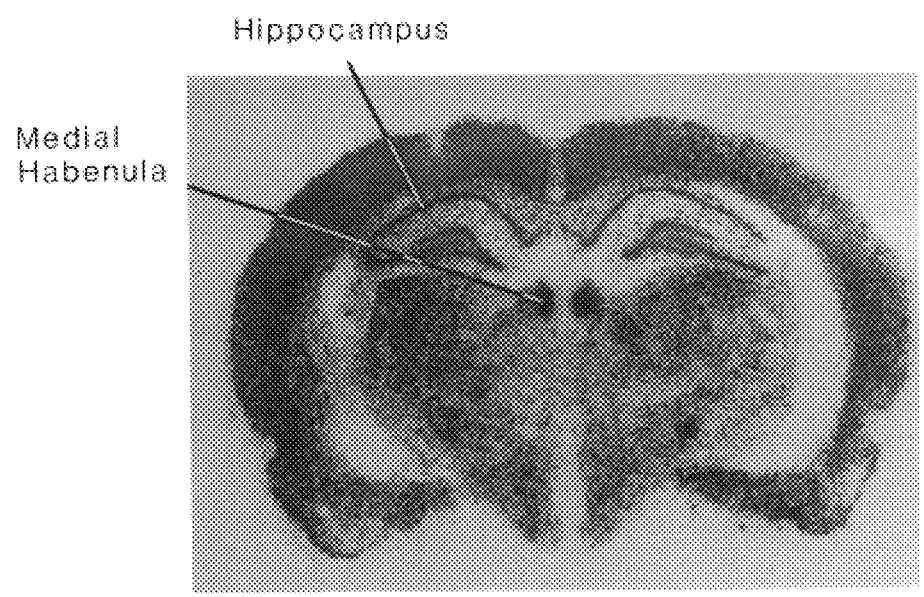

Alpha4 is the second gene of the alpha subunit gene family shown to be expressed in the central nervous system. Our group has shown that the alpha3 gene is expressed in the central nervous system (Boulter, et al., 1986; Goldman, et al., 1986). To determine whether alpha3 and alpha4 genes were expressed in the same or different regions of the central nervous system a comparison of alpha3 and alpha4 gene expression in rat brain sections was accomplished by in situ hybridization of radiolabeled antisense RNA probes made from a cDNA clone coding for the alpha3 gene product and clone 4.1 (alpha4) (FIG. 5A). This experiment shows that although both clones hybridize strongly to RNA in the medial habenula, the alpha4 gene is also expressed throughout the thalamus, hypothalamus and cortex, while little signal is detected in these same areas when the probe for alpha3 gene expression is used (FIG. 5A) (Goldman, et al., 1986). These results demonstrate that the alpha3 and alpha4 genes are expressed in different locations in the brain and thus must represent different receptor systems, arguing against the possibility that they represent different subunits of the same receptor.

To demonstrate that the RNA detected by the in situ hybridization experiments is in fact the product of the alpha4 gene, S1 nuclease protection experiments were performed. The 3' 596 nucleotides of clone 4.1 were subcloned into the single-strand phage, M13mp18. This region of the cDNA was chosen since it contains the nucleotide sequence that exhibits the least homology with the muscle alpha1 gene and the neuronal alpha3 gene, but covers the extreme 3' end of the 4.1 clone which differs in sequence from clone 4.2. The 596 bases of this M13 subclone contain 406 bases that are common to clones 4.1 and 4.2, plus an additional 190 bases that are unique to clone 4.1. The single-stranded M13 recombinant DNA containing the 3' 596 bases of clone 4.1 was hybridized with poly(A)+ RNA isolated from various brain regions. S1 nuclease was added and those heteroduplexes surviving nuclease digestion were size- fractionated on denaturing acrylamide gels. Nucleic acids were electroblotted to Gene Screen Plus and visualized by hybridization with radiolabeled 4.1 cDNA (FIG. 6A). If RNA exists corresponding to clone 4.1, one predicts the RNA will hybridize to the 596 bases subcloned into M13 and protect this DNA from digestion by S1 nuclease. If RNA exists corresponding to clone 4.2, one predicts this RNA will hybridize to only 406 of the 596 bases subcloned into M13 and protect this portion of the subclone from S1 nuclease digestion. Furthermore, if both RNAs are expressed, then both a 596 and a 406 nucleotide long protected fragment are predicted. The results in FIG. 6A show that there are not two but three species of RNA homologous to the 4.1 cDNA clone. The largest protected fragment (about 600 bases)

corresponds to complete protection of the cDNA probe by the RNA. Thus, at least in the thalamus, hypothalamus and spinal cord, some of the hybridization observed in situ is a result of expression of the alpha4 gene encoding clone 4.1 sequences.

Two hybridizing bands of about 390 and 400 nucleotides were found in addition to the 600 nucleotide long fragment corresponding to clone 4.1. These two protected fragments result from protection of the 4.1 cDNA subclone (596 nucleotides long) by two additional and different RNA molecules. The discovery of two partially protected fragments differing by a few nucleotides was surprising. One of these protected fragments results from the expression of RNA corresponding to clone 4.2 sequences (which are predicted to be 406 nucleotides long). The other fragment may represent another RNA product of the alpha4 gene with yet a different 3' sequence. Therefore, these results demonstrate that, in the hypothalamus, thalamus and spinal cord, the signal observed upon in situ hybridization to brain sections is a consequence of RNA transcripts corresponding to clones 4.1 and 4.2. Furthermore, these S1 nuclease protection experiments show that RNA corresponding to clone 4.2 (the partially protected fragment) is expressed at higher levels than RNA corresponding to clone 4.1 (the fully protected fragment).

These results demonstrate that in the central nervous system multiple nicotinic acetylcholine receptor alpha subunits are expressed. This diversity arises from expression of different gene products (alpha3 and alpha4), and probably from alternative processing of a primary transcript derived from a single gene (alpha4; clones 4.1 and 4.2).

DISCUSSION

Neurotransmitter receptors localized at chemical synapses are responsible for transducing chemical signals from the pre-synaptic cell into an appropriate response by the post-synaptic cell. The nicotinic acetylcholine receptor found at the neuromuscular junction is the best studied neurotransmitter receptor; however, little is known about central nervous system nicotinic receptors. Experiments that map cholinergic systems within the brain (Armstrong, et al., 1983; Houser, et al., 1983; Ichikawa and Hirata, 1986) and ligand binding studies (Clarke, et al., 1985) have identified many brain areas thought to contain these receptors. Furthermore, nicotinic receptors found in the central nervous system occur both pre- and post-synaptically (Lichtensteiger, et al., 1982; Sakurai, et al., 1982).

In this experimental section genetic evidence for acetylcholine receptor diversity in the mammalian central nervous system is provided. This diversity results, in part, from a family of nicotinic acetylcholine receptor alpha subunit encoding genes (alpha3 and alpha4) and in part from alternate RNA processing of the alpha4 gene transcript represented by clones 4.1 and 4.2. Analysis of these receptors and the regions of the brain in which they are expressed makes it possible to begin to relate structure to both function and location in the nervous system.

The alpha4 gene encoding clones 4.1 and 4.2 represents the fourth identified member of an acetylcholine receptor gene family coding for proteins homologous to the muscle alpha subunit. The first three members of this gene family to be identified were: (1) The muscle nicotinic acetylcholine receptor alpha subunit encoding gene, for which the corresponding cDNAs have been isolated from a number of different species, and is referred to here as the alpha1 gene (Noda, et al., 1983; Boulter, et al., 1985); (2) Chick and rat genomic clones (alpha2) have been isolated that code for an alpha subunit-like molecule (Mauron, et al., 1985); and (3) The alpha3 gene expressed in the rat PC12 cell line, the adrenal medulla, and certain brain areas (Boulter, et al., 1986; Heinemann, et al., 1986; Goldman, et al., 1986). Therefore, diversity in nicotinic acetylcholine receptors can be explained, at least in part, by existence of a gene family encoding the alpha subunits of these receptors. Furthermore, clones 4.1 and 4.2 probably result from differential splicing of the alpha4 gene primary transcript providing another mechanism for generating receptor diversity in the brain.

The in situ hybridization experiments (FIGS. 4A & B and 5A & B) show that alpha4 is expressed in the neocortex, many thalamic nuclei, medial habenula, dorsal lateral (dorsal part) and medial geniculate nuclei, substantia nigra pars compacta, ventral tegmental area, hypothalamus, brain stem and spinal cord. Most of these areas of the brain have also been shown to bind radiolabeled acetylcholine or nicotine (Clarke, et al., 1985), consistent with the idea that clones 4.1 and 4.2 code for alpha subunits of neural nicotinic receptors.

Besides binding nicotine and acetylcholine, the acetylcholine receptor found in muscle binds and is inactivated by α-bungarotoxin. In mammals, α-bungarotoxin binds to components in the nervous system whose function remains unknown, but which are distinct from the ganglionic nicotinic acetylcholine receptor (Patrick and Stallcup, 1977a,b). Furthermore, the brain regions that bind radiolabeled nicotine or acetylcholine are different from the regions that bind α- bungarotoxin (Clarke, et al., 1985). Our results indicate that the in situ hybridization pattern, seen when probes for the alpha4 gene product are used, correlate best with nicotine and acetylcholine binding and not with α-bungarotoxin binding. For example, there are high levels of α-bungarotoxin binding in the hippocampus and hypothalamus and very low levels of binding throughout the thalamus (Clarke, et al., 1985). In contrast, alpha4 gene expression is highest in the thalamus, low in the hypothalamus and not detectable in the hippocampus (FIG. 4B). This makes it unlikely that the alpha4 gene codes for a component of the α-bungarotoxin binding site found in these brain areas.

The brain regions where alpha4 is expressed are known to receive cholinergic innervation (Armstrong, et al., 1983; Houser, et al., 1983; Ichikawa and Hirata,.1986). For example: (1) Cholinergic projections to the neocortex arise from the medial septal nucleus, nucleus of the diagonal band and nucleus basalis (Pearson, et al., 1983). Nicotinic receptors have been implicated in mediating at least part of the cholinergic transmission in the neocortex. Lesions of the nucleus basalis have been reported to result in supersensitivity of rat neocortical neurons to iontophoretically applied acetylcholine (Lamour, et al., 1982). This supersensitivity to acetylcholine was accompanied by an increased sensitivity to nicotine and carbachol, implying the involvement of nicotinic acetylcholine receptors. (2) The anteroventral, medial and posterior nuclei of the thalamus and the ventral lateral geniculate nucleus receive cholinergic input from the nucleus tegmentalis dorsalis lateralis (Rotter and Jacobowitz, 1981). The nucleus cuneiformis may also send some cholinergic projections to the posterior thalamic nuclei and ventrolateral geniculate nucleus. (3) The medial habenula receives cholinergic projections in part from the supracommissural septum and the nucleus of the diagonal band (Herkenham and Nauta, 1977). Furthermore, the medial habenula has a cholinergic projection via the fasciculus retroflexus to the interpeduncular nucleus (Herkenham and Nauta, 1979).

Our in situ hybridization results show that the pattern of alpha4 gene expression is different from that seen for the alpha3 gene (FIG. 5A and 5B) (Goldman, et al., 1986). It is reasonable to assume that the properties of a receptor are determined by the primary structure of the receptor protein. Thus, it seems plausible that the alpha3 and alpha4 gene products have different functional properties in these different brain regions. A possible difference is in a pre-synaptic versus post-synaptic function. One area of the rat central nervous system that has clearly been shown to contain pre-synaptic nicotinic acetylcholine receptors is the substantia nigra pars compacta. This area of the brain contains dopaminergic cells which project to the striatum, and whose cell bodies and terminals contain nicotinic receptors. Nicotine or acetylcholine bind to these receptors to stimulate dopamine release and turnover in the striatum (Lichtensteiger, et al., 1982; Sakurai, 1982).

Another area of the brain likely to contain pre-synaptic acetylcholine receptors is the interpeduncular nucleus (Brown, et al., 1984). The medial habenula sends a cholinergic projection to the interpeduncular nucleus via the fasciculus retroflexus. Stimulation of the acetylcholine receptors found on the terminals of the fasciculus retroflexus result in a depression of the pre-synaptic action potential found in the interpeduncular nucleus. Nicotine mimics, while nicotinic antagonists block, the depression of the pre-synaptic action potential caused by acetylcholine or carbachol. Therefore, these results indicate that at least some of the nicotinic acetylcholine receptors found in the interpeduncular nucleus are pre-synaptic (Brown, et al., 1984).

It is interesting that both the substantia nigra pars compacta and the medial habenula synthesize pre-synaptic nicotinic receptors and hybridize to cDNAs corresponding to the alpha3 and alpha4 gene products (FIGS. 4A & B and 5A & B) (Goldman, et al., 1986). In situ hybridization experiments demonstrated that the alpha3 gene is expressed predominantly in the medial habenula, substantia nigra pars compacta and ventral tegmental area (Goldman, et al., 1986), while the alpha4 gene is also expressed in these areas among others (FIG. 4A & B). One possibility is that the alpha3 gene encodes an alpha subunit of a pre-synaptic receptor found in these brain areas, while the alpha4 gene encodes alpha subunits of post-synaptic receptors found in these and other areas of the central nervous system.

The alpha subunits of muscle nicotinic acetylcholine receptors have domains that are thought to correspond to specific functional features of the molecule. Specifically, there are four domains in the mature molecule which are particularly hydrophobic and which are sufficiently long to span the cell membrane in an alpha-helical configuration. These domains are also found in the proteins encoded by the alpha3 gene and now the alpha4 gene reported here. The amphipathic helix in the Torpedo electric organ acetylcholine receptor, first described by Finer-Moore and Stroud (1984) and Guy (1984), is also conserved among the muscle and neural alpha subunits. While the exact amino acid sequences are not conserved, the amphipathic nature is well conserved. The fact that these specific domains are conserved suggests that these portions of the molecule play important roles in receptor function.

The deduced amino acid sequence of the muscle alpha subunit contains four cysteine residues (at amino acid positions 128, 142, 192 and 193) in the region thought to be extracellular. Cysteines 192 and 193 are known to be in the vicinity of the acetylcholine binding site because they are labeled by the affinity reagent MBTA (Kao, et al., 1984). In addition, the muscle alpha subunit contains a potential glycosylation site at Asn141 in all species examined to date. The four cysteines and asparagine (Asn141) are conserved in the alpha4 sequence. In addition to Asn141, both neuronal alpha subunits, alpha3 and alpha4, have a potential glycosylation site at Asn24. Thus, glycosylation at Asn24 may be a marker for neuronal nicotinic receptors.

Part of the α-bungarotoxin binding site on the muscle nicotinic acetylcholine receptor has been mapped to amino acid residues 173–204 (Wilson et al., 1985; Mulac-Jericevic and Atassi, 1986). Furthermore, a synthetic peptide corresponding to residues 185–196 of the Torpedo electric organ alpha subunit has been shown to bind, with low affinity, α-bungarotoxin in dot blot assays (Neumann, et al., 1986). This region of the neural alpha3 and alpha4 sequences, when compared to the muscle alpha subunit sequence, contains many none-conservative substitutions (FIGS. 3A and 3B. This may explain the observation that alpha-bungarotoxin inactivates the muscle nicotinic acetylcholine receptor but not all mammalian neuronal nicotinic receptors (Clarke, et al., 1985; Patrick and Stallcup, 1977b; Sugiyama and Yamashita, 1986).

The work from a number of laboratories has provided evidence that the brains of some non-mammalian species contain proteins with functional or structural homology to the nicotinic acetylcholine receptor. Hermans-Borgmeyer, et al. (1986) have isolated a cDNA clone from *Drosophilia* that codes for a protein with sequence homology to the nicotinic acetylcholine receptor. Hanke and Breer (1986) have isolated a protein from locusts which functions as a nicotinic receptor when reconstituted into lipid bilayers. Putative nicotinic receptors have been isolated from chick brain (Conti-Tronconi, et al., 1985; Whiting and Lindstrom, 1986) and localized by immunohistochemical methods (Swanson, et al., 1983b; Smith, et al., 1986). The relationship of these neuronal receptors to the gene family identified in this experimental section remains to be elucidated.

SUMMARY

In conclusion, this experimental section shows that heterogeneity exists in nicotinic acetylcholine receptor alpha subunits expressed in the mammalian central nervous system. This heterogeneity arises from the expression of different genes encoding the alpha subunits of the receptors (alpha3 and alpha4) and from alternative processing of the primary transcript (represented by clones 4.1 and 4.2). Based upon structural and sequence homology with the muscle alpha subunit, it is believed that the alpha4 gene encodes an alpha subunit protein. The areas of the central nervous system where the alpha4 gene is expressed are consistent with the proposal that alpha4 codes for an alpha subunit of a nicotinic receptor system in the mammalian central nervous system.

EXPERIMENTAL PROCEDURES

RNA Isolation

RNA was isolated as previously described (Goldman, et al., 1985). Briefly, 1–2 grams of tissue were homogenized in buffered guanidine thiocyanate. After clarification, the homogenate was layered over a cushion of CsCl and centrifuged 15 hours at 35,000 rpm in a Beckman SW41 rotor. The RNA pellet was resuspended in water to which guanidine hydrochloride was added and then ethanol precipitated. The RNA precipitate was resuspended in water and ethanol precipitated again. Poly(A)$^+$ RNA was selected by chromatography over an oligo(dT)-cellulose column (Aviv and Leder, 1972).

Construction and Screening of cDNA Libraries

Two cDNA libraries were constructed using poly(A)+ RNA isolated from the hippocampus or a hypothalamic punch. The method of Gubler and Hoffman (1983) was used to prepare size-fractionated double-stranded cDNA. The cDNA was ligated to phosphorylated EcoRI linkers and cloned into the EcoRI site of bacteriophage λgt10 (Huynn, et al., 1985). Approximately $5 \times 10^5$ plaques were screened from each library with a radiolabeled cDNA fragment coding for the mouse muscle acetylcholine receptor alpha subunit (Boulter, et al., 1985), as well as a probe made from the cDNA coding for the alpha3 gene product (Boulter, et al., 1986).

DNA Sequence Determination

DNA sequencing was performed using the dideoxynucleotide chain termination method of Sanger, et al., (1977). cDNAs were subcloned into M13 bacteriophage vectors mp18 and mp19. Deletions were generated by the method of Dale, et al., (1985).

RNA Blots

RNA was denatured in formaldehyde at 65° C. and electrophoresed in 2.2M formaldehyde, 1.4% agarose gels. The RNA was then transferred to a Gene Screen Plus membrane. Prehybridization and hybridization conditions were 5× SSPE (0.75 M NaCl, 57 mM $Na_2HPO_4$, 5 mM EDTA, pH 7.4), 1% SDS, 10% dextran sulfate, and 50% formamide at 42° C. After hybridization, the blot was washed in 0.2× SSPE, 1% SDS at 65° C. and was exposed to X-ray film with an intensifying screen at −70° C.

S1 Nuclease Analysis

Nuclease S1 digestions of heteroduplexes formed between poly(A)+ RNA and M13 subclones of the alpha4 cDNA clone were carried out as described (Goldman, et al.., 1985). The 3' 596 nucleotides of the alpha4 cDNA were subcloned into M13mp18 and the single-strand viral DNA was used to form heteroduplexes. Those hybrids surviving S1 nuclease digestion were analyzed by electrophoresis through a 3% polyacrylamide-8M urea gel, electroblotted to Gene Screen Plus and detected by hybridization to nick-translated radiolabeled alpha4 cDNA.

In situ Hybridization

In situ hybridization was performed as previously described (Cox, et al., 1984; Goldman, et al., 1986). Briefly, brain sections mounted on polylysine coated slides were treated with proteinase K, acetylated with acetic anhydride and dehydrated prior to hybridization. Sections were hybridized with single strand radiolabeled RNA probes prepared from an SP6 vector containing a cDNA insert encoding either the alpha3 or alpha4 gene product. Hybridization was performed at 42° for 14–18 hours. Post-hybridization treatments included RNase A digestion and a final wash in 0.1× SSPE at 65° C. Slides were dehydrated and exposed to X-ray film at room temperature for 3–20 days.

Sequence Alignment and Homology Calculations

Protein sequences were aligned using an INTELLIGENETICS software IFIND program that utilizes an algorithm developed by Wilbur and Lipman (1983). Parameters were set to default values. Alignments were adjusted by visual inspection. Homology percentages were calculated by dividing the number of identical residues by the number of residues in the shorter of the two sequences being compared.

Analysis of Amphipathic Character

Helical wheel plots were used to analyze potential amphipathic character (Schiffer and Edmundson, 1967).

FIGURE LEGENDS

Experimental Section I

FIG. 1. Line diagram illustrating the relationship of alpha clones 4.1 and 4.2 to each other. The 4.2 cDNA sequence begins at nucleotide 389 of clone 4.1 (marked by arrow). Clone 4.2 is identical to 4.1 up to nucleotide 1871 after which the two sequences diverge (illustrated by wavy line).

FIGS. 2A to 2F Nucleotide and deduced amino acid sequence of alpha cDNA clone 4.1 and the unique 3' sequence of alpha clone 4.2. Arrows indicate where the two sequences diverge from each other. Nucleotides are numbered in the 5' to 3' direction beginning with the first base of the cDNA.

FIGS. 3A and 3B. Alignment of deduced amino acid sequences for acetylcholine receptor alpha subunits from the mouse muscle cell line, BC3H-1 (alpha1, clone 1BMA407) (Boulter, et al, 1985), the rat neuronal cell line, PC12 (alpha3, clone lPCA48) (Boulter, et al., 1986) and the rat brain (alpha4, clone 4.2). Amino acids are boxed when the amino acid present in alpha4 is also present in either alpha1 or alpha3. Hydrophobic, putative membrane spanning regions (MSR) and the potential amphipathic helix are indicated below the aligned sequence. Asterisks indicate potential glycosylation sites and arrows indicate conserved cysteine residues.

FIG. 4 (A & B). Mapping brain areas expressing RNA homologous to alpha clones 4.1 and 4.2 by in situ hybridization. Brain sections were hybridized with radiolabeled RNA corresponding to full-length alpha 4.1 cDNA in the (A) antisense or (B) sense orientation. The sense orientation serves as a control for nonspecific hybridization. AM, anteromedial thalamic nucleus; ARC, arcuate hypothalamic nucleus; AV, anteroventral thalamic nucleus; C, neocortex; CM, central medial thalamic nucleus; DLG, dorsal lateral geniculate nucleus; LD, laterodorsal thalamic nucleus; LH, lateral hypothalamic area; LPO, lateral preoptic area; MG, medial geniculate nucleus; MH, medial habenula; MPO, medial preoptic area; Po, posterior thalamic nuclear group; PVA, paraventricular thalamic nucleus, anterior; RsPl, retrosplenial cortex; RT, reticular thalamic nucleus; NC, substantia nigra pars compacta; VL, ventrolateral thalamic nucleus; VLG, ventral lateral geniculate nucleus; VMH, ventromedial hypothalamic nucleus; VP, ventroposterior thalamic nuclei; VPM, ventro posterior thalamic nuclei, medial area; VTA, ventral tegmental area.

FIGS. 5 (A & B). Comparison of alpha3 and alpha4 gene expression in rat brains by in situ hybridization. Brain sections were hybridized with radiolabeled RNA made from cDNAs corresponding to the products of the alpha3 gene (A) or the alpha4 gene (B).

FIGS. 6 (A & B). S1 nuclease protection experiment. (A) Fragment of alpha clone 4.1 cDNA subcloned into M13. The fragment is 596 bases long, and the 5' 406 bases are the same in alpha clones 4.1 and 4.2. (B) Gel profile of S1 nuclease protected fragments generated by S1 nuclease digestion of heteroduplexes formed between poly(A)+ RNA isolated from the indicated areas of the central nervous system and the M13 subclone shown in (A). Control lanes lack RNA during the hybridization.

EXPERIMENTAL SECTION II

PRIMARY STRUCTURE AND EXPRESSION OF BETA2

INTRODUCTION

Nicotinic acetylcholine receptor subunits are encoded by the members of a gene superfamily that includes the glycine and λ-aminobutyric acid (GABA) receptor subunits (Grenningloh, et al., 1987; Schofield, et al., 1987). The nicotinic acetylcholine receptor of the Torpedo electric organ is known to be a pentameric structure composed of homologous subunits with the stoichiometry: α1 α1 βλδ (for review, see Stroud and Finer-Moore, 1985). The nicotinic receptors that mediate the excitation of skeletal muscle are also thought to have a similar structure, since subunits similar to the electric organ receptor subunits have been found in muscle (for review, see Schuetze and Role, 1987). In contrast, much less is known about the nicotinic acetylcholine receptors that mediate synaptic transmission in the peripheral and central nervous systems. However, it is clear that the "neuronal" receptors are pharmacologically distinguishable from the muscle nicotinic receptors and may constitute a family of subtypes (for review, see Martin, 1986).

As discussed in other parts of this specification, our group has used the molecular genetic approach to identify and characterize neuronal nicotinic acetylcholine receptors. The isolation of rat genomic and cDNA clones defined the homologous genes alpha2 (K. Wada, et al., 1988), alpha3 (Boulter, et al., 1986), alpha4 (Goldman, et al., 1987) and alpha5. In situ hybridization histochemistry has shown that each of these genes exhibits a different pattern of expression in the brain, suggesting that they encode subunits of different neuronal nicotinic receptors.

The primary structures of the proteins encoded by the alpha2, alpha3, alpha4 and alpha5 genes have features found in the subunits of the Torpedo electric organ and vertebrate muscle nicotinic acetylcholine receptors. One of these features is the presence of two adjacent cysteine residues in the presumed extracellular domain; a feature common to the agonist-binding alpha1 subunits, but not the beta, gamma, and delta subunits of the electric organ and muscle receptors. These cysteine residues have been shown to be close to the agonist-binding site within the alpha subunits (Kao, et al., 1984; Kao and Karlin, 1986). Thus, it is believed that the alpha2, alpha3, alpha4 and alpha5 genes encode agonist-binding subunits of neuronal receptors.

The structures of the neuronal receptors are not known, but one possibility is that they are composed of identical subunits. To test this idea, a single mRNA species encoding either the alpha2, alpha3, or alpha4 subunits was injected into oocytes. Voltage depolarizations could not be detected in oocytes injected with either alpha2 or alpha3 mRNAs. Responses to acetylcholine could be detected in oocytes injected with alpha4 mRNA, but this response was weak and occurred infrequently (Boulter, et al., 1987). This suggests that, like the electric organ and vertebrate muscle receptors, neuronal receptors are heterooligomers.

This experimental section discloses the primary structure of a protein that is homologous to the neuronal alpha subunits but lacks the two adjacent cysteine residues, shown to be near the agonist-binding site. In this respect, the protein is similar to the beta, gamma, and delta subunits of the electric organ and muscle receptors. In addition, this experimental section provides additional evidence that this protein can functionally substitute for the muscle beta subunit in a nicotinic receptor. Thus, the name beta2 has been given to this protein. In our terminology, beta1 corresponds to the beta subunits of the electric organ and muscle receptors. Expression studies have shown that three types of functional neuronal nicotinic acetylcholine receptors are produced upon co-injection of beta2 mRNA and each of the neuronal alpha2, alpha3, and alpha4 mRNAs. These results, together with the distribution of beta2 transcripts in the brain are consistent with the idea that different neuronal nicotinic acetylcholine receptors are composed of beta2 subunits and different agonist-binding alpha subunits.

RESULTS

Isolation of the Beta2 cDNAs

Figure 7A:
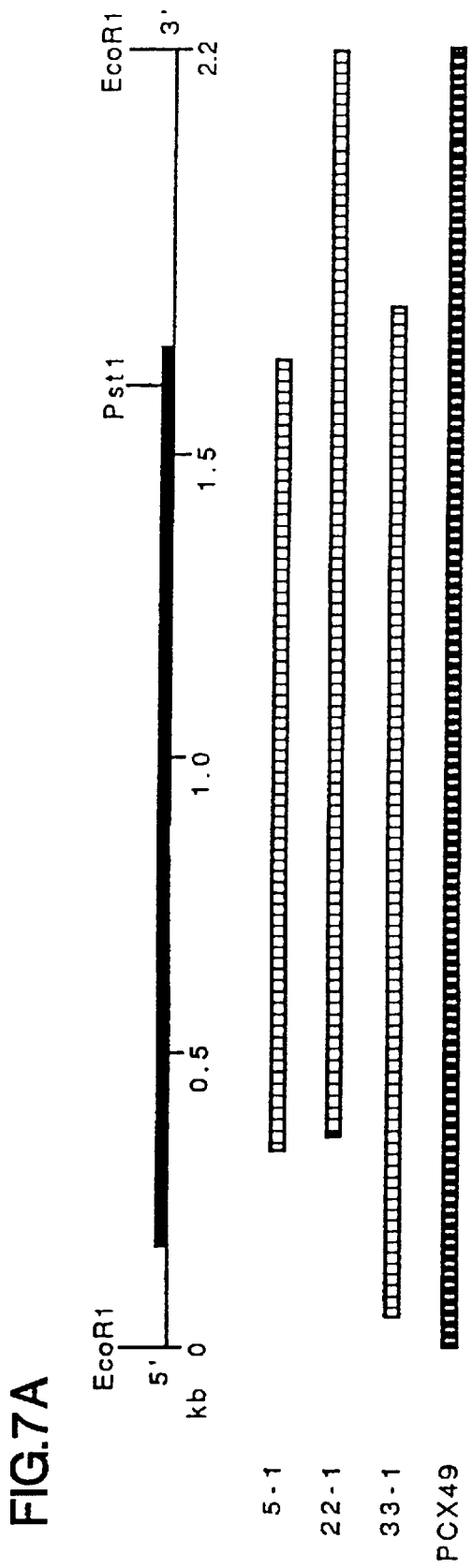

To determine whether additional subunits other than the alpha2, alpha3, and alpha4 subunits are required to produce functional neuronal nicotinic acetylcholine receptors, cDNA libraries were screened to find clones encoding new subunits. In situ hybridization histochemistry has shown that transcripts encoding the alpha2 (K. Wada, et al., 1988), alpha3 (Boulter, et al., 1986), and alpha4 (Goldman, et al., 1987) subunits are present in the rat brain. Thus, λgt10 cDNA libraries were prepared from poly(A)+ RNA isolated from different regions of the brain. One such library prepared from poly(A)+ RNA isolated from the hypothalmic region of the brain was screened with a radiolabeled probe made from a cDNA encoding the alpha3 subunit. Screening $5 \times 10^5$ recombinants resulted in the isolation of clones, 15-1 (1324 bp), 122-1 (1834 bp), and 133-1 (1706 bp) (FIG. 7A), encoding a protein related to, but different from, the alpha2, alpha3 and alpha4 subunits. As described previously (Boulter et al., 1986), transcripts encoding the alpha3 subunit are also present in the rat adrenal chromaffin tumor cell line, PC12. This cell line expresses a "ganglionic" nicotinic acetylcholine receptor of the type found in sympathetic neurons (Patrick and Stallcup, 1977b). Thus, a λgt10 cDNA library prepared from PC12 cell poly(A)+ RNA was screened to determine whether related clones could be found in this library. Screening $1 \times 10^6$ recombinants with a probe made from clone 15-1 resulted in the isolation of several clones, one of which, 1PCX49 (2196bp), was chosen for further study (FIG. 7A). Nuclease S1 protection analysis (data not shown) revealed that 1PCX49 is colinear with the clones isolated from the brain cDNA library.

Primary Structure of the Beta2 Subunit

Of the four cDNAs isolated, 1PCX49 extended furthest in both the 5' and 3' directions. The nucleotide sequence of 1PCX49 and 15-1 was determined for both strands and is shown along with the deduced amino acid sequence in FIG. 7B(1)–7B(3). An open reading frame of 1509 nucleotides is present that is bounded by an ATG codon at position 1 and an TGA stop codon at position 1510. Thus, the encoded protein is 503 amino-acid residues in length, with a calculated molecular mass of 57,321 daltons. Flanking the open reading frame is a 5' untranslated region of 179 bp and a 3' untranslated region of 507 bp. Neither a consensus polyadenylation signal sequence nor a polyA tract is present, suggesting that the 3' untranslated region extends beyond the sequence present in the cDNA clone, 1PCX49.

Examination of the primary structure of the beta2 protein indicates that it is a member of the neurotransmitter-gated ion-channel subunit superfamily. It is more related to the alpha3 and alpha4 neuronal nicotinic acetylcholine receptor subunits (approximately 50% sequence identity) than to any of the subunits of the mouse muscle nicotinic acetylcholine receptor (approximately 40% sequence identity) or the glycine and GABA receptor subunits (approximately 20% sequence identity). The algorithm of Kyte and Doolittle (1982) revealed four potential transmembrane domains (TMD I–IV) that are features common to the members of the superfamily (FIG. 8). Between the predicted signal peptide domain (the method of Von Heijne, 1986 was used to predict a signal peptide of 28 residues) and the first potential membrane spanning domain is an N- terminal hydrophilic segment thought to be an extracellular domain of the protein. Within this hydrophilic segment are two potential N-linked glycosylation sites (FIG. 8). These residues are conserved in the neuronal alpha3 and alpha4 subunits; only the site nearer to the carboxy-terminus is conserved in the mouse muscle alpha1 subunit. A potential N-linked glycosylation site that is not conserved in the alpha1, alpha3, and alpha4 subunits is present eighteen residues from the carboxy-terminal end of the protein (FIG. 8). The possible presence of a carbohydrate chain at the carboxy-terminal end of the beta2 protein is consistent with one model (Claudio, et al., 1983) of receptor subunit organization that places the carboxy-terminus in the extracellular domain.

Another feature the beta2 subunit shares with members of the neurotransmitter-gated ion-channel subunit superfamily is the presence in the N-terminal hydrophilic domain of two cysteine residues (FIG. 8) that correspond to residues 128 and 142 of the Torpedo electric organ alpha subunit (Noda, et al., 1982). All alpha subunits sequenced to date have adjacent cysteine residues in the presumed extracellular domain. These residues correspond to cysteines 192 and 193 of the Torpedo electric organ alpha subunit (Noda, et al., 1982) and are near the agonist-binding site (Kao and Karlin, 1986). In contrast, the beta2 subunit lacks two adjacent cysteine residues in the presumed extracellular domain (FIG. 8). In this respect, beta2 is similar to the beta1, gamma, and delta subunits of the Torpedo electric organ and the vertebrate muscle receptors. Based upon the absence of adjacent cysteine residues, the beta2 protein is proposed to be a non-agonist-binding subunit of nicotinic acetylcholine receptors.

Expression of Functional Neuronal Nicotinic
Acetylcholine Receptors

A test was made to determine whether functional nicotinic acetylcholine receptors can be produced in *Xenopus* oocytes after the pairwise injection of mRNA encoding the beta2 subunit and mRNA encoding either the alpha2, alpha3, or alpha4 subunits (Boulter, et al., 1987; K. Wada, et al., unpublished data). Oocytes injected with beta2 mRNA and either of the neuronal alpha3 or alpha4 mRNAs exhibited strong and reproducible membrane depolarizations in response to acetylcholine (Table 1) and nicotine (Boulter et al., 1987). These acetylcholine receptors were blocked by the ganglionic nicotinic receptor blocked bungarotoxin 3.1, but not by the neuromuscular junction nicotinic receptor blocked alpha-bungarotoxin (Boulter, et al., 1987). This pharmacology is characteristic of the ganglionic nicotinic acetylcholine receptors found in chick ciliary ganglion neurons (Ravdin and Berg, 1979), rat sympathetic neurons (Chiappinelli and Dryer, 1984) and PC12 cells (Patrick and Stallcup, 1977). Oocytes injected with the combination of alpha2 and beta2 mRNA (Table 1) also gave strong and reproducible depolarizing responses to acetylcholine and nicotine; however, this receptor was not sensitive to functional blockade by either bungarotoxin 3.1 or α-bungarotoxin (K. Wada, et al., 1988). Thus, some neuronal nicotinic acetylcholine receptors may be resistant to functional blockade by bungarotoxin 3.1, although this pharmacology has not been reported in vivo.

Evidence that the Beta2 Subunit Can Functionally
Substitute for the Muscle Beta1 Subunit The absence of two adjacent cysteine residues is a structural feature that the beta2 protein shares with the non-agonist-binding beta1, gamma, and delta subunits of the Torpedo electric organ and mouse muscle nicotinic acetylcholine receptors. This feature suggests that the beta2 protein functions as a non-agonist-binding subunit. To examine this hypothesis, a test was made to determine whether the beta2 subunit could substitute for one of the mouse muscle receptor subunits. This was done by injecting into *Xenopus* oocytes various combinations of mRNA encoding the beta2 subunit and the muscle receptor subunits ($\alpha 1$, $\beta 1$, $\lambda$, and $\delta$). The oocytes were then tested for the expression of functional receptors by recording acetylcholine-evoked voltage depolarizations.

Injection of all four of the muscle receptor subunit mRNAs ($\alpha 1$, $\beta 1$, $\lambda$, and $\delta$) gave rise to strong functional expression (Table 2). Omitting $\beta 1$ mRNA, so that only $\alpha 1$, $\lambda$, and $\delta$ mRNAs were injected resulted in either very weak or undectectable responses to acetylcholine. However, strong responses to acetylcholine could be detected by co-injecting beta2 mRNA with $\alpha 1$, $\lambda$, and $\delta$ mRNAs, although these responses were not as strong as those detected in oocytes injected with all four mouse muscle subunit mRNAs. The reproducibility with which acetylcholine-evoked voltage depolarizations were detected in oocytes injected with the above combinations is shown in Table 3. It is evident that co-injection of $\beta 2$ mRNA with $\alpha 1$, $\lambda$, and $\delta$ mRNAs restores the reproducibility of the acetylcholine responses to that seen with oocytes injected with all four muscle subunit mRNAs. These results, presented in Tables 2 and 3, indicate that the beta2 subunit can substitute for the muscle beta1 subunit in the formation of an acetylcholine receptor.

It is possible that the beta2 subunit can substitute for other muscle subunits as well. To investigate this possibility, oocytes were injected with additional combinations of beta2 and muscle subunit mRNAs (Table 3). It was found that injection of beta2 mRNA alone does not give rise to detectable acetylcholine sensitivities. Therefore, the beta2 subunit by itself cannot account for the observed effect. Acetylcholine-evoked voltage depolarizations were not detectable in oocytes injected with the mouse muscle alpha1 mRNA and beta2 mRNA, indicating that the beta2 subunit cannot substitute for all three muscle non-alpha subunits. Apparently the alpha1 and beta2 subunits are unable to form a receptor in a manner analogous to the neuronal receptors.

A further test was made to determine whether the beta2 subunit could substitute for either the gamma or delta subunits. This experiment was based on two observations: (1) injection of alpha1 and beta1 mRNAs into oocytes does not result in detectable depolarizing responses to acetylcholine and (2) if this mRNA mixture is supplemented with either gamma or delta mRNA, then strong and reproducible responses are detected (data not shown). To test the idea that the beta2 subunit can substitute for either the gamma or delta subunits, alpha1, beta1, and beta2 mRNA was injected into oocytes. As shown in Table 3, it was not possible to detect responses to acetylcholine in any of the oocytes injected with this combination of mRNAs. Thus, the beta2 subunit apparently cannot substitute for either the gamma or delta subunits.

To determine whether the receptor produced upon co-injection of the muscle subunit mRNAs and the beta2 mRNAs requires alpha1 mRNA, oocytes were injected with beta2, gamma, and delta mRNAs. Responses to acetylcholine were not detected. This indicates that the alpha1 subunit is required for functional expression and that the beta2 subunit cannot substitute for both the alpha1 and beta1 subunits.

The observation (unpublished) that injection of beta1, gamma and delta mRNAs does not result in the detection of functional receptors was used to test whether the beta2 subunit can substitute for the alpha1 subunit. Oocytes were injected with beta2, beta1, gamma and delta mRNAs and tested for depolarizing responses to acetylcholine. In each oocyte injected with this combination of mRNAs, acetylcholine was unable to evoke detectable depolarizing responses. Thus, there is no evidence that the beta2 subunit can functionally substitute for the agonist-binding alpha1 subunit. This is consistent with the idea that the beta2 subunit is not an agonist-binding subunit.

The receptor produced in oocytes injected with alpha1, beta2, gamma, and delta mRNAs is nicotinic; depolarizations could be elicited by 1 mM nicotine and were blocked by 100 mM d-tubocurarine. Furthermore, the receptor exhibits the pharmacology of a muscle nicotinic receptor, in that incubation of oocytes with 0.1 mM α-bungarotoxin for 30 minutes completely blocked the response to 10 mM acetylcholine (data not shown).

The results presented in Tables 2 and 3 demonstrate that beta2 mRNA can contribute to the strong and reproducible expression of a nicotinic acetylcholine receptor in combination with the mouse muscle alpha1, gamma, and delta mRNAs. The simplest interpretation is that the beta2 protein functionally substitutes for the mouse muscle beta1 subunit. Together with the structural considerations discussed above, these results suggest the beta2 protein functions as a non-agonist-binding subunit in neuronal nicotinic acetylcholine receptors.

Beta2 RNA Expression in the Rat Nervous System

The expression studies performed in oocytes suggest that the beta2 gene encodes a subunit common to a family of nicotinic receptors in the nervous system. To provide additional evidence for this idea, an examination was made to determine whether beta2 mRNA co-localizes with mRNA encoding the alpha2, alpha3, and alpha4 subunits.

Figure 9B:
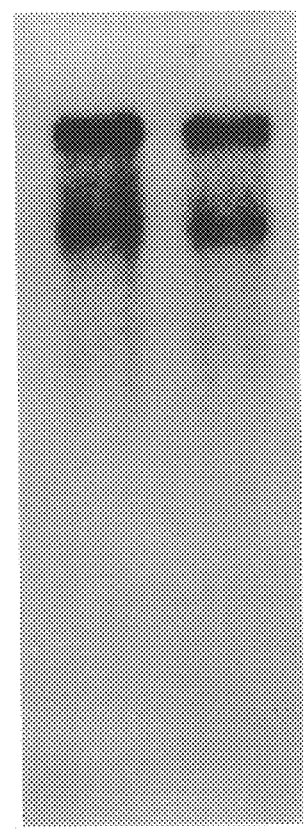

Previously, alpha3 mRNA was shown to be present in PC12 cells and has been proposed to encode a subunit of the nicotinic acetylcholine receptor expressed in these cells (Boulter, et al., 1986). In addition, it has been shown that alpha3 (Boulter, et al., 1986; Goldman, et al., 1986) and alpha4 (Goldman, et al., 1987) mRNA is present in the central nervous system. Northern blot analysis was used to determine whether beta2 mRNA co-localizes with alpha3 mRNA in PC12 cells and with alpha3 or alpha4 mRNA in the central nervous system. Poly(A)+ RNA isolated from PC12 cells, thalamus and spinal cord was size fractionated and transferred to a Gene Screen Plus nylon membrane. To minimize cross-hybridization of the beta2 sequence with other members of the nicotinic acetylcholine receptor gene family, a [$^{32}$P]-radiolabeled probe was prepared using a PstI-EcoRI 571 bp fragment of clone PCX49 that corresponds to mostly 3' untranslated sequence (see FIG. 7A). Hybridizing species of approximately 3.9 kb and 5.7 kb were detected in RNA obtained from PC12 cells (FIG. 9A) and both central nervous system regions (FIG. 9B).

To determine more precisely the distribution of beta2 transcripts within the central nervous system, in situ hybridization histochemistry was used. Radiolabeled antisense or sense RNA probes were transcribed in vitro from a plasmid in which the PstI-EcoRI 571 bp fragment of PCX49 was subcloned between the SP6 and T7 promoters. FIGS. 10 (A & B) shows the results of hybridization of antisense and sense (to assess background labeling) RNA to paraformaldehyde-fixed sections of adult rat forebrain and midbrain. The antisense RNA probe hybridized to regions throughout the forebrain and midbrain. The most intense labeling occurred in the piriform cortex, olfactory tubercle, hippocampal region (dentate gyrus, Ammon's horn, and subiculum), thalamus, supraoptic hypothalamic nucleus, and interpeduncular nucleus. In addition, many other structures, including the neocortex, striatum, ventromedial hypothalamic nucleus, and substantia nigra pars compacta were labeled, although to a lesser extent. This pattern of hybridization was also seen when rat brain sections were probed with [$^{35}$S]-radiolabeled antisense RNA corresponding to the 5' 1238 bp of PCX49 (data not shown). Examination of emulsion dipped sections revealed that the beta2 RNA probe accumulated over neurons. Glia, fiber tracts and the ependyma appeared to be free of labeling (E. Wada, et al., unpublished data). Thus, beta2 transcripts appear to be found in all of the general regions where alpha2 (K. Wada, et al., unpublished data), alpha3 (Goldman, et al., 1986), and alpha4 (Goldman, et al., 1987) transcripts are found. This result is consistent with the idea that in different areas of the nervous system distinct forms of neuronal nicotinic acetylcholine receptors are produced by combining beta2 subunits with different agonist- binding alpha subunits.

DISCUSSION

Our group has identified four genes, alpha2 (Wada, et al., 1988 and this specification), alpha3 (Boulter, et al., 1986), and alpha4 (Goldman, et al., 1987 and this specification) and alpha5 (this specification) proposed to encode agonist-binding alpha subunits of different neuronal nicotinic acetylcholine receptors. Expression studies in *Xenopus* oocytes suggested that, in addition to the alpha subunits, other subunits are required to form functional neuronal receptors. In this experimental section, the primary structure of a protein is described that is homologous to the neuronal alpha subunits but lacks two adjacent cysteine residues shown to be near the agonist-binding site. This protein, beta2, is therefore similar to non-agonist-binding subunits of the electric organ and muscle nicotinic acetylcholine receptors. The results of oocyte expression studies and the localization of beta2 transcripts are consistent with the idea that the beta2 protein is a subunit common to different neuronal nicotinic acetylcholine receptors expressed in the peripheral and central nervous systems.

Nucleotide sequence analysis has revealed that the beta2 subunit contains specific structural features found in members of the neurotransmitter-gated ion-channel subunit superfamily. These include a large hydrophilic amino-terminal domain that contains two cysteine residues that correspond to the Torpedo alpha subunit cysteine residues 128 and 142 (Noda, et al., 1982), and four hydrophobic segments that presumably form transmembrane domains. The beta2 subunit exhibits greater sequence identity to the neuronal alpha3 and alpha4 subunits than with the other members of the superfamily. The closer similarity to the neuronal alpha3 and alpha4 subunits, together with the distribution of its mRNA in the nervous system, indicates that the beta2 gene encodes a neuronal nicotinic acetylcholine receptor subunit.

Torpedo electric organ and muscle nicotinic acetylcholine receptors are composed of α1-α1-β1-λ-δ subunits. The alpha subunits can be distinguished from the beta, gamma, and delta subunits by the fact that they are labeled by affinity alkylating reagents such as 4-(N-maleimido) benzyltrimethyl-ammoniumiodide (MBTA) (Weill, et al., 1974). Thus, alpha subunits but not beta, gamma, and delta subunits contain the agonist-binding site. The covalent binding of these reagents depends upon the prior reduction of a disulfide bond (Karlin, A., 1969). It has been shown for the Torpedo alpha subunit that the residues involved in the covalent link to MBTA are cysteines 192 and 193 (Kao, et al., 1984; Kao and Karlin, 1986). Thus, these residues lie close to the agonist-binding site of the receptor. In the beta, gamma, and delta subunits these two adjacent cysteine residues are not conserved, consistent with the failure of MBTA to label these subunits. In this respect, the beta2 subunit is similar to the beta1, gamma, and delta subunits of the Torpedo electric organ and muscle receptors, suggesting that it functions as a non-agonist-binding subunit. The experiments presented here indicate that the beta2 subunit will substitute specifically for the mouse muscle beta1 subunit in the expression of a nicotinic acetylcholine receptor, thus providing functional evidence that the beta2 protein is a non-agonist-binding subunit.

The functional expression in oocytes of three neuronal nicotinic acetylcholine receptors by the combination of the beta2 gene product with each of the neuronal alpha subunit gene products suggests a promiscuous function for the beta2 subunit. This raises an important question regarding the beta2 gene: does the beta2 gene encode a protein that is a subunit common to a family of nicotinic acetylcholine receptors in the nervous system? The expression studies indicate that this is clearly possible from a functional point of view. Still, it is possible that the promiscuous nature of the beta2 subunit is only evident in the oocyte system where one can create adventitious subunit combinations that are not present in vivo. However, the pattern of beta2 RNA expression in the nervous system supports the idea that receptors composed of alpha2/beta2, alpha3/beta2, and alpha4/beta2 subunits are be made in the nervous system. Both alpha3 and beta2 transcripts are found in a cell line, PC12, that expresses a neuronal nicotinic acetylcholine receptor. The receptor in PC12 cells and the receptor formed by the combination of the alpha3 and beta2 gene products in oocytes share similar pharmacological properties. Bungarotoxin 3.1 functionally blocks both the PC12 cell receptor (J. Patrick, unpublished observation) and the alpha3/beta2 receptor (Boulter, et al., 1987), but neither of these receptors are functionally blocked by alpha-bungarotoxin (Patrick and Stallcup, 1977; Boulter, et al., 1987). In addition, it has been shown that beta2 RNA is localized in regions of the brain where alpha2 (Wada, et al., 1988), alpha3 (Goldman, et al., 1986), and alpha4 (Goldman, et al., 1987) RNA is found, most notably in the thalamus. One of the regions of the thalamus showing intense labeling by the alpha3, alpha4, and beta2 RNA probes is the medial habenular nucleus. This region has been shown to respond to the application of acetylcholine and nicotine (but not muscarinic agonists) by causing a rapid excitation due to an increase in membrane conductance. This effect was blocked by hexamethonium but not by atropine and was interpreted to indicate the presence of a nicotinic acetylcholine receptor (McCormick and Prince, 1987). Thus, the response to acetylcholine in the medial habenular nucleus may be mediated by receptors composed of beta2 subunits in combination with either or both of the alpha3 or alpha4 subunits.

Further evidence consistent with the idea that the neuronal receptors are composed of a beta2 subunit and either alpha2, alpha3, or alpha4 subunits comes from correlations of in situ hybridization mapping with in situ mapping of radiolabeled cholinergic agonist binding (Clarke, et al., 1985) and immunohistochemical studies (Swanson, et al., 1987). [$^3$H]-acetylcholine and [$^3$H]-nicotine were used to identify high affinity binding sites in the rat brain. Most of the regions labeled by [3H]-agonists correspond to regions labeled by both beta2 and alpha4 RNA probes. High affinity binding sites for these radiolabeled agonists are also found in regions where beta2 transcripts colocalize with alpha2 and alpha3 transcripts, for example, the interpeduncular nucleus (K. Wada, et al., unpublished data). Immunohistochemical studies (Swanson, et al., 1987) have been performed using a monoclonal antibody (mAb270) that has been used to purify a nicotine binding site from rat brain (Whiting and Lindstrom, 1987a). The binding pattern of mAb270 was similar to that of [$^3$H]-agonists. Thus, the pattern of mAb270 binding closely matched the distribution of alpha2, alpha3, alpha4 and beta2 transcripts. This suggests that [$^3$H]-agonists and mAb270 bind to receptors composed of beta2 subunits and agonist-binding alpha subunits.

Interestingly, beta2 RNA expression was also observed in regions of the central nervous system that are not labeled by [$^3$H]-agonists and mAb270, and where neither the alpha2, alpha3 nor alpha4 genes are expressed. One of these regions, the supraoptic nucleus has been reported to be labeled by [$^{125}$I]-α-bungarotoxin (Clarke, et al., 1985). α-bungarotoxin is a component in the venom of the snake *Bungarus multicinctus* that functionally blocks the neuromuscular junction nicotinic acetylcholine receptor. This toxin also binds to a component that has been purified from chick and rat brains (Conti-Tronconi, et al., 1985; Kemp, et al., 1985). However, the component is distinguishable from functional neuronal receptors; alpha-bungarotoxin does not block the function of certain nicotinic acetylcholine receptors in the peripheral and central nervous systems, (Martin, 1986) and in situ mapping studies (Clarke, et al., 1985) have shown that [$^{125}$I]-α-bungarotoxin labels many regions that lie outside those labeled by[$^3$H]-acetylcholine and [$^3$H]-nicotine. The function of the α-bungarotoxin binding component is not known, though it has been proposed to be a low affinity nicotine receptor (Wonnacott, 1986); possibly mediating at least some of the central physiological and behavioral effects of nicotine. One possibility is that the beta2 protein is also a subunit of the toxin-binding component. Alternatively, the beta2 subunit could be a component of a neuronal nicotinic acetylcholine receptor that either: (1) has an affinity for ligands too low to bind [$^3$H]-agonists in situ, (2) is transported to sites far removed from cell bodies so that there is no correspondence between mRNA and protein localization, or (3) is present in amounts insufficient for detection by [$^3$H]-agonists and mab270. In view of its functionally promiscuous nature and apparent ubiquitous transcript distribution, another formal possibility is that the beta2 protein also functions as a subunit of a non-cholinergic receptor.

The results presented here and previously (Boulter, et al., 1987; K. Wada, et al., unpublished data) do not provide direct information concerning the number of different subunits present in neuronal nicotinic receptors in vivo. However, the idea that neuronal nicotinic receptors are formed from two different subunits is supported by the recent reports of the purification of proteins from detergent extracts of chick (Whiting and Lindstrom, 1986a) and rat (Whiting and Lindstrom, 1987a) brain that exhibit the pharmacological properties (Whiting and Lindstrom,. 1986b) of a neuronal nicotinic acetylcholine receptor. These components appear to be composed in each case of two subunits. The larger of these two subunits is labeled by MBTA (Whiting and Lindstrom, 1987b), indicating that it is an agonist-binding alpha subunit. Indeed, it has recently been determined by amino-terminal micro-sequencing of purified polypeptide preparations that the larger of these two subunits corresponds to the alpha4 subunit (Whiting, et al., 1987). Amino-terminal sequence data has not been reported for the smaller molecular weight subunit. However, its failure to bind MBTA indicates that it is a non-agonist-binding subunit and thus it may be identical to the beta2 subunit.

SUMMARY

This experimental section presents the primary structure of the beta2 protein. The beta2 protein has the structural and functional characteristics of a non-agonist-binding subunit. This interpretation is based on the absence of two adjacent cysteine residues shown to be near the agonist-binding site on alpha subunits and evidence indicating that the beta2 subunit can substitute specifically for the mouse muscle beta1 subunit in a functional receptor. In light of functional expression studies, showing that beta2 mRNA in combination with either alpha2, alpha3, or alpha4 mRNA results in the formation of three different neuronal nicotinic acetylcholine receptors and the wide distribution of beta2 transcripts in the rat brain, it is proposed that the nervous system expresses different nicotinic acetylcholine receptors by combining beta2 subunits with different agonist-binding alpha subunits. Therefore, one mode of generating receptor diversity at synapses in the nervous system may be to complex a common non-agonist-binding subunit with unique agonist-binding subunits.

EXPERIMENTAL PROCEDURES

Construction and Screening of cDNA Libraries

Total RNA was obtained as previously described (Goldman, et al., 1987) or by the method of Cathala, et al. (1983). Poly(A)+ RNA was selected using an oligo-dT cellulose column (Aviv and Leder, 1972). The cDNA was synthesized by the method of Gubler and Hoffman (1983) from poly(A)+ RNA that was obtained from a rat hypothalamic punch and PC12 cells. The cDNA was ligated to phosphorylated EcoRI linkers and cloned into the EcoRI site of bacteriophage λgt10 (Huynn, et al., 1985). Approximately 5×10⁵ recombinants from the hypothalamus library and 1×10⁶ recombinants from the PC12 library were screened with a [$^{32}$P]-nick-translated PCA48 cDNA (Boulter, et al., 1986) or 15-1 insert, respectively. Filter hybridization was performed overnight in 5× SSPE, 1% SDS, 1× Denhardt's at 65° C. Filters were washed twice at room temperature for 30 min in 2× SSC and once at 65° C. for 1 hr in 0.2× SSC and 1% SDS.

Nucleotide Sequence Determination and Analysis

The cDNA of purified lambda clones was inserted into the EcoRI site of M13mp18. A nested set of overlapping M13 clones was generated by the method of Dale, et al., (1985) and sequenced by the chain termination method of Sanger, et al., (1977). Deduced amino-acid sequences were aligned with each other and percent identity was calculated by dividing the number of identical residues by the number of residues in the shorter of two subunits being compared.

In Situ Hybridization

Adult male rats were anesthetized by intraperitoneal injection of 35% chloral hydrate (0.1lm/100 g body weight). Brain tissue was fixed by perfusion with 4% paraformaldehyde/ 0.05% glutaraldehyde. After perfusion, the brain was removed and placed in post-fix solution which consisted of 4% paraformaldehyde plus 10% sucrose. Tissue was post-fixed overnight and then frozen to −70° C. before being sectioned with a sliding microtome. Thirty micron thick sections were mounted on polylysine coated slides and then treated with proteinase K (10 mg/ml, 37° C., 30 min), aceticanhydride and dehydrated in 50%, 70%, 95%, and 100% ethanol. [$^{35}$S]-labeled sense or antisense RNA probes were synthesized from a plasmid that contains a 571 bp PstI/EcoRI fragment of cDNA clone PCX49 (FIG. 7A), subcloned between the bacteriophage SP6 and T7 polymerase promoters. Hybridizations were performed in 50% formamide, 0.3M NaCl, 10% dextran sulfate, and 10 mM dithiothreitol with a probe concentration of 4×10⁶ cpm/ml hybridization buffer. Slides were covered with glass coverslips and incubated overnight at 56° C. Sections were then washed for 15 min in 4× SSC at room temperature, digested with RNAse A (20 mg/ml, 30 min, 37° C.), washed for 30 min in 2× SSC and 1 mM dithiothreitol at room temperature and, finally, for 30 min in 0.1× SSC and 1 mM dithiothreitol at 55° C. Slides were dehydrated (in the presence of 1 mM dithiothreitol) in 50%, 70%, 95%, and 100% ethanol and exposed to Kodak XAR film at room temperature for 2–4 days.

Northern Analysis

Poly(A)+ RNA was denatured at 60° C. in formaldehyde and electrophoresed in 2.2M formaldehyde/1.0% agarose gels. RNA was transferred to a Gene Screen Plus membrane and prehybridized in 50% formamide, 10% dextran sulfate, 1M NaCl, and 1.0% SDS at 42° C. for at least three hours. A [$^{32}$p]-nick-translated 571 bp PstI/EcoRI PCX49 fragment (FIG. 7A) of specific activity 4×10⁸cpm/mg was hybridized to membrane bound RNA for 12–16 h at 42° C. Membranes were washed once at room temperature for 30 min in 2× SSC and 1.0% SDS followed by a 60 min wash in 0.2× SSC and 1.0% SDS at 65° C. Membranes were exposed to Kodak XAR film with an intensifying screen at −70° C.

Oocyte Preparation and RNA Injections

Mature Xenopus laevis (Xenopus I, Madison, Wis.) were used as the source of oocytes. Oocytes were treated with 1 mg/ml type II collagenase (Sigma Chemical Co., St. Louis, Mo.) for two hours at room temperature. The ovarian epithelium and follicle cells were then removed by manual dissection. Each oocyte was injected with 0.5 to 5 ng of RNA transcribed and capped with diguanosine triphosphate in vitro, in a 50 nl volume of water. Injected oocytes were incubated in Barth's saline at 20° C. prior to electrophysiological recordings.

Electrophysiological Recordings

Recordings were obtained from oocytes placed in a groove at the base of a narrow perspex chamber of 0.5 ml volume. Oocytes were perfused at up to 40 ml/min. with a control solution that consisted of 10 mM HEPES (pH 7.2), 115 mM NaCl, 1.8 mM CaCl$_2$, 2.5 mM KCl, and 1 mM atropine. Then oocytes were perfused with agonists or antagonists (added to the control perfusing solution), followed by a wash with control solution. Voltage recordings were made with the bridge circuit of the Dagan 8500 voltage clamp unit on oocytes injected 2–7 days previously. The recordings were obtained at room temperature (20–25° C.) with micropipettes filled with 3M KCl. A resting potential more negative than −30 mV was required for inclusion of a particular oocyte in these studies.

FIGURE LEGENDS

Experimental Section II

FIG. 7A and 7B to 7D. (A) Relationship and lengths of the beta2 cDNAs. Clones were isolated from the brain [light hatched bars] or PC12 [darkhatched bar] cDNA libraries. The black bar represents the coding region and the thin horizontal line represents the 5' and 3' untranslated regions. The PstI site marks the 5' end of a 571 bp PstI/EcoRI fragment of PCX49 used as a probe for northern analysis and to construct the SP6/T7 bacteriophage RNA polymerase promoter containing plasmid. This plasmid was used to prepare radiolabeled RNA probes for in situ hybridization. 7B to 7D Nucleotide sequence of the beta2 cDNAs and the deduced amino acid sequence. Nucleotides are numbered above the sequence and amino acids are numbered under the left most residues.

FIG. 8. Amino acid alignment of the beta2 subunit with the mouse muscle and rat neuronal alpha subunits. Aligned with the beta2 subunit are the mouse muscle alpha1 (Boulter, et al., 1985) and neuronal alpha3 (Boulter, et al., 1986) and alpha4 (clone 4.1) (Goldman, et al., 1987) subunits. Dark background highlights sequence identity among, at least, each of the neuronal alpha subunits and the beta2 subunit. Double daggers mark potential N-linked glycosylation sites, asterisks mark cysteine residues conserved in each member of the neurotransmitter-gated ion-channel subunit superfamily, arrows mark conserved residues in the putative agonist-binding domain of the alpha subunits that are different in the beta2 subunit. Putative transmembrane domains, (TMD I–IV), predicted using the algorithm of Kyte and Doolittle (1982), and a cytoplasmic domain are identified below the aligned sequences.

FIG. 9 (A & B). Northern blot analysis. (A) Poly(A)+ RNA isolated from PC12 cells (8 mg) and (B) Poly(A)+ RNA isolated from an area of the thalamus that includes the medial habenular nucleus (3 mg, lane 1) and from the spinal cord (4 mg, lane 2) was size fractionated on a 2.2 M formaldehyde/1.0% agarose gel and transferred to a Gene Screen Plus membrane. The membrane bound RNA was probed with a [$^{32}$P]-nick-translated 571 bp PstI/EcoRI fragment of PCX49 (See FIG. 7A).

FIG. 10 (A & B). In situ hybridization analysis. Rat forebrain and midbrain sections were probed with [$^{35}$S]-radiolabeled antisense (A) or sense (B) beta2 RNA transcribed in vitro using a plasmid into which a 571 bp PstI/EcoRI fragment of PCX49 (see FIG. 7) was subcloned. Abbreviations are: DLG, lateral geniculate nucleus (dorsal part); DG, dentate gyrus; H, Ammon's horn (hippocampus); IPN, interpeduncular nucleus; MG, medial geniculate nucleus; MH, medial habenular nucleus; NC, neocortex; PC, piriform cortex; PVN, paraventricular hypothalamic nucleus; SON, supraoptichypothalamic nucleus; SNC, substantia nigra, pars compacta; SC, superior colliculus; ST, striatum; TH, thalamus; TU, olfactorytubercle; VTA, ventral tegmental area; VMH, ventromedialhypothalamic nucleus.

TABLE 1

Expression of functional neuronal nicotinic acetylcholine receptors

| mRNAs Injected | Positive | Tested |
|---|---|---|
| α3β2 | 46 | 50 |
| α4β2 | 48 | 49 |
| α2β2 | 25 | 25 |

Oocytes were tested for acetylcholine-evoked voltage depolarizations 2–7 days after the indicated mRNA injection. Each oocyte was typically tested with 10μM acetylcholine. Each negative oocyte was additionally tested with a maximum dose of 1 mM acetylcholine. A positive response to 1 mM acetylcholine was considered to be a reproducible depolarization greater than a noise level defined as +1 mV. Oocytes obtained from different animals typically exhibit variability with respect to expression of acetylcholine sensitivity. Therefore, to control for this variability these data were obtained using oocytes isolated from several different animals and several different preparations of mRNA.

TABLE 2

Effect of co-injection of beta2 mRNA with alpha1, gamma, and delta mRNAs on acetyl-choline-evoked voltage depolaraizations

| mRNAs Injected | Experiment 1 | | Experiment 2 | |
|---|---|---|---|---|
| | RP. (mV) | Δ (mV) | RP. (mV) | Δ (mV) |
| α1γδ | 59.4 ± 1.7 | <0.1 ± <0.1 | 66.1 ± 4.3 | ND |
| α1β2γδ | 64.0 ± 4.3 | 9.9 ± 3.9 | 60.8 ± 4.1 | 27.9 ± 8.6 |
| α1β1γδ | 60.4 ± 3.3 | 41.8 ± 5.0 | — | — |

Experiment 1: Oocytes taken from the same animal were injected at the same time with equivalent amounts of the indicated mRNA combinations. Two days later the oocytes were tested for depolarizing responses (Δ) to 1μM acetylcholine from the corresponding resting potentials (R.P.). Values presented are means ±S.E. (n=6). Of the six oocytes injected with α1γδ mRNAs only one gave a detectable response with 1 μM acetylcholine, whereas all oocytes injected with the two other mRNA combinations gave responses.

Experiment 2: An identical procedure was used except oocytes were obtained from a different animal and 10 μM acetylcholine was used to elicit responses. Values presented are means ±S.E. (n=5). The complete set of mouse muscle mRNAs were not tested in this experiment. N.D. indicates that depolarizations were not detected with 10 μM or 1 mM acetylcholine.

TABLE 3

Reproducible formation of nicotinic acetylcholine receptors by the specific substitution of beta1 mRNA with beta2 mRNA

| mRNAs Injected | Positive | Tested |
|---|---|---|
| α1β1γδ | 85 | 86 |
| α1γδ | 6 | 33 |
| α1β2γδ | 35 | 35 |
| β2 | 0 | 21 |
| α1β2 | 0 | 23 |
| α1β1β2 | 0 | 21 |
| β2γδ | 0 | 20 |
| β2β1γδ | 0 | 21 |

Various combinations of mRNA encoding the mouse muscle nicotinic acetylcholine receptor subunits alpha1, beta1, gamma and delta and mRNA encoding the beta2 subunit were injected into oocytes. Oocytes were tested for voltage depolarizations in response to 10 μM acetylcholine 2–7 days after injection. Each trial scored as negative included a test with 1 mM acetylcholine.

EXPERIMENTAL SECTION III

FUNCTIONAL EXPRESSION OF TWO NEURONAL NICOTINIC ACETYLCHOLINE RECEPTORS FROM cDNA CLONES IDENTIFIES A GENE FAMILY

INTRODUCTION

It seems likely that complex brain functions, such as learning and memory, involve changes in the efficiency of synaptic transmission. One way in which synaptic efficiency might be modified is through a change in the availability or properties of neurotransmitter receptors in the post-synaptic membrane. Testing this idea, and understanding mechanisms that might accomplish such a modification, requires means of detecting and quantifying receptors at synapses in the central nervous system. However, the low abundance and great diversity of neurotransmitter receptors in the central nervous system have made their analysis difficult.

Our group therefore first chose to study neurotransmitter receptors at the more accessible neuromuscular junction, and were able to obtain and express cDNA clones encoding the subunits of the muscle type nicotinic acetylcholine receptor. These cDNA clones were subsequently used to identify homologous genes that code for acetylcholine receptor alpha subunits found in the central nervous system. This approach led to the isolation of two new cDNA clones (Boulter, et al., 1986 and Goldman, et al., 1987) which represent gene transcripts found in different regions of the brain and which encode proteins with the general structural features of muscle nicotinic acetylcholine receptor alpha subunits. Our group proposed that these genes, called alpha3 and alpha4, code for the alpha subunits of functional nicotinic acetylcholine receptors expressed in the central and peripheral nervous systems. This hypothesis has been tested and in this experimental section we show that RNA transcribed from either the clone derived from the alpha3 gene or the clone derived from the alpha4 gene, in concert with RNA transcribed from a new beta2 clone, PCX49, will direct the synthesis of functional neuronal nicotinic acetylcholine receptors in Xenopus oocytes.

RESULTS

Two cDNA clones that encode proteins homologous to the alpha subunit of the muscle nicotinic acetylcholine receptor have been isolated and sequenced. These clones represent transcripts from two of what now appears to be a family of genes that encode the ligand-binding subunits of a family of nicotinic acetylcholine receptors. One clone, PCA48, was isolated from a cDNA library prepared from the PC12 cell line and represents a transcript of the alpha3 gene (Boulter, et al., 1986). Another clone, HYA23-1, was isolated from a cDNA library prepared from rat hypothalamus and represents a transcript of the alpha4 gene (Goldman, et al., 1987). In addition, a genomic clone containing an alpha2 gene has been isolated (Wada, et al., 1988). These genes are expressed in the central nervous system and we propose that the encoded proteins comprise the ligand binding subunits of a family of neuronal acetylcholine receptors.

The sequences of the proteins corresponding to genes alpha1 (expressed in muscle), and alpha3 and alpha4 (expressed in neurons) are shown aligned in FIG. 11. The similarities between the protein sequences are evident in the several conserved sequences, including those defining the hydrophobic regions thought to form membrane spanning helixes (Claudio, et al., 1983; Devillers-Thiery, et al., 1983; and Noda, et al., 1983a). The asterisks indicate two contiguous cysteines that are found in each sequence. The equivalent cysteines in the alpha subunit of the receptor from Torpedo electric organ are labeled with affinity labeling reagents (Kao, et al., 1984). These cysteines are found in all muscle type alpha subunits but not muscle type beta, gamma, or delta subunits. Their presence in each of the sequences shown in FIG. 11 suggests that these proteins all contain an acetylcholine binding site. Because of the overall sequence homology and the conserved cysteines, our group has proposed that the alpha3 and alpha4 gene products are the ligand-binding subunits of the neuronal nicotinic acetylcholine receptors and, by analogy with the muscle nicotinic acetylcholine receptor, have called them the alpha subunits.

The idea that these clones encode receptor subunits was tested by injecting Xenopus oocytes with RNA transcribed from them and assaying the oocytes electrophysiologically for the appearance of functional acetylcholine receptors. Since, by analogy with the muscle nicotinic acetylcholine receptor, it was expected that a functional neuronal nicotinic receptor might require more than one type of subunit, a search was made for clones encoding additional receptor subunits. The search (see the Experimental Procedures section of this experimental section) yielded clone PCX49, which was placed in plasmid pSP65 downstream of the SP6 promoter. This construct, along with the constructs PCA48E (3) and HYA23-1E(1) used in this study, are shown in FIG. 12. The protein encoded by clone PCX49 shows about 50% sequence homology with nicotinic acetylcholine receptor alpha subunits. It also has features common to the alpha subunits, such as the four hydrophobic sequences proposed to constitute membrane spanning domains. However, in contrast to the alpha subunits, it lacks the cysteines thought to contribute to the acetylcholine binding site (Deneris, et al., 1987). Because, as described below, the protein encoded by clone PCX49 acts synergistically with the neuronal alpha gene products to form functional nicotinic acetylcholine receptors, and because it constitutes a second class of neuronal receptor subunits, our group has identified it as a beta subunit. By analogy with the alpha subunit nomenclature, the gene encoding this protein is called beta2.

Figure 13A:
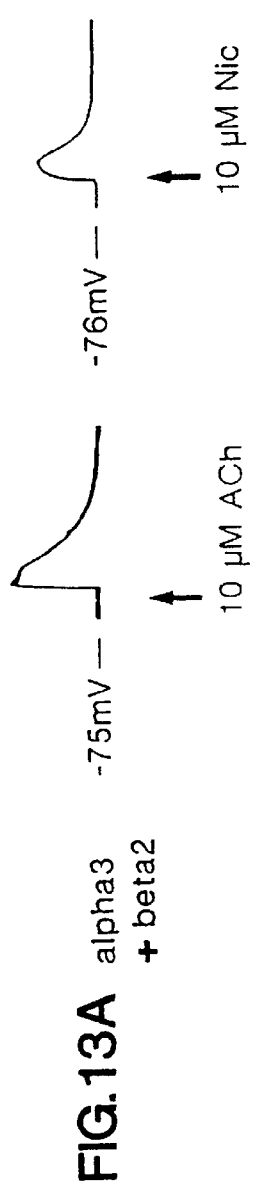
Figure 13B:
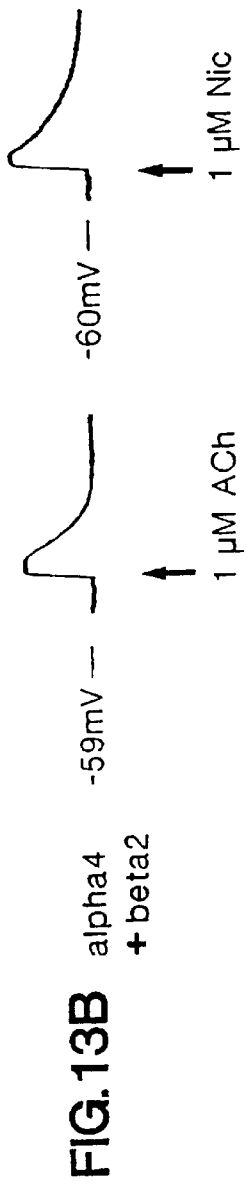
Figure 13C:
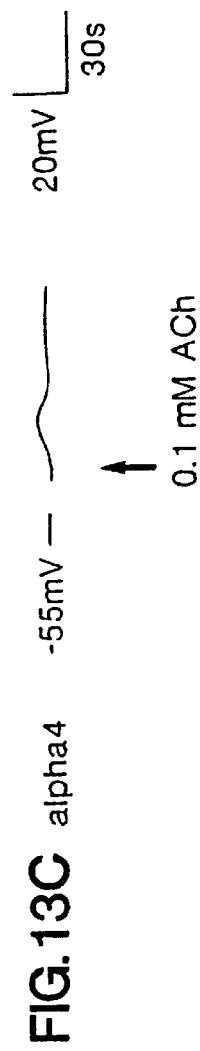

RNA corresponding to the alpha3, alpha4, and beta2 genes was synthesized and injected it into Xenopus oocytes either singularly or in pairwise combinations. Injected oocytes were incubated for two to seven days and those which expressed functional nicotinic acetylcholine receptors were identified by testing for depolarizations in response to perfused acetylcholine. The voltage traces in FIGS. 13A, 13B and 13C (see lines A and B) show that the combination of the beta2 subunit with either the alpha3 or the alpha4 subunits resulted in depolarizing responses to acetylcholine. Since a response to acetylcholine in oocytes injected only with RNA encoding the beta2 subunit was never observed, these results show that both the alpha3 and the alpha4 subunits contribute to the formation of a nicotinic cholinergic acetylcholine receptor. The idea that the beta2 subunit was required for the appearance of a functional receptor was tested by injecting oocytes with only the alpha3 transcript. A response to acetylcholine in these oocytes was never detected. In contrast, cholinergic responses in oocytes injected with RNA corresponding to the alpha4 gene was found. However, as seen in FIGS. 13A, 13B, and 13C, line C, these responses are weak, even in the presence of high concentrations of acetylcholine. The results of these experiments, which are summarized in Table 4, show that functional acetylcholine receptors can be formed with the beta2 subunit in combination with either the alpha3 or the alpha4 subunits. The alpha4 subunit alone will also form a functional receptor, but neither the alpha3 nor the beta2 subunits alone will do so.

The receptors constituted from these clones are cholinergic since they are activated by acetylcholine. Our group has also demonstrated that they are nicotinic by showing depolarizing responses to nicotine (see FIGS. 13A, 13B and 13C). However, there are nicotinic receptors on both muscle and neurons and these receptors have different pharmacological properties. Our group determined that the receptors formed from these clones are of the neuronal type by testing their sensitivity to toxins. Activation of acetylcholine receptors at the neuromuscular junction is blocked by the neurotoxin α-bungarotoxin, while acetylcholine receptors on PC12 cells (Patrick and Stallcup, 1977), rat cervical ganglia (Brown and Fumagalli, 1977), and chick sympathetic ganglia (Carbonetto, et al., 1978) are resistant to this toxin. The neuronal nicotinic acetylcholine receptors on PC12 and ciliary ganglia are, however, blocked by toxin 3.1 (Ravdin and Berg, 1979), which is a minor component in the venom of *Bulgarus multicinctus*.

The sensitivity of the nicotinic acetylcholine receptors comprised of the beta2 subunit and either the alpha3 or the alpha4 subunits was tested for their sensitivity to these toxins. The voltage traces in FIG. 14(A–D) and the data summarized in Table 5 show that receptors formed with beta2 and either the alpha3 (lines A and B) or the alpha4 (lines C and D) subunits are resistant to α-bungarotoxin but are blocked by toxin 3.1. This is in contrast to the nicotinic receptor derived from clones encoding the mouse muscle receptor subunits which is blocked by alpha-bungarotoxin under these conditions (data not shown). These results are consistent with the observation that the nicotinic receptor on the PC12 cell line, the source of clones PCX49 (beta2) and PCA48 (alpha3), is resistant to α-bungarotoxin and sensitive to toxin 3.1. The results also show that these neuronal nicotinic acetylcholine receptors, which are expressed in the brain, are resistant to α-bungarotoxin.

DISCUSSION

In previous papers (Boulter, et al., 1986 and Goldman, et al., 1987), and in Experimental Section I, our group reported the nucleotide and deduced amino acid sequence of two cDNA clones that we proposed were derived from two members of a family of genes encoding the alpha subunits of neuronal nicotinic acetylcholine receptors. This proposal was based on two observations. First, the proteins encoded by these clones show considerable homology with the alpha subunits of muscle nicotinic acetylcholine receptors, including the cysteines (residues 192 and 193) shown to be close to the acetylcholine binding site. Second, the genes encoding these proteins are transcribed in parts of the brain known to have nicotine binding sites (Clarke, et al., 1985). For example, the medial habenula contains transcripts for both the alpha3 and the alpha4 genes and is known to have neurons with nicotinic acetylcholine receptors (McCormick and Prince, 1987). In this experimental section, our group shows that these clones, which each encode alpha subunits will, in combination with the beta subunit encoded by clone, PCX49, form functional nicotinic acetylcholine receptors. Furthermore, it is shown that the receptors thus constituted have pharmacological characteristics of ganglionic nicotinic acetylcholine receptors; they are resistant to a-bungarotoxin and sensitive to toxin 3.1.

Other laboratories have begun biochemical studies on neuronal nicotinic acetylcholine receptors. Hanke and Breer (1986) find that the locust neuronal acetylcholine receptor can be reconstituted from a purified protein preparation that forms a single band on SDS polyacrylamide gel electrophoresis. A clone encoding a protein with sequence homology to the rat alpha3 subunit but lacking the cysteines characteristic of the alpha subunits, and therefore similar to the beta2 subunit, has been isolated from a Drosophilia cDNA library (Hermans-Borgmeyer, et al., 1986). Whiting and Lindstrom (1987b) identified bands on NaDodSoP-4P-/polyacrylamide gels following precipitation of brain extracts using anti-nicotinic acetylcholine receptor antibodies, and showed that some of these bands are labeled with the receptor affinity labeling reagent MBTA (Whiting and Lindstrom, 1987). These bands may correspond to the proteins encoded by the clones we have used in these expression studies. A chicken gene homologous to the rat alpha3 gene has been isolated and sequenced by Ballivet and his co-workers (Nef, et al., 1986). In addition, they found a clone fragment encoding a protein that appears to be the product of an alpha2 gene (Nef, et al., 1986).

Our present results show that the neuronal nicotinic acetylcholine receptors differ from muscle nicotinic receptors in that they can be constituted from only two different gene products. In all experiments reported to date, nicotinic acetylcholine receptors have been formed with $\alpha\beta\lambda\delta$ subunits, $\alpha\beta\lambda$ subunits, $\alpha\beta\delta$ subunits, or $\alpha\lambda\delta$ subunits, but not with any pairwise combinations (Kurosaki, et al., 1987). In contrast, both the alpha3 and alpha4 neuronal receptors can be constituted with only two different types of polypeptide chains, one derived from the specific alpha gene and one derived from a beta gene.

A functional acetylcholine receptor was not detected when only the alpha3 transcript was injected. However, addition of beta2 transcripts to alpha3 transcripts results in the appearance of a functional neuronal nicotinic acetylcholine receptor. Although other explanations are conceivable, the simplest interpretation seems to be that the beta2 subunit joins the alpha3 subunit in the formation of a heterooligomer. The experiments described here do not directly address the issue of the number of subunits that might comprise this heterooligomer. However, the single channel conductances of the muscle and neuronal (Rang, 1981; and Fenwick, et al., 1982) acetylcholine receptors suggests that the channels are similar, and the homologous hydrophobic domains suggest that both receptors are formed by a similar arrangement of membrane spanning regions. It is proposed therefore, by analogy to the nicotinic acetylcholine receptor of the Torpedo electric organ, that the functional neuronal receptor is a pentamer, presumably with two alpha chains.

Although the alpha4 subunit is capable of forming an acetylcholine receptor with no added subunits, it produces a more robust response in combination with the beta2 subunit. It is noted that only one of the possible alpha4 subunits has been tested. At least two different transcripts of the alpha4 gene are made (Goldman, et al., 1987), presumably by alternative splicing, and to date only the alpha4 product encoded by clone HYA23-1E (1) has been tested. The different alpha4 subunits may be functionally distinct and interact with as yet undiscovered subunits. Again, however, it is proposed that the alpha4 receptor constituted in the oocyte is a either a homooligomer composed of five alpha4 subunits or a pentameric heterooligomer composed of alpha4 and beta2 subunits.

The alpha3 and alpha4 genes are transcribed in different parts of the central nervous system, yet both the alpha3 and alpha4 subunits interact functionally with the beta2 subunit in our assay. Since the clone encoding the beta2 subunit, PCX49, and the clone encoding the alpha3 subunit, PCA48, are both derived from PC12 RNA, the cell must make these two transcripts. Therefore, there is clear opportunity for these proteins to assemble into a nicotinic receptor in vivo in this cell line. It is not known if the beta2 gene is transcribed in a cell that also contains alpha4 transcripts. However, since our group has shown that both the alpha3 and alpha4 receptors can be constituted with the beta2 subunit to form a functional neuronal nicotinic acetylcholine receptor, it is possible that different regions in the brain synthesize receptors with different alpha subunits and share the beta2 subunit. Since the alpha3 and the alpha4 subunits differ in their cytoplasmic domains, they may contribute, in different parts of the brain, different regulatory capacities to receptors containing the beta2 subunit. Alternatively, additional as yet unidentified subunits may exist.

SUMMARY

A family of genes coding for proteins homologous to the muscle nicotinic acetylcholine receptor alpha subunit has been identified in the rat genome. These genes are transcribed in the central and peripheral nervous systems in areas known to contain functional nicotinic receptors. In this experimental section, we have demonstrated that at least three of these genes, alpha3, alpha4 and beta2, encode proteins which will form functional nicotinic acetylcholine receptors when expressed in Xenopus oocytes. oocytes expressing either alpha3 or alpha4 protein in combination with the beta2 protein produced a strong response to acetylcholine. Oocytes expressing only the alpha4 protein gave a weak response to acetylcholine. These receptors are activated by acetylcholine and nicotine and are blocked by toxin 3.1. They are not blocked by α-bungarotoxin which blocks the muscle nicotinic acetylcholine receptor. Thus, the receptors formed by the alpha3, alpha4, and beta2 subunits are pharmacologically similar to the ganglionic type neuronal nicotinic acetylcholine receptor. These results demonstrate that the alpha3, alpha4 and beta2 genes code for functional nicotinic acetylcholine receptor subunits which are expressed in the brain and peripheral nervous systems.

EXPERIMENTAL PROCEDURES

Isolation of Clone B1 PCX49

Poly(A)+ RNA was isolated from adult rat hypothalamus and used as template for the synthesis of double stranded cDNA (dscDNA) using the method of Gubler and Hoffman (1983). The dscDNA was ligated into the EcoRI site of λgt10. Approximately $5 \times 10^5$ plaques were screened at low stringency using a radiolabeled probe prepared from clone λPCA48 (encoding the rat alpha3 gene product). One hybridizing clone, λHYA5-1, contained an insert of approximately 1300 base pairs which showed nucleotide and deduced amino acid homology with clone λPCA48; however, alignment of the deduced amino acid sequence with the λPCA48 encoded protein suggested that clone λHYA5-1 was not full-length. The cDNA insert from λHYA5-l was isolated, radiolabeled and used for high stringency screening of $1 \times 10^6$ plaques of a λgtlO cDNA library prepared using polyA+ RNA obtained from the rat pheochromocytoma cell line PC12 (Green and Tischler, 1976). Approximately 50 strongly hybridizing plaques were obtained. One clone, λPCX49, containing a cDNA insert of approximately 2200 base pairs, was shown to be identical to clone λHYA5-1 while extending its nucleotide sequence in both the 5'- and 3'-direction (Deneris, et al., 1987). The cDNA insert from clone λPCX49 was ligated into the EcoRI site of the plasmid vector pSP65 immediately downstream of the bacteriophage SP6 promoter. This construct is shown in FIG. 12.

Construction of Expressible Clone PCA48E(3)

Clone λPCA48, as described (Boulter, et al., 1986), has an inverted repeat sequence located at its 5'-end that contains ATG sequences coding for methionine residues which are not in the same reading frame as the mature protein. Since these sequences might generate inappropriate translation start sites, we cut the λPCA48 cDNA insert at the 5'-SstI site (nucleotide 147), removed the 4 base overhang with mung bean nuclease, digested the DNA with EcoRI and purified the resulting blunt-ended EcoRI fragment on a low melting point agarose gel. This fragment, containing 76 nucleotides of 5'-untranslated sequence, a complete signal peptide and the entire mature protein, was subcloned between the SmaI and EcoRI sites of the plasmid vector pSP64. The construct, PCA48E(3), is shown in FIG. 12.

Construction of Expressible Clone HYA23-1E(1)

Clone λHYA23-1 (corresponding to the alpha4.1 gene transcript) lacks a translation initiator methionine codon at the 5'-end of the protein coding region (Goldman, et al., 1987). To render it suitable for expression studies, two complementary oligonucleotides (5'-AATTGGCCATGGTGA -3' and 5'-AGCTTCACCATGGCC -3') were synthesized which, when annealed, form a linker with an EcoRI compatible end, a HindIII compatible end as well as an internal ATG codon. Sequences flanking the ATG codon conform to the eukaryotic translation initiation consensus sequence (Kozak, 1981). The annealed oligonucleotides were ligated to the full-length EcoRI fragment obtained from clone λHYA23-1, digested with HindIII and subcloned into the HindIII site of the plasmid vector pSP64. The construct, HYA23-1E(1), is shown in FIG. 12.

In Vitro Synthesis of RNA for Oocyte Injections

Plasmid DNA for each construct illustrated in FIG. 11 was linearized with restriction enzymes which cleave at the 3'-end of each clone. These DNAs were used as template for the in vitro synthesis of diguanosine triphosphate capped RNA transcripts using bacteriophage SP6 RNA polymerase (Melton, et al., 1984).

Xenopus laevis Oocyte Injections

Oocytes were removed from anesthetized, mature female Xenopus laevis (Xenopus I, Madison, Wis.) and treated with 1 mg per ml collagenase type II (Sigma Chemical Co., St Louis, Mo.) for two hours at room temperature. The oocytes were dissected free of ovarian epithelium and follicle cells, injected with in vitro synthesized RNAs (0.5 to 5 ng per oocyte) in a total volume of 50 nl of $H_2O$, and incubated in Barth's saline (Coleman, 1984) at 20° C. until needed.

Electrophysiology

Individual oocytes were placed in a groove in the base of a narrow perspex chamber (0.5 ml volume) through which solutions can be perfused at up to 40 ml/min. Drugs were applied by adding them to the perfusing solution and subsequently washing them out with control solution. Control solution contained 115 mM NaCl, 1.8 mM CaCl$_2$, 2.5 mM KCl, 10 mM HEPES (pH 7.2) and 1 M atropine. Voltage recordings were made using the bridge circuit of the Dagan 8500 voltage clamp unit. For these experiments, micropipettes were filled with 3M KCl. Electrophysiological recordings were made at room temperature (20°–25° C.) 2–7 days after injection of the oocytes. Bovine serum albumin (0.1 mg/ml) was added to test solutions to prevent nonspecific binding of toxins. Oocytes with resting potentials of less than −30 mV were rejected from these studies.

FIGURE LEGENDS

Experimental Section III

FIG. 11. Comparison of amino acid sequences of the mouse muscle (alpha1) and two neuronal (alpha3 and alpha4) nicotinic acetylcholine receptor alpha subunits. The two asterisks indicate the cysteine residues at positions 192 and 193 that are thought to be close to the acetylcholine binding site. The molecular weights of the unglycosylated mature alpha1, alpha3, and alpha4 subunits are 55,085, 54,723, and 67,124.

FIG. 12. Restriction maps of the expressible cDNA clones encoding neuronal alpha subunits derived from the alpha3 gene (PCA48E3) and the alpha4 gene (HYA23-1(E)1) and the clone PCX49 derived from the beta2 gene. These clones were constructed as described in the Experimental Procedures section of this experimental section. SP6 refers to the SP6 promoter and the hatched areas indicate the pSP64 multiple cloning site.

FIG. 13 (A, B & C). This figure shows voltage traces obtained from 5 different Xenopus oocytes injected with RNA derived from the neuronal alpha and beta genes. The RNA combinations injected are shown on the left and representative responses to applied acetylcholine and nicotine are shown on the right. RNA and oocytes were prepared and injected as described in the Experimental Procedures section of this experimental section; recordings were made two to seven days after oocyte injection.

FIG. 14 (A, B, C & D). This figure shows the effect of two different neurotoxins on the activation by acetylcholine of two neuronal nicotinic acetylcholine receptor subtypes. The voltage tracing on the left shows the response before application of the toxin and the voltage tracing on the right shows the response following a brief washing and a 30 minute incubation in the indicated concentrations of the two toxins.

TABLE 4

Requirements for functional expression

| RNA injected | No. of oocytes tested | No. of oocytes positive |
| --- | --- | --- |
| alpha3 | 30 | 0 |
| alpha4 | 30 | 10 |
| beta2 | 21 | 0 |
| alpha3 + beta2 | 50 | 46 |
| alpha4 + beta2 | 49 | 48 |
| No injection | 21 | 0 |
| Sham injection | 21 | 0 |

Two to seven days after injection with RNA, oocytes were tested for responses to acetylcholine. Each test included a maximal concentration of 1 mM acetylcholine. Detection of a reproducible depolarization greater than a noise level of +1 mV was considered to be a positive response. These data represent the results of experiments conducted over a period of 4 months with more than six different lots of RNA for the injections.

TABLE 5

Effect of neurotoxins

| RNA Injected | n | AcCho, μM | Toxin | Before toxin RP, mV | Before toxin Δ, mV | After toxin RP, mV | After toxin Δ, mV |
| --- | --- | --- | --- | --- | --- | --- | --- |
| α3 + β2 | 4 | 10 | α-Bgt | 66.8 ± 4.1 | 25.4 ± 3.3 | 71.9 ± 4.1 | 24.8 ± 3.3 |
|  | 3 | 5 | α-Bgt 3.1 | 76.3 ± 2.3 | 24.0 ± 1.7 | 77.3 ± 1.7 | 4.1 ± 0.4 |
| α4 + β2 | 4 | 10 | α-Bgt | 70.1 ± 2.6 | 35.4 ± 4.7 | 72.4 ± 3.5 | 32.7 ± 6.4 |
|  | 3 | 5 | α-Bgt 3.1 | 69.3 ± 3.8 | 21.7 ± 3.5 | 75.6 ± 2.4 | 0.8 ± 0.3 |

Oocytes were injected with RNA and tested for depolarizing responses. The depolarizations (Δ) from the corresponding resting potential (RP) produced by the perfusion of acetylcholine (AcCho) were measured before and after a 30-min. incubation with either 0.1 μM α-bungarotoxin (α-Bgt) or 0.1 μM toxin 3.1 (α-Bgt 3.1). Values presented are the averages (±SEM) of experiments with n oocytes.

EXPERIMENTAL SECTION IV

ISOLATION AND FUNCTIONAL EXPRESSION OF A GENE AND cDNA ENCODING THE ALPHA2 SUBUNIT OF A RAT NEURONAL NICOTINIC ACETYLCHOLINE RECEPTOR

INTRODUCTION

A new type of agonist-binding subunit of rat neuronal nicotinic acetylcholine receptors (nAChRs) has been identified and characterized. Rat genomic DNA and cDNA encoding this subunit (alpha2) were cloned and analyzed. cDNA expression studies in Xenopus oocytes revealed that the injection of alpha2 and beta2 (a neuronal nAChR subunit) mRNAs lead to the generation of a functional nAChR. In contrast to the other known neuronal nAChRs, the receptor produced by the injection of alpha2 and beta2 mRNAs was resistant to an alpha-neurotoxin, Bgt3.1. In situ hybridization histochemistry showed that alpha2 mRNA was expressed in a small number of regions, in contrast to the wide distribution of the other known agonist-binding subunits (alpha3 and alpha4) mRNAs. These results demonstrate that the alpha2 subunit differs from other known agonist-binding alpha-subunits of nAchRs in its distribution in the brain and in its pharmacology.

RESULTS AND DISCUSSION

Recent studies have demonstrated that there is a family of genes encoding functional subunits of rat neuronal nicotinic acetylcholine receptors (nAChRs) (Boulter, et al., 1986; Goldman, et al., 1987; Boulter, et al., 1987; Deneris, et al., 1988). The first three genes to be identified have been designated alpha3, alpha4 and beta2. The alpha3 and alpha4 genes have been proposed to encode agonist-binding subunits (Boulter, et al., 1986; Goldman, et al., 1987; Boulter, et al., 1987) which, in combination with the beta2 gene product, will form a functional neuronal nAChR in Xenopus oocytes (Boulter, el al., 1987). In addition, our previous study (Nef, et al., 1986) a genomic fragment was isolated that suggested the existence of another gene, alpha2. Our group has now isolated rat genomic and cDNA clones encoding the entire alpha2 gene product. The deduced amino acid sequence is homologous to the alpha3 and alpha4 proteins. CDNA expression studies in Xenopus oocytes reveal that the injection of alpha2 and beta 2 mRNAs leads to the generation of a functional neuronal nAChR. In contrast to neuronal nAChRs produced by the injection of beta2 and either alpha3 or alpha4 mRNAs (Boulter, et al., 1987), the receptor formed from the expression of alpha2 and beta2 proteins is resistant to the alpha-neurotoxin, Bgt3.1 (Ravdin, et al., 1979). In situ hybridization histochemistry shows that the overall pattern of the expression of alpha2 transcripts is different from that of alpha3 and alpha4 transcripts. These results demonstrate that the alpha2 gene codes for a functional neuronal nAChR alpha-subunit (putative agonist-binding subunit) with features distinct from other proposed agonist-binding subunits.

Rat genomic DNA and brain cDNA libraries were screened according to the strategy described in the legend of FIGS. 15A, 15B and 15C to 15F. Among several isolated clones, two genomic clones (R12 and R31, see FIG. 15A) and four cDNA clones (HYP16, C22, C183 and C244, see FIG. 15B) were studied further. Sequence analysis of these clones has revealed that the protein-coding sequence of the rat alpha2 gene is composed of 6 exons extending over 9 kb of genomic DNA (FIGS. 15A and 15C to 15F. The assigned exon-intron boundaries are compatible with the GT/AG rule (Breathnach, et al., 1978). The primary structure of the alpha2 protein was determined using an oen reading frame corresponding to the known sequences of muscle and neuronal nAChR subunits (Boulter, et al., 1986; Goldman, et al., 1987; Boulter, et al., 1985). See FIGS. 15C to 15F. The sequence around the predicted initiator methionine codon (ATG) agrees with the consensus sequence described by Kozak (1984).

The alignment of the sequence of each cDNA clone with the genomic DNA indicates that, among the four cDNA clones, only the HYP16 clone contains an open reading frame for the entire alpha2 protein. Clones C183 and C244 lack exons 2 and 3 and a 5' part of exon 5 is deleted in C244. The deletions of exon 2 and 3 shift the reading-frame and would result in the termination of translation before the appropriate C-terminal residue. It is likely that the deletions in the two clones represent splicing errors. A similar case was reported elsewhere (Bell, et al., 1986). However, a recent study (Breitbart, et al.. 1987) has raised the possibility that alternative splicing resulting in the failure of the synthesis of a protein may be a mechanism for the regulation of gene expression. Clones C183 and C244 may be examples of this phenomenon. Restriction enzyme mapping, S1 nuclease protection mapping and partial sequencing (data not shown) indicated that regions of these clones 3' to the deleted exons are identical to the homologous region of the full length clone HYP16.

The deduced amino acid sequence shows that the alpha2 protein is composed of 511 amino acids. The amino terminus of the mature protein was predicted by the method of von Heijne (1986). The proposed mature alpha2 protein is preceded by a leader sequence of 27 residues and is composed of 484 amino acid residues with a calculated molecular weight of 55,480 daltons.

Several common structural features found in all known nAChR subunits (Boulter, et al., 1986; Goldman, et al., 1987; for a review, see Stroud and Finer-Moore, 1985, and Heinemann, et al., 1986; also see Takai, et al., 1985 and Hermans-Borgmeyer, et al., 1986) are conserved in alpha2. Some of these features are also found in glycine and GABA receptor subunits (Grenningloh, et al., 1987; Schofield, et al., 1987), and are presumed to be important for the function of ligand-gated ion channels. These conserved features are: first, cysteine residues aligned at residues 133 and 147 (alpha2 protein numbering, analogous to the cysteine residues at 128 and 142 in Torpedo receptor subunits); second, four hydrophobic putative membrane-spanning segments (M1–M4); third, a proline residue in the M1 segment, which has been proposed to introduce structural flexibility for the control of the channel lumen (Brandl and Dweber, 1986); and fourth, an abundance of uncharged polar amino acid residues in the M2 segment which may form a hydrophilic inner wall for ion-transport (Hucho, et al., 1986; Giraudat, et al., 1987; Imoto, et al., 1986).

The alpha2 protein has a higher amino acid sequence identity with the alpha3 and alpha4 proteins (57% and 67%, respectively, see FIG. 16) than with beta2 (48%) or alpha1 (49%) proteins. Two contiguous cysteine residues align at 197 and 198 in the alpha2 protein. The equivalent residues are found in Torpedo (Stroud and Finer-Moore, 1985) and muscle (Heinemann, et al., 1986) nAChR agonist-binding alpha subunits and in the proposed agonist-binding subunits of neuronal nAChR receptors (Boulter, et. al., 1986; Goldman, et al., 1987; Nef, et al., 1986) including a Drosophilia receptor subunit (Ballivet, et al., In Preparation). These residues have been shown to be close to the acetylcholine (ACh) binding site in Torpedo nAChRs (Kao, et al., 1984). In addition, the alpha2 protein has three potential N-linked glycosylation sites at residues 29, 79 and 185. The first site is conserved in all known neuronal subunits (Boulter, et al., 1986; Goldman, et al., 1987; Deneris, et al., 1988; Hermans-Borgmeyer, et al., 1986; and Ballivet, et al., In Preparation). This site is not found in muscle or electric organ nAChR subunits. All known subunits of nAChRs, except for the subunits of Drosophilia receptor, have a potential glycosylation site at Asn146 (alpha2 protein numbering). However, the equivalent residue of the alpha2 protein is probably not glycosylated because the residue does not lie in a glycosylation consensus sequence (Marshall, 1974).

The sequence similarity and the existence of common structural features suggest that the alpha2 gene is a member of the neuronal nAChR gene family. The presence of the two contiguous cysteine residues at 197 and 198 further suggest that the alpha2 protein is an agonist-binding subunit. These inferences are supported by cDNA expression studies in Xenopus oocytes. mRNA transcribed from HYP16 cDNA clone (see FIG. 15B) was injected into oocytes in combination with beta2 MRNA derived from the cDNA clone, PCX49 (Boulter, et al., 1987; Deneris, et al., 1988). mRNA transcribed from HYP16 cDNA clone (see FIG. 15B) was injected into oocytes in combination with the cDNA clone, PCX49. The PCX49 clone is derived from the beta2 gene and is believed to encode a non-agonist-binding subunit. (Boulter, et al., 1987; Deneris, et al., 1988). Depolarizing responses were recorded to perfused ACh (1–10 µM) in all oocytes injected with a mixture of alpha2 and beta2 mRNAs (n=25). The responses could be blocked by d-tubocurarine and hexamethonium but not by alpha-bungarotoxin (Table 6). Nicotine (10 µM) also elicited a depolarizing response (data not shown). These are the properties expected of ganglionic nAChRs (Patrick and Stallcup, 1977; Carbonetto, et al., 1978). We tested whether oocytes injected with either alpha2 (n=22) or beta2 (n=21) mRNA alone would produce a depolarizing response to ACh. In experiments which included a maximum application of 1 mM ACh, no responses were found. These results show that neither alpha2 nor beta2 subunit alone will form a functional receptor but that co-injection of the RNAs results in formation of a functional neuronal nAChR.

Interestingly, the α-neurotoxin Bgt3.1 failed to substantially block the receptor produced by the injection of alpha2 and beta2 mRNAs (Table 6). Bgt3.1 has been shown to block the neuronal nAChRs in ganglia (Ravdin and Berg, 1979) and the adrenal medulla (Higgins and Berg, 1987). The receptors formed in oocytes after the injection of beta2 and either alpha3 or alpha4 mRNAs were sensitive to this toxin (Boulter, et al., 1987). This result demonstrates that the alpha2-type receptor is pharmacologically distinct from all other nAChRs characterized to date (Boulter, et al., 1987; Mishina, et al., 1984; Mishina, et al., 1986).

In situ hybridization histochemistry on rat brain sections shows that the pattern of distribution of the alpha2 transcripts is distinct from that of the alpha3 and alpha4 transcripts, although there are some areas of overlap. Only weak signals for alpha2 are detected in the diencephalon, whereas alpha3 and alpha4 transcripts are strongly expressed in the diencephalon, particularly in the thalamus (FIG. 17A; also see Goldman, et al., 1986, and Goldman, et al., 1987). The most intense signal for alpha2 is detected in the interpeduncular nucleus (FIG. 17B). These and previous observations (Boulter, et al., 1986; Goldman, et al., 1986; Goldman, et al., 1987) suggest that the alpha2, alpha3 and alpha4 each code for three different receptor systems.

The studies presented in this section, and in Experimental Sections II, III, V and VI, show that functional neuronal nAChRs are formed in oocytes after the injection of beta2 or beta4 and either alpha2, alpha3 or alpha4 mRNAs. Although this fact does not address the issue of the subunit composition of neuronal nAChRs in vivo, a recent study (Whiting and Lindstrom, 1987a; Whiting and Lindstrom, 1987b) is consistent with and therefore provides support for the idea that two types of subunits are sufficient in vivo. In that study, one of the neuronal nAChRs has been purified from rat brain and suggested to be composed of two subunits. Furthermore, based upon the stoichiometry of Torpedo electric organ receptor, we predict that the neuronal receptor is a pentameric structure.

Detailed studies of in situ hybridization histochemistry (Wada, et al., 1988) show that alpha2, alpha3 and alpha4 transcripts are co-expressed with beta2 transcripts (Deneris, et al., 1988) in many brain regions. This result suggests that the functional combinations observed in oocytes may also occur in vivo. However, the studies also show that in some regions, beta2 and alpha2, alpha3 and alpha4, transcripts are not co-expressed. This observation suggests the existence of other alpha-type and beta-type subunit(s). It would seem, therefore, that there may be more than three distinct populations of neuronal nAChRs.

SUMMARY

Our evidence indicates that the alpha2 gene product functions as a neuronal nAChR subunit with pharmacological features different from the alpha3 and alpha4 subunits and that the alpha2-type receptor is different from any neuronal nAChRs studied to date.

FIGURE LEGENDS

Experimental Section IV

FIGS. 15(A, B & C to F. Restriction enzyme maps of rat genomic DNA (A) and cDNA (B) encoding the alpha2 protein and nucleotide sequences of the genomic DNA with the deduced amino acid sequence (C). In (A), the locations of exons comprising the protein-coding sequence are indicated by numbered boxes. A closed box represents the protein-coding sequence. In (B), the protein-coding sequence is indicated by the closed box. The deleted sequences in clones C183 and C244 are indicated by broken lines. C183 and C244 clones lack exons 2 and 3. A part of exon 5 (nucleotides 300 to about 432) is also deleted in the C244 clone. In 15C to 15F, the 5' nucleotide sequences(−386 to about 393) are derived from the HYP16 cDNA clone. Sequences extending to the 5' and 3' end of the HYP16 cDNA sequence are not shown. Lower-case nucleotide symbols indicate acceptor and donor sites of intron sequences. The nucleotides are numbered starting with the first nucleotide in the codon corresponding to the proposed amino terminus of the mature alpha2 protein. The deduced amino acid sequences are numbered starting with the amino terminus of the mature protein. Nucleotides and amino acids on the 5' side of residue 1 are indicated with negative numbers. The amino terminus of the mature alpha2 protein was predicted by the method of von Heijne (1986).

Figure 15A:
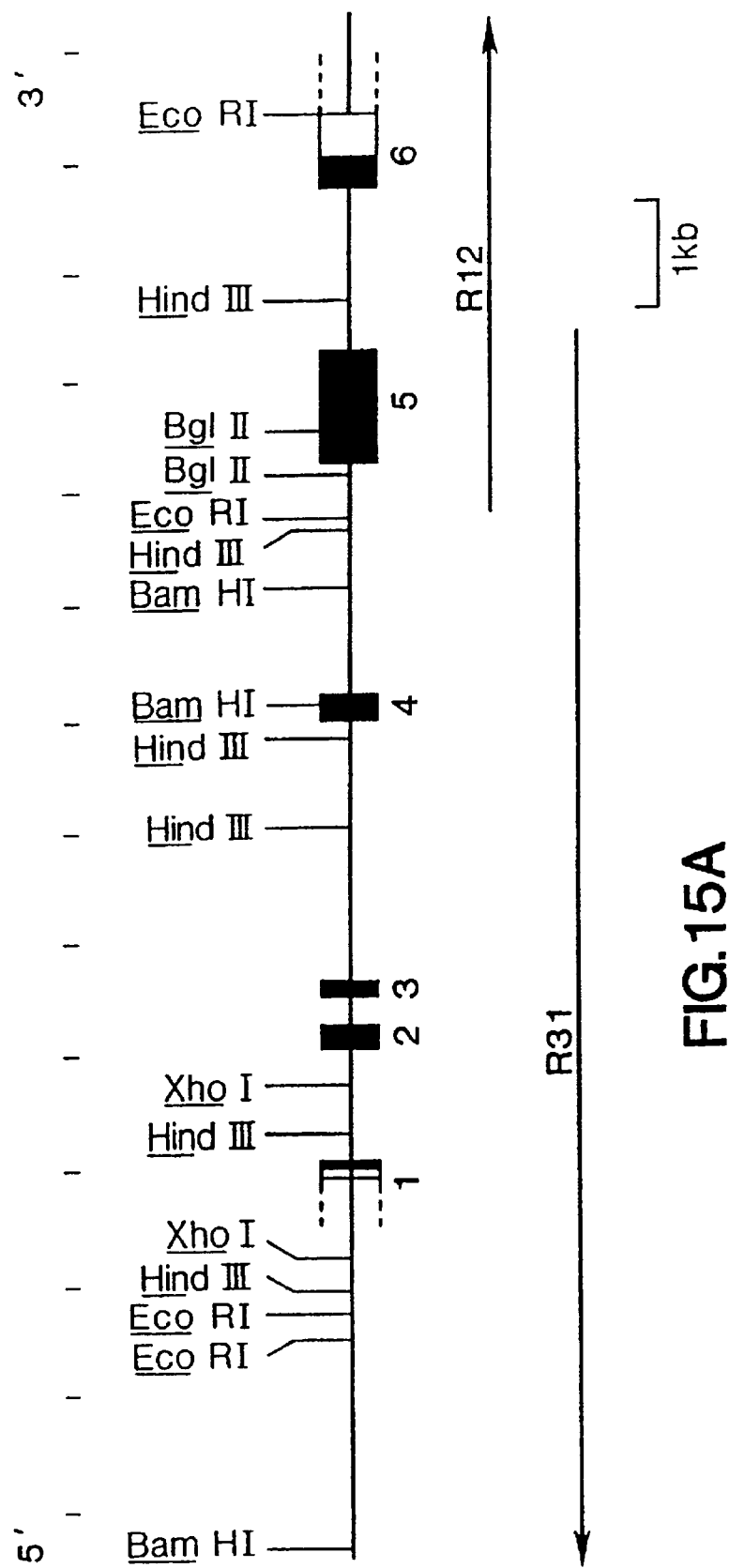
Figure 15B:
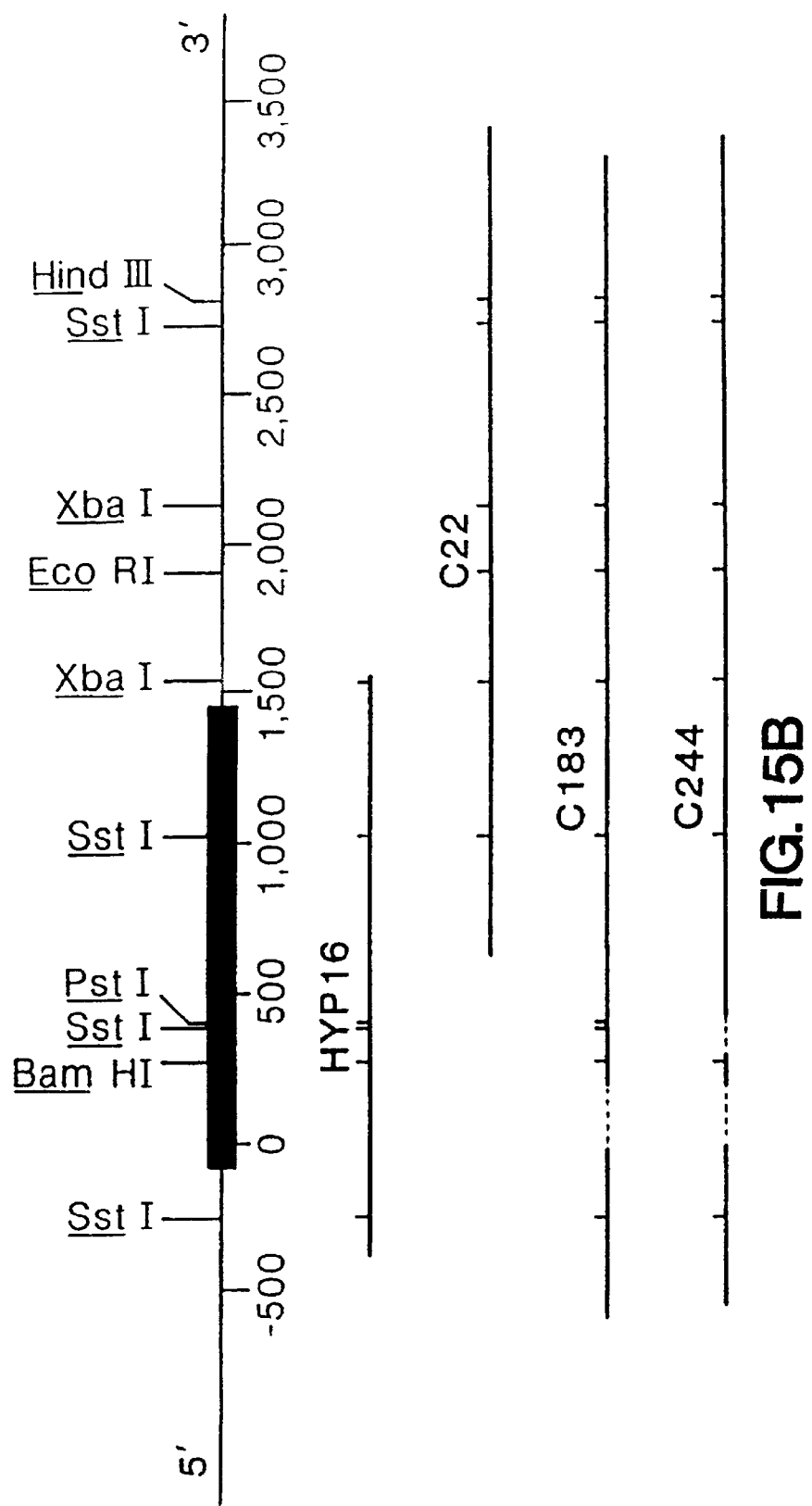

FIGS. 15A, B, C to F Methods. An EMBL3 phage library ($1.5 \times 10^6$ recombinants) of rat genomic DNA (Sierra, et al., 1986) was screened with a fragment of previously cloned avian alpha2 genomic DNA (Nef, et al., 1986; Ballivet, et al., In Preparation). A fragment (approximately 300 bp) encoding a part of 5' extracellular region of avian alpha2 protein was labeled by nick-translation (Rigby, et al., 1977). Hybridization and washing of filters were carried out in 5 x SSPE at 55° C. Ten clones were isolated and two of them (R12 and R31) were analyzed in detail. Fragments of the R12 and R31 inserts were subcloned into pUC 8 vectors and sequenced by the chemical method (Maxam and Gilbert, 1977). Rat brain cDNA libraries were constructed in λgt10 vector (Huynn, et al., 1985) by using poly(A)+ RNA isolated from cerebellum, hypothalamus and hippocampus regions. Precise methods for constructing the libraries were described previously (Boulter, et al., 1986; Goldman, et al.. 1987). Initial clones were isolated by probing with a nick-translated cDNA (approximately 1940 bp) coding for the rat alpha4 protein (Goldman, et al., 1987). The initial cDNA clones were then used to isolate longer cDNA clones. Hybridization and washing of filters were carried out in 5 x SSC or 5 x SSPE at 65° C. From a total of $6 \times 10^6$ phages, six positive clones were isolated. Four of the isolated clones (C22, C183, C244 and HYP16) were analyzed in detail. The cDNAs were subcloned into M13 derivatives (Messing, et al., 1977) and sequenced by the chain termination method (Sanger, et al., 1977).

FIG. 16. Alignment of the amino acid sequences of mouse muscle alpha subunit (alpha1) (Boulter, et.al., 1985) and rat neuronal alpha subunits (alpha2, alpha3 and alpha4) (alpha2 and alpha3: Boulter, et al., 1986; alpha4: Goldman, et al., 1987). Amino acids conserved in all four alpha subunits are shown on a black background. The two cysteine residues that are thought to be close to the acetylcholine binding site (Kao, et al., 1984) are indicated by asterisks. Signal peptide, putative membrane-spanning and cytoplasmic regions and the proposed amphipathic helix (Guy and Hucho, 1987) are indicated below the aligned sequences. The mature alpha2 protein has 49, 57 and 67% amino acid sequence identity with the mature alpha1, alpha3 and alpha4 proteins, respectively. The percentages of sequence identity were calculated by dividing the number of identical residues by the number of residues in the shorter of the two compared sequences.

FIG. 17(A & B). Comparison of the distribution of alpha2, alpha3 and alpha4 transcripts by in situ hybridization histochemistry. Serial coronal sections through the medial habenula (A) and the interpeduncular nucleus (B) were hybridized with the probes for alpha2, alpha3 and alpha4. In (B), slides contain sections of the trigeminal ganglion. Abbreviations: C, cortex; IPN, interpeduncular nucleus; MH, medial habenula; MG, medial geniculate nucleus; T, thalamus.

digested with proteinase K (10 µg/ml, 37° C., 30 minutes), acetylated, and dehydrated. Hybridization with $^{35}$S-radiolabeled RNA probe (5–10×10$^6$ cpm/ml) was performed at 55° C. for 12–18 hrs in a solution containing 50% formamide, 0.3 M NaCl, 10 mM Tris (pH 8.0), 1 mM EDTA, 0.05% tRNA, 10 mM DTT, 1x Denhardt's solution and 10% dextran sulfate. Because of the high sequence similarities in the protein coding regions of the cDNAs, 3' untranslated sequences were used to make probes. The EcoRI/3' end, BalI/3' end and Bg/I/3' end fragments derived from C183 (FIG. 15B), PCA48 (Boulter, et al., 1986) and alpha4.2 (Boulter, et al., 1986) cDNA clones, respectively, were subcloned into the plasmid, pSP65 and used to synthesize antisense RNA probes in vitro (Melton, et al., 1984). After hybridization, sections were treated with RNaseA (20 µg/ml, 37° C., 30 minutes) and washed in 0.1 x SSC at 55° C. Dehydrated slides were exposed to X-ray films for 3–16 days at 4° C. A RNA probe coding the sense strand of C183 clone was used as a control.

TABLE 6

Pharmacological properties of the nAChR formed after the injection of alpha2 and beta2 mRNAs

| Effects of antagonists on agonist responses | | | | | | | |
|---|---|---|---|---|---|---|---|
| | | | | Agonist | | Agonist + Antogonist | |
| Agonist | µM | Antagonist | µM | RP. (mV) | Δ (mV) | RP. (mV) | Δ (mV) | n |
| ACh | 1 | Hex | 100 | −75 ± 7 | +8 ± 1 | −78 ± 7 | +0.4 ± 0.4 | 4 |
| ACh | 5 | dtc | 100 | −75 ± 5 | +19 ± 1 | −76 ± 5 | +2.0 ± 0.4 | 3 |

| Agonist responses before and after toxin incubation | | | | | | | |
|---|---|---|---|---|---|---|---|
| | | | | Before toxin | | After toxin | |
| Agonist | µM | Toxin | µM | RP. (mV) | Δ (mV) | RP. (mV) | Δ (mV) | n |
| ACh | 10 | α-Bgt | 0.1 | −82 ± 7 | +28 ± 2 | −85 ± 7 | +32 ± 2 | 3 |
| ACh | 10 | Bgt 3.1 | 0.1 | −69 ± 1 | +27 ± 2 | −71 ± 3 | +24 ± 1 | 3 |

Preparation of oocytes, RNA injection and electrophysiological recording were performed as described previously (Boulter, et al., in press). Briefly, Xenopus laevis oocytes were injected with alpha2 and beta2 (Boulter, et al., in press and Deneris, et al., in press) RNAs (2–5 ng each per oocyte) in a total volume of 50 nl of H$_2$O. Alpha2 and beta2 RNAs were synthesized in vitro (Melton, et al., 1984) by using the plasmid, pSP65, containing HYP16 and PCX49 (Boulter, et al., in press andDeneris, et al., in press) cDNA's, respectively. After injection, oocytes were incubated at 20° C. in Barth's saline for 2–5 days. The depolarizing responses (Δ) to perfused agonist from the corresponding resting potential (R.P.) were recorded in the presence and absence of antagonists at room temperature (20–25° C.). The control solution contained 115 mM NaCl, 1.8 mM CaCl$_2$, 2.5 mM KCl, 10 mM HEPES (pH 7.2) and 1 µM atropine. For toxin studies, recordings were performedbefore and after a 30 minute incubation with either α-bungarotoxin (α-Bgt) or the α-neurotoxin, Bgt 3.1. Bovine serum albumin (0.1 mg/ml) was added to the toxin test solution to prevent non-specific binding. Only healthy oocytes with resting potentials greater than −30 mV were used for recordings. Values given are mean ± s.e.m. of experiments in (n) oocytes.
Other abbreviations: ACh, acetylcholine; Hex, hexamethonium; dtc, d-tubocurarine.

FIG. 17(A & B) Methods. Tissue preparation and hybridization were performed as previously described (Goldman, et al., 1987; Goldman, et al., 1986; Cox, et al., 1984; Swanson, et al., 1983a), with minor modifications. Briefly, rats were perfused with 4% paraformaldehyde/0.1 M acetate buffer, pH 6, followed by 4% paraformaldehyde/0.05% glutaraldehyde/0.1 M sodium borate buffer, pH 9.5. Brains were post fixed overnight at 4° C. in the second fixative including 10% sucrose but not glutaraldehyde. Brain sections (25 µm) were mounted on poly-L-lysine-coated slides,

EXPERIMENTAL SECTION V

BETA3: A NEW MEMBER OF THE NICOTINIC ACETYLCHOLINE RECEPTOR GENE FAMILY IS EXPRESSED IN THE BRAIN

SUMMARY

Screening of a rat brain cDNA library with a radiolabeled probe made from an alpha3 cDNA (Boulter, et al., 1986) resulted in the isolation of a clone whose sequence encodes a protein, beta3, which is homologous (40–55% amino acid sequence identity) to previously described neuronal nicotinic acetylcholine receptor subunits. The encoded protein has structural features found in other nicotinic acetylcholine receptor (nAchR) subunits. Two cysteine residues that correspond to cysteines 128 and 142 of the Torpedo nAchR alpha subunit are present in beta3. Absent from beta3 are two adjacent cysteine residues that correspond to cysteines 192 and 193 of the Torpedo alpha subunit. In situ hybridization histochemistry, performed using probes derived from beta3 cDNAs, demonstrated that the beta3 gene is expressed in the brain. Thus, beta3 is the fifth member of the nAchR gene family that is expressed in the brain. The pattern of beta3 gene expression partially overlaps with that of the neuronal nAchR subunit genes alpha3, alpha4, or beta2. These results lead our group to propose that the beta3 gene encodes a neuronal nAchR subunit.

Electrophysiological studies indicate that acetylcholine functions as a neurotransmitter in many regions of the mammalian central nervous system (reviewed in Clark, 1988). Acetylcholine activates two structurally distinct classes of cell surface receptors: those activated by the mushroom alkaloid muscarine and those activated by the tobacco alkaloid nicotine. Transduction of the signal elicited by the binding of the acetylcholine to muscarine receptors is mediated by the activation of GTFI-binding (G) proteins, which in turn leads to the modulation of various effector proteins. Nicotinic acetylcholine receptors (nAchRs), in contrast, form cation-channels in the membrane of nerve or muscle in response to the binding of acetylcholine (for review see Popot, 1984).

An investigation concerning the diversity of subtypes, structure, and location of nAchRs in the mammalian brain has been pursued using the techniques of molecular genetics (Boulter, et al., 1986, Goldman, et al., 1987; Deneris, et al., 1988; and Wada, et al., 1988). This approach has resulted in the identification of four genes encoding different subunits, alpha2, alpha3, alpha4, and beta2 of nAchRs. Functional expression studies performed in *Xenopus laevis* oocytes have demonstrated that three different receptors can be formed by combining beta2 subunits, in pairwise combination, with each of the alpha subunits (Boulter, et al., 1987). In situ hybridization analysis has shown that beta2 transcripts co-localize with the alpha subunit transcripts in several regions of the brain. This is consistent with the idea that the beta2 subunit contributes to the formation of some neuronal nAChRs by combining with either the alpha2, alpha3, or alpha4 subunits (Deneris, et al., 1988).

In situ hybridization analysis has also revealed that in some regions of the brain alpha transcripts, but not beta2 transcripts, can be detected. Conversely, in certain regions of the brain, beta2 transcripts can be detected but the alpha subunit transcripts are undetectable. These data suggest that other receptor subunits exist. Because of an interest determining the extent of this gene family, brain cDNA libraries were screened with probes made from the available neuronal nAChR cDNAs. Described in this experimental section is the isolation of a cDNA clone that defines another new member of the nAChR gene family.

EXPERIMENTAL PROCEDURES

Screening of a Rat Brain cDNA Library

The construction of a brain cDNA library in which the cDNA was prepared with RNA obtained from the diencephalon of the rat and cloned into the EcoRI site of λgt10 has been described previously (Goldman, et al., 1987). Recombinants were screened with a [$^{32}$P]-dCTP nick-translated PCA48 cDNA encoding the alpha3 gene product (Boulter, et al., 1986). Filter hybridization was performed overnight in 5xSSPE (1xSSPE is 180 mM NaCl, 9 mM Na2HPO4, 0.9 mM NaH2PO4 and 1 mM EDTA, pH 7.4), 1% SDS, IX Denhardt's solution (IX Denhardt's solution is 0.02% (w/v) each ficoll, polyvinylpyrrolidone, and bovine serum albumin) at 65° C. The next day filters were washed twice at room temperature for 30 min in 2x SSC (1xSSC is 150 mM NaCl and 15 mM sodium citrate, pH 7.0) and once at 65° C. for 1 hr in 0.2x SSC and 1% SDS. Hybridizing phage were then purified.

Nucleotide Sequence Determination and Analysis

The cDNA inserts of purified λgt10 clones were subcloned into the EcoRI site of M13mp18. Nucleotide sequence analyses of some of the cDNA clones described herein revealed an internal EcoRI site at nucleotide position 73 (see Results and Discussion section of this experimental section and FIGS. 19A to 19C). Because the cDNA was ligated into the EcoRI cloning site of λgt10, nucleotide sequencing of some cDNA inserts required the subcloning of two fragments from each primary clone into M13mp18. A nested set of overlapping M13 subclones was generated by the method of Dale, et al., (1985) and each was sequenced by the chain termination method of Sanger, et al., (1977). Deduced amino acid sequences were aligned and the percent sequence identity calculated by dividing the number of identical residues by the number of residues in the shorter of two subunits being compared.

Construction of Expression Clone pESD76

Figure 18A:
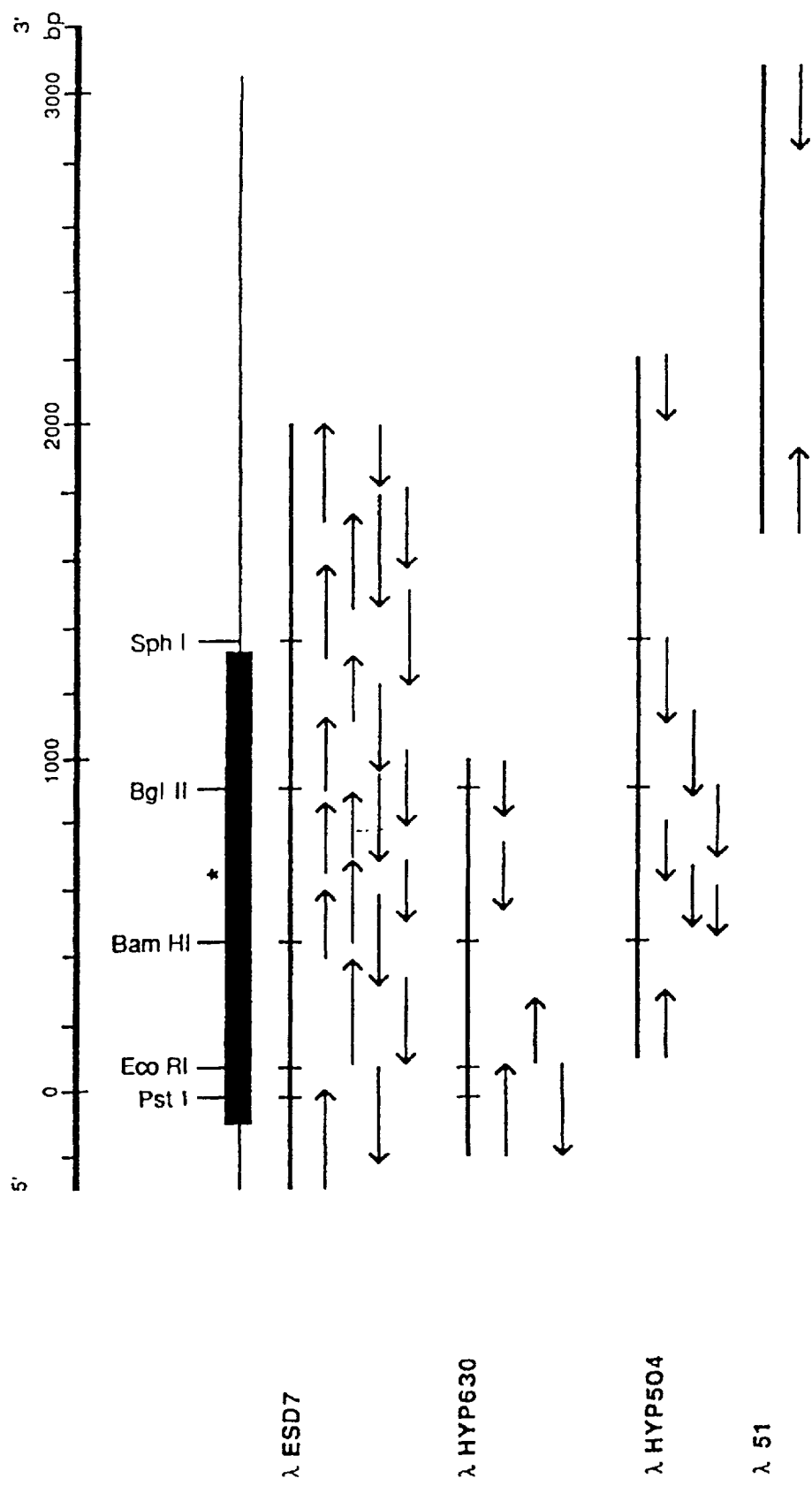
Figure 18B:
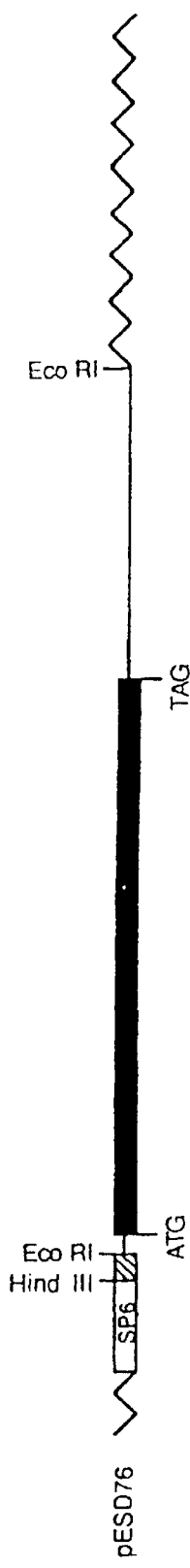

The following procedure was used to obtain a cDNA clone suitable for in vitro expression studies. An EcoRI partial digest was carried out with DNA isolated from clone λESD-7 (see FIG. 18A). The sample was electrophoresed in an 0.8% low melting point agarose gel and the 2100 base pair partial EcoRI fragment containing the presumed protein coding region of λESD-7 was isolated and subcloned into the EcoRI site of plasmid vector pSP65. One such clone, pESD77, had the partial EcoRI fragment oriented with the amino terminus of the encoded protein distal to the SP6 polymerase promoter. Complete nucleotide sequencing data subsequently revealed that the parental clone λESD-7 contained what appeared to be a single base pair deletion at nucleotide position 646 (FIG. 19) which resulted in a truncated reading frame. Therefore, additional cDNA clones were isolated and sequenced (see Results and Discussion section of this experimental section). From approximately 7×10⁶ plaques screened, three clones were isolated (FIG. 18A). The nucleotide sequence through the region that contained the frameshift in λESD-7 was determined for λHYP504 and λHYP630. Both of these clones contained an additional thymidine residue at nucleotide position 646 and maintained an extended open reading frame. However, none of these clones contained the entire coding region present in λESD-7 (see FIG. 18A). To generate a full length clone without the truncated reading frame, clone pESD77 was cleaved with BamHI. The 5' fragment from the BamHI site in the pSP65 multiple cloning site to the nucleotide at position 442 was isolated after electrophoresis in low melting point agarose. This BamHI fragment was ligated to the 3'-BamHI-EcoRI fragment obtained from λHYP504 and subcloned into a BamHI-EcoRI cleaved pSP64 vector. One such subclone, pESD76 (FIG. 18B), contained the complete coding region present in λESD-7 but without a reading frameshift.

In situ Hybridization

Antisense [35S]-UTP-labeled RNA probes were synthesized in vitro from pESD77 and used to map the distribution of transcripts corresponding to λESD-7 in the rat brain. Paraformaldehyde-fixed 30 μm thick rat brain sections were mounted on polylysine coated slides, then digested with proteinase K (10 mg/ml, 37° C., 30 min), acetylated and dehydrated in graded ethanol solutions. Approximately 5×10$^5$ cpm/ml of the RNA probe was hybridized in situ at 55° C. for 12 hrs in 50% formamide, 0.3M NaCl, 10 mM Tris (pH 8), 1 mM EDTA, 0.05% tRNA, 10% dextran sulfate, IX Denhardt's solution, and 10 mM DTT. Glass cover slips were removed from tissue sections by washing in 4x SSC for 15min at room temperature. Sections were treated with RNase A (20 μg/ml, 37° C., 30 min), washed for 30 min in 2x SSC, 1 mM DTT at room temperature and for 30 min in 0.1x SSC, 1 mM DTT at 55° C. Sections were dehydrated in graded ethanol solutions containing 1 mM DTT and exposed to Kodak XAR film at room temperature for 1–2 days. For higher resolution analysis slides were dipped in Kodak NTB-2 nuclear photographic emulsion, which was diluted 1:1 with distilled water, at 40° C. Seven to ten days after dipping, slides were developed and stained with thionin. The distribution of silver grains was analyzed with dark field illumination.

RESULTS AND DISCUSSION

Isolation and Nucleotide Sequencing of cDNA Clones

A cDNA library prepared using poly (A+) RNA isolated from rat diencephalon was screened with a radiolabeled probe made from cDNA clone λPCA48 which encodes the rat neuronal nAchR alpha3 subunit (Boulter, et al., 1986). Three groups of clones, classified according to hybridization signal intensity, were obtained. Members of one class of cDNA clones encoded the alpha4-1 and alpha4-2 subunits that are generated from the alpha4 gene by alternative mRNA splicing (Goldman, et al., 1987). The second class of cDNA clones encoded the beta2 subunit (Deneris, et al., 1988). The third class was represented by a single clone, λESD-7, which contained EcoRI insert fragments of approximately 1800, 900 and 300 base pairs.

To determine which of the three cloned EcoRI fragments were responsible for the original hybridization signal, a Southern blot was made of EcoRI digested λESD-7 DNA and probed with radiolabeled λCA48 insert DNA. The 1800 base pair EcoRI fragment hybridized and was therefore subcloned to determine a partial nucleotide sequence. The sequence data showed that the 1800 base pair fragment was different from, but had significant sequence identity with, previously isolated rat neuronal nAChR subunit cDNAs. However, alignment of the deduced amino acid sequence of this cloned fragment with other rat neuronal rAChR alpha and beta-subunits suggested that this cloned fragment did not contain the entire coding region; indeed, the deduced amino acid sequence of the extreme 5'-end of the insert DNA showed sequence homology with the neuronal nAChRs beginning at approximately amino acid residue 25.

Inspection of the nucleotide sequence revealed, in addition, a naturally occurring EcoRI site (i.e., an EcoRI site and flanking sequences which were different from the synthetic EcoRI linker used in the construction of the cDNA library) located at the 5'-terminus of the 1800 base pair cloned cDNA fragment. It seemed likely that either the 300 or 900 base pair EcoRI fragment might contain the coding region for the signal peptide, amino acids 1–25 and possibly the 5'-untranslated sequences. Nucleotide sequencing revealed that the 300 base pair EcoRI fragment had a naturally occurring EcoRI site at its 3'-terminus, an open reading frame with a deduced amino acid sequence reminiscent of a signal peptide and 25 amino acids at its 3'-terminus which showed sequence homology with rat neuronal nAChRs.

The complete nucleotide sequences of the 300 and 1800 base pair EcoRI fragments from λESD-7 were determined over both DNA strands. It appeared that the 1800 base pair fragment contained a single base pair deletion at nucleotide position 646 (FIG. 19) since beyond this point a shift in reading frame was required to maintain both an open reading frame and homology with other rat neuronal nAChR subunits. To determine whether this nucleotide was missing in other clones, additional rat diencephalon cDNA library screenings were performed using the 1800 base pair EcoRI fragment as a probe. Three additional clones were obtained, which, by restriction endonuclease mapping and partial nucleotide sequence anaylses, were found to be colinear with λESD-7 (see FIG. 18A). Nucleotide sequence data derived from λHYP504 and λHYP630 (FIG. 18A) show that in regions of overlap both of these clones have sequences identical to λESD-7 except for the presence of an additional thymidine residue at nucleotide position 646. The presence of a thymidine residue resulted in an extended open reading frame (see below). Since two out of three clones examined have an extra thymidine residue at nucleotide position 646, we conclude that the reading frameshift in λESD-7 is most likely a cloning artifact. Thus, the nucleotide sequence presented in FIGS. 19A to 19C is a composite obtained from clones λESD-7, λHYP504 and λYP630.

Primary Structure of the λESD-7 λHYP504 and λHYP630 Encoded Protein

The composite sequence presented in FIG. 19 revealed an open reading frame that begins with a methionine codon at nucleotide position −90 and terminates with a TAG stop codon at nucleotide position 1303. Thus, the encoded protein is composed of 464 amino acid residues with a calculated molecular mass of 53.3 kilodaltons. The encoded protein was found to have significant sequence similarity to members of the neurotransmitter-gated ion-channel superfamily being more related to the neuronal nAChR subunits (40–55% sequence identity) than to either muscle nAChR subunits (30–40% sequence identity) or to the GABAA (Schofield, ez al., 1987) and glycine (Grenningloh, et al., 1987) receptor subunits (approximately 20% sequence identity).

The primary structure of the encoded protein has features found-in other members of the neuronal nAChR subunit family (FIG. 20). Five hydrophobic regions were identified using the algorithm of Kyte and Doolittle (1982). The first hydrophobic region occurs in the initial thirty residues of the protein and has features of a signal peptide (Von Heijne, 1986). The remaining hydrophobic stretches are in regions that are homologous to the four putative transmembrane domains of other nAChR subunits. The encoded protein has two potential N-linked glycosylation sites, both of which are conserved in the alpha3, alpha4, and beta2 subunits. Also present are two cysteine residues that correspond to cysteines 128 and 142 in the alpha subunit of the Torpedo electric organ nAChR (Noda, et al., 1982). However, absent from the protein are two cysteine residues that correspond to cysteine 192 and 193 of the Torpedo electric organ nAChR alpha subunit (FIG. 20). In this respect the encoded protein is similar to the beta1, gamma, and delta subunits of the Torpedo and muscle nAChRs as well as the rat beta2 subunit (Deneris, et al., 1988), the chick neuronal non-alpha subunit (Nef, et al, 1988; Schoepfer, et al., 1988), and the Drosophilia ARD subunit (Hermans-Borgmeyer, 1986). In our nomenclature, a putative neuronal nAChR subunit identified by cDNA cloning is given the name "alpha" if the Torpedo alpha subunit cysteines 128, 142, 192, and 193 are conserved and "beta" if only 128 and 142 are conserved (Boulter, et al., 1986; Goldman, et al., 1987; Deneris, et al., 1988; Wada, et al., 1988; Boulter, et al., 1987). Thus, the name beta3 has been assigned to the gene and subunit defined by clones λESD-7, λYP504, and λHYP630.

The primary structure of beta3 suggests that it participates as a subunit of an nAChR. One hypothesis is that in certain neural systems the beta3 subunit contributes to the formation of an nAChR by combining with either the alpha2, alpha3, or alpha4 subunit. Another possibility is that the beta3 subunit functions with an as yet unidentified alpha-type subunit to form an nAChR subtype. A third possibility is that some brain nAChR subtypes are composed of more than two kinds of subunits as is the case for the muscle nAChRs. Thus, beta3, along with an alpha subunit and another beta subunit (e.g. beta2) may form an nAChR subtype. Since we have not yet been able to detect functional nAChRs with beta3, a forth formal possibility is that the beta3 protein is not part of an nAChR but is a subunit of another neurotransmitter-gated ion-channel.

The Beta3 Gene Is Expressed in the Brain

The clones encoding the beta3 subunit were isolated from diencephalon cDNA libraries suggesting that the corresponding gene is expressed in the brain in situ hybridization was performed using probes made from pESD77 (see Experimental Procedures, this experimental section) to confirm this idea and to determine the relationship between the expression of the beta3 gene and the expression of genes encoding neuronal nicotinic acetylcholine receptor subunits. Shown in FIG. 21 are X-ray autoradiograms of [$^{35}$S]-radiolabeled antisense RNA probe hybridization to transcripts in paraformaldehyd-fixed rat forebrain and midbrain sections. Strong hybridization was seen in neurons of the medial habenula, substantia nigra pars compacta and ventral tegmental area, the reticular nucleus of the thalamus and mesencephalic nucleus of the trigeminal. A similar hybridization pattern was seen with antisense probes derived from clone, λ51 (FIG. 18A) which encodes only 3' non-coding sequence of the beta3 transcript (data not shown). No hybridization signals above background levels were detected with sense-strand control probes (data not shown). Thus, beta3 is the fifth member of the nAChR gene family which is expressed in the brain.

In addition to the strong hybridization signals described above, a weak hybridization in the lateral habenula was also consistently seen. Higher resolution analysis (FIG. 22) revealed strong hybridization in individual neuronal cell bodies scattered throughout the lateral habenula. Preliminary evidence also indicates that the beta3 gene is expressed in additional isolated neuronal cell bodies scattered throughout the brain, most notably in the lateral hypothalamus.

The relationship between the expression of the beta3 gene and the genes encoding the other neuronal nicotinic acetylcholine receptor subunits is summarized in Table 7. In all our experiments to date, we have not been able to find a discrete forebrain or midbrain region where both beta3 and alpha2 hybridization occurs. In contrast, alpha4-2 and beta2 hybridization were found in each region in which we have reported beta3 hybridization, although very weak alpha4-2 and beta2 hybridization signals were found in the lateral habenuxla. Alpha4-1 is found in each of the reported regions except the lateral habenula. Alpha3 hybridization is also found in each of these regions except the lateral habenula and mesencephalic nucleus of the trigeminal. It remains to be determined whether the beta3 gene is expressed in the same neurons as either alpha3, alpha4, or beta2.

Conclusion

The nucleotide sequence of cDNA clones which is homologous to but different from previously described nAChR cDNAs has been presented. The protein, beta3, encoded by these cDNA clones has structural features that are found in other nAChR subunits. Our data demonstrate the beta3 gene is expressed in the brain. Thus, we propose that beta3 is a component of a neuronal nAChR subtype.

FIGURE LEGENDS

Experimental Section V

FIG. 18 (A & B). Beta3 cDNA clones. A) Relationship and partial restriction endonuclease map of λESD-7, λHYP630, λHYP504, and λ51 cDNA clones. The black bar represents the coding region and the thin horizontal lines flanking the coding region represent 5' and 3' untranslated regions of the beta3 cDNA clones. Arrows indicate the set of M13 deletion subclones used to determine the nucleotide sequence of the cDNA clones. The position of the reading frameshift in λESD-7 is indicated by an asterisk. B) Expression construct, pESD76, in plasmid vector pSP64.

FIGS. 19A to 19C. Nucleotide sequence and deduced primary structure of the beta3 protein. Nucleotides and amino-acid residues are numbered relative to the predicted mature amino terminus of the protein. The method of Von Heijne (1986) was used to predict valine at position 1 as the amino-terminus of the mature protein. Negative numbers correspond to nucleotides encoding the 5' untranslated region and amino acids of the predicted leader peptide. Asterisk indicates position of the reading frameshift in λESD-7. Underlined is a potential polyadenylation signal sequence.

FIG. 20. Amino acid sequence alignment of the beta3 subunit with neuronal nAChR subunits. Aligned with the beta3 subunit are the rat beta2, alpha2, alpha3 and alpha4-1 subunits. Indicated in the figure are the positions of the predicted leader peptide, potential N-linked glycosylation sites (double crosses), cysteine residues conserved in each member of the neurotransmitter-gated ion-channel subunit superfamily (asterisks), putative transmembrane domains (TMD I–IV) and cytoplasmic domain.

FIG. 21. Localization of beta3 transcripts in the rat forebrain and midbrain. Rat brain sections were probed with [$^{35}$S]-UTP radiolabeled antisense RNA transcribed in vitro from pE5D77 (see Experimental Procedures section of this experimental section). Regions where hybridization signals were detected are indicated. Magnification: X10.

FIG. 22. Darkfield photomicrograph of the habenular nuclei. Rat brain sections were treated as described in FIG. 21 and the Experimental Procedures section of this experimental section. Abbreviations: L, lateral habenula; M, medial habenula. Magnification: X140.

TABLE 7

Correlation of beta3 gene expression in the rat forebrain and midbrain to the expression of the alpha2, alpha3, alpha4 and beta2 genes Regions indicated are those shown in FIGS. 21 and 22 where beta3 antisense probe hybridization was detected. Alpha 4-1 and alpha4-2 are two different products of the alpha4 gene that presumably arise by alternative mRNA splicing. Abbreviations: LH, lateral habenula; MH, medial habenula; RN, reticular nucleus of the thalamus; SN, substantia nigra pars compacta; VTA, ventral tegmental area; MT, mesencephalic nucleus of the trigeminal. –, no signal detected; (+), very weak signal detected; +, weak to strong signal detected. Summary of data for alpha and beta2 gene expression obtained from Wada, et al., (1988) and Wada, et al., (1989, in press).

| Brain region | Neuronal nAchR gene | | | | |
|---|---|---|---|---|---|
| | Alpha2 | Alpha3 | Alpha4-1 | Alpha4-2 | Beta2 |
| LH | – | – | – | (+) | (+) |
| MH | – | + | + | + | + |
| RN | – | + | + | + | + |
| SN | – | + | + | + | + |
| VTA | – | + | + | + | + |
| MT | – | – | + | + | + |

EXPERIMENTAL SECTION VI

BETA4

This experimental section discloses details of another new member of the neuronal nicotinic acetylcholine receptor family, beta4.

cDNA Library Construction and Screening

A cDNA library was constructed using poly (A+) RNA isolated from the PC12 cell line and the UNI ZAP-cDNA Synthesis Kit (Stratagene Cloning Systems, Inc., La Jolla, Calif.). A library of approximately $2 \times 10^7$ elements was obtained. One million plaques were screened at high stringency using a radiolabeled exon 5 DNA probe obtained from a fragment of the beta4 genomic clone DD15 (see FIG. 23). Ten positive clones were selected and one clone, APC13, was sequenced and shown to contain the entire coding region of the beta4 gene as well as approximately 150 and 800 base pairs of 5' and 3'-untranslated regions, respectively.

Genomic Library Construction and Screening

Genomic DNA was isolated from purified neonatal rat (Sprague-Dawley) liver nuclei. The high molecular weight DNA was partially restricted with MboI, filled-in with dCTP and dATP, size-fractionated on linear NaCl gradients and ligated in the Xho half-site of the replacement vector λGEM-11 (Promega Corp., Madison, Wis.). Genomic clones harboring the alpha3 (RG518B and RG13) and alpha5 genes (RG13 and RG512) were isolated by screening approximately $1 \times 10^6$ genomic library phage with radiolabeled cDNA probes containing the entire coding region of the alpha3 (PCA48) or alpha5 (PC1321) cDNA clones, respectively. Beta4 genomic clone RG518A was isolated by performing a 'chromosome walk' 5'- to clone RG518B. Beta4 genomic clone DD15 was isolated by cross-hybridization to a radiolabeled beta2 cDNA probe.

Functional Expression in Xenopus

To test whether the protein encoded by the beta4 gene could function as part of a nicotinic acetylcholine receptor, a full-length cDNA was isolated as described above. This clone, pZPC13, was then used as template for the in vitro synthesis of capped RNA transcripts using the SP6 polymerase. This RNA was then injected into *Xenopus laevis* oocytes both alone and in various pairwise combinations with in vitro transcripts prepared from the cloned alpha2, alpha3, alpha4 and alpha5 genes. After 2–4 days in culture, electrophysiological recordings were made from the oocytes and the responses to perfused acetylcholine were monitored.

DETAILED DESCRIPTION OF THE FIGURES

FIG. 23. Partial restriction endonuclease map and orientation of transcription units for rat genomic clones encoding members of the nicotinic acetylcholine receptor-related gene family. Arrows indicate the direction of transcription for the beta4, alpha3 and alpha5 genes; the stippled boxes are approximate transcription units. The solid boxes represent exons (1–6) for the beta4 subunit gene.

FIGS. 24A to 24C. Nucleotide and derived amino acid sequences for the beta4 gene encoded by clones DD15 and RG518A. Nucleotides in the putative coding regions (exons 1–6) are in upper case letters; lower case letters correspond to putative intron sequences. The mature beta4 protein consists of 473 amino acids.

FIGS. 25A to 25C. Nucleotide and derived amino acid sequences for the cDNA clone pPC1321 encoding the rat alpha5 gene. The mature alpha5 protein consists of 424 amino acids.

FIG. 26. Comparison of the aligned amino acid sequences for the beta2, beta3 and beta4 genes. Sequences were aligned using University of Wisconsin Genetics Computer Group software. Putative functional domains such as the signal peptide and membrane spanning regions were predicted based on hydrophobicity plots using the Kyte and Doolittle algorithm. Asterisks indicate the positions of conserved cysteine residues.

FIG. 27. Comparison of the aligned amino acid sequences for the alpha2, alpha3, alpha4 and alphas genes. Sequences were aligned as in FIG. 26.

FIG. 28. Autoradiograms of Northern blot hybridization analysis of PC12 poly (A+) RNA using radiolabeled probes prepared from all identified members of the rat nicotinic acetylcholine receptor-related gene family. Agarose gel electrophoresis was carried out in the presence of formaldehyde and each lane contained identical 6 µg aliquots of PC12 poly (A+) RNA. Hybridization and washing conditions were the same for all samples. X-ray film exposure times were the same for the autoradiograms using all probes (24 hours) except alpha5 (44 hours). Longer exposure times (72 hours) for samples probed with alpha2, alpha4 and beta3 failed to reveal hybridizing RNA species. The numbers refer to approximate lengths of RNA transcripts in kilobases.

FIG. 29. In situ hybridization autoradiograms showing the distribution of alpha5 and beta4 transcripts in coronal sections of the rat brain. Photographs are from films placed over histological sections. Magnification x4.5. Abbreviations: IPN, interpeduncular nucleus; ISO, isocortex; MH, medial habenula; SNc, substantia nigra pars compacta; SUB, subiculum; VGn, trigeminal ganglion; VTA, ventral tegmental area.

TABLE 8

The percent amino acid sequence identity among pairwise combinations of members of the rat neuronal nicotinic acetylcholine receptor related gene family.

| | Alpha2 | Alpha3 | Alpha4 | Alpha5 | Beta2 | Beta3 | Beta4 |
|---|---|---|---|---|---|---|---|
| Alpha2 | 100 | 58 | 68 | 55 | 50 | 56 | 48 |
| Alpha3 | | 100 | 59 | 52 | 50 | 50 | 46 |
| Alpha4 | | | 100 | 49 | 47 | 52 | 52 |

TABLE 8-continued

The percent amino acid sequence identity among pairwise combinations of members of the rat neuronal nicotinic acetylcholine receptor related gene family.

| | Alpha2 | Alpha3 | Alpha4 | Alpha5 | Beta2 | Beta3 | Beta4 |
|---|---|---|---|---|---|---|---|
| Alpha5 | | | | 100 | 46 | 68 | 47 |
| Beta2 | | | | | 100 | 44 | 64 |
| Beta3 | | | | | | 100 | 44 |

TABLE 9

| RNA Transcripts Injected | Response to $10^{-6}$M ACh |
|---|---|
| alpha1 | no |
| beta4 | no |
| alpha1 + beta4 | no |
| alpha1 + beta4 + gamma + delta | yes |
| alpha2 + beta4 | yes |
| alpha3 + beta4 | yes |
| alpha4 + beta4 | yes |
| alpha5 + beta4 | no |

RNA transcript were synthesized in vitro and injected in the indicated combinations into *Xenopus laevis* oocytes. Electrophysiological recordings were made from individual oocytes after bath application of acetylcholine (ACh). Depolarizing responses varied from 10–40 mV; resting potentials ranged from –50 to –100 mV. Negative responses were less than 1 mV depolarization at 100 micromolar ACh. At least three oocytes were tested for each combination of injected RNA's. Alpha1, gamma and delta are mouse muscle acetylcholine receptor subunits.

REFERENCES

1. Armstrong, A., Saper, C. B., Levey, A. I., Wainer, B. H., and Terry, R. D. (1983). Distribution of cholinergic neurons in rat brain: demonstrated by the immunocytochemical localization of choline acetyltransferase. *J. Comp. Neurol.* 216, 53–68.

2. Aviv, H. and Leder, P. (1972). Purification of biologically active globin messenger RNA by chromatography on oligothymidylic acid-cellulose. *Proc. Natl. Acad. Sci., USA,* 69, 1408–1412.

3. Axelsson, J. and Thesleff, S. (1959). A study of supersensitivity in denervated mammalian skeletal muscle. *J. Physiol.* 147, 178–193.

4. Baldwin, A. S., Kittler, E. L. W. and Emerson, C. P. Jr. (1985). Structure, evolution and regulation of a fast muscle troponin I gene. *Proc. Natl. Acad. Sci., USA* 82, 8080–8084.

5. Ballivet, M., Patrick, J., Lee, J., and Helnemann, S. (1982). Translation of exogenous messenger RNA coding for nicotinic acetylcholine receptors produces functional receptors in Xenopus oocytes. *Proc. R. Soc. Lond. B.* 215, 241–246.

6. Ballivet, M., et al. In Preparation.

7. Bell, G. I., et al. (1986). *Nucleic Acid Res.* 14, 8427–8446.

8. Benton, W. and Davis, R. (1977). *Science* 196, 180–182.

9. Boulter, J., Connolly, J., Deneris, E., Goldman, D., Heinemann, S., and Patrick, J. (1987). Functional expression of two neuronal nicotinic acetylcholine receptors from cDNA clones identifies a gene family. *Proc. Natl. Acad. Sci., USA* 84, 7763–7767.

10. Boulter, J., Evans, K., Goldman, D., Martin, G., Treco, D., Heinemann, S., and Patrick, J. (1986). Isolation of a cDNA clone coding for a possible neural nicotinic acetylcholine receptor a-subunit. *Nature* 319, 368–374.

11. Boulter, J., Evans, K. L., Martin, G., Gardner, P. D., Connolly, J., Heinemann, S. and Patrick, J. (1988). Mouse muscle acetylcholine receptor: molecular cloning of α-, β-, λ- and δ-subunit cDNA's and expression in *Xenopus laevis* oocytes, (manuscript in preparation).

12. Boulter, J., Luyten, W., Evans, K., Mason, P., Ballivet, M., Goldman, D., Stengelin, S., Martin, G., Heinemann, S., and Patrick, J. (1985). Isolation of a clone coding for the a-subunit of a mouse acetylcholine receptor. *J. Neurosci.* 5, 2545–2552.

13. Brandl, C. J., and Deber, C. M. (1986). *Proc. Natl. Acad. Sci., USA* 83, 917.

14. Breathnach, R., Benoist, C., O'Hare, K., Gannon, F., Chambon, P. (1978). *Proc. Natl. Acad. Sci., USA* 75, 4853–4857.

15. Breathnach, R., and Chambon, P. (1981). Organization and expression of eucaryotic split genes coding for proteins. *Ann. Rev. Biochem.* 50, 349–383.

16. Breitbart, R. E. and Nadal-Ginard, B. (1987). *Cell* 49, 793–803.

17. Brockes, J. P. and Hall, Z. W. (1977). Synthesis of acetylcholine receptor by denervated rat diaphragm muscle. *Proc. Natl. Acad. Sci., USA* 72, 1368–1372.

18. Brown, D. A., Docherty, R. J., and Halliwell, J. V. (1984). The action of cholinomimetic substances on impulse conduction in the habenulointerpeduncular pathway of the rat in vitro. *J. Physiol.* 353, 101–109.

19. Brown, D. A. and Fumagalli, L. (1977). *Brain Res.* 129, 165–168.

20. Buonanno, A. and Merlie, J. P. (1986). Transcriptional regulation of nicotinic acetylcholine receptor genes during muscle development. *J. Biol. Chem.* 261, 11452–11455.

21. Carbonetto, S. T., Fambrough, D. M. and Moller, K. J. (1978). *Proc. Natl. Acad. Sci., USA* 72, 1016–1020.

22. Cathala, G., Savouret, J., Mendez, B., West, B., Karin, M., Martial, J., and Baxter, J. (1983). A method for isolation of intact, translationally active ribonucleic acid. *DNA* 2, 329–335.

23. Chiappinelli, V. A. and Dryer, S. E. (1984). Nicotinic transmission in sympathetic ganglia: blockade by the snake venom neurotoxin kappa-bungarotoxin. *Neurosci. Letts.* 50, 239–244.

24. Clarke P. B. S. (1988) in *Nicotine: Actions and Medical Implications.* (Stolerman I. P., Wonnacott 5., and Russel M. A. H., eds). Oxford University Press.

25. Clarke, P. B. S., Schwartz, R. D., Paul, S. M., Pert, C. B., and Pert, A. (1985). Nicotinic binding in the rat brain: Autoradiographic comparison of [³H]-acetylcholine, [3H]-nicotine, and [¹²⁵I]-a-bungarotoxin. *J. Neurosci.* 5, 1307–1315.

26. Claudio, T., Ballivet, M., Patrick, J., and Heinemann, S. (1983). Nucleotide and deduced amino acid sequences of *Torpedo californica* acetylcholine receptor g subunit. *Proc. Natl. Acad. Sci., USA* 80, 1111–1115.

27. Coleman, A. (1984) In: *Transcription and Translation: A Practical Approach.* (eds. Hames, B. D. and Higgins, J.). IRL Press, Arlington, Va., pp.49–69.

28. Conti-Tronconi, B. M., Dunn, S. M. J., Barnard, E. A., Dolly, J. O., Lai, F. A., Ray, N., and Raftery, M. A. (1985). Brain and muscle nicotinic acetylcholine receptors are different but homologous proteins. *Proc. Natl. Acad. Sci., USA* 82, 5208–5212.

29. Cox, K. H., DeLeon, D. V., Angerer, L. M., and Angerer, R. C. (1984). Detection of mRNAs in sea urchin embryos by in situ hybridization using asymmetric RNA probes. *Dev. Biol.* 101, 485–502.

30. Dale, R. M. K., McClure, B. A., and Houchins, J. P. (1985). A rapid single-stranded cloning strategy. for producing a sequential series of overlapping clones for use in DNA sequencing: Application to sequencing the corn mitochondrial 18S rDNA. *Plasmid* 13, 31–40.

31. Deneris, E. S., Boulter, J., Connolly, J., Wada, K., Patrick, J., and Heinemann, S. (1987). Abstract, Society for Neuroscience, In Press.

32. Deneris, E. S., Connolly, J., Boulter, J., Wada, E., Wada, K., Swanson, L., Patrick, J., and Heinemann, S. (1988). Primary Structure and Expression of Beta 2: A Novel Subunit of Neuronal Nicotinic Acetycholine Receptors, *Neuron*, 1:45–54 (1988).

33. Devillers-Thiery, A., Giraudat, J., Bentaboulet, M. and Changeux, J-P. (1982). *Proc. Nail. Acad. Sci., USA* 80, 2067–2071.

34. Diamond, J. and Miledi, R. (1967). A study of foetal and new-born rat muscle fibers. *J. Physiol.* 162, 393–408.

35. Dynan, W. S. and Tjian, R. (1985). Control of eukaryotic messenger RNA synthesis by sequence-specific DNA-binding proteins. *Nature* 316, 774–778.

36. Evans, S., Goldman, D., Heinemann, S., and Patrick, J. (1987). Muscle acetylcholine receptor biosynthesis: regulation by transcript availability. *J. Biol. Chem.* 262(10), 4911–4916.

37. Fenwick, E. M., Marty, A. and Neher, E. (1982). *J. Physiol.* 331, 577–597.

38. Finer-Moore, J., and Stroud, R. M. (1984). Amphipathic analysis and possible conformation of the ion channel in an acetylcholine receptor. *Proc. Nail. Acad. Sci., USA* 81, 155–159.

39. Fischbach, G. D. and Schuetze, S. M. (1980). A postnatal decrease in acetylcholine channel open time at rat endplates. *J. Physiol.* 303, 125–137.

40. Gardner, P. D., Heinemann, and Patrick, J. (1987). Transcriptional regulation of nicotinic acetycholine receptor genes: identification of control elements of a gamma subunit gene. *Molec. Brain Res.* 3, 69–76.

41. Giraudat, J., et al. (1987). *Biochemistry* 26, 2410.

42. Goldman, D., Boulter, J., Heinemann, S., and Partick, J. (1985). Muscle denervation increases the levels of two mRNAs coding for the acetylcholine receptor alpha-subunit. *J. Neurosci.* 5, 2553–2558.

43. Goldman, D., Deneris, E., Luyten, W., Kochhar, A., Patrick, J., and Heinemann, S. (1987). Members of a nicotinic acetylcholine receptor gene family are expressed in different regions of the mammalian central nervous system. *Cell* 48, 965–973.

44. Goldman, D., Simmons, D., Swanson, L. W., Patrick, J., and Heinemann, S. (1986). Mapping of brain areas expressing RNA homologous to two different acetylcholine receptor a-subunits cDNAs. *Proc. Natl. Acad. Sci., USA* 83, 4076–4080.

45. Gorman, C. M., Moffat, L. F. and Howard, B. M. (1982). Recombinant genomes which express chloramphenicol acetyltransferase in mammalian cells. *Mol. Cell. Biol.* 2, 1044–1051.

46. Graham, F. L. and van der Eb, A. J. (1973). A new technique for the assay of infectivity of human adenovirus 5 DNA. *Virology* 52, 456–467.

47. Greene, L. A. and Tischler, A. S. (1976). *Proc. Natl. Acad. Sci., USA* 73, 2424–2428.

48. Grenningloh, G., Rienitz, A., Schmitt, B., Methfessel, C., Zensen, M., Beyreuther, K., Gundelfinger, E. D., and Betz, H. (1987). The strychnine-binding subunit of the glycine receptor shows homology with nicotinic acetylcholine receptors. *Nature* 328, 215–220.

49. Grunstein, M., and Hogness, D. S. (1975). Colony hybridization: a method for the isolation of cloned DNAs that contain a specific gene. *Proc. Natl. Acad. Sci., USA* 72, 3961–3965.

50. Gubler, U., and Hoffman, B. J. (1983). A simple and very efficient method for generating a cDNA libraries. *Gene* 25, 263–269.

51. Guy, H. R. (1984). A structural model of the acetylcholine receptor channel based on partition energy and helix packing calculations. *Biophys. J.* 45, 249–261.

52. Guy, H. R., and Hucho, F. (1987). *Trends Neurosci.* 10, 318–321.

53. Hanke, W., and Breer, H. (1986). Channel properties of an insect neuronal acetylcholine receptor protein reconstituted in planar lipid bilayers. *Nature* 321, 171–174.

54. Hartzell, H. C. and Fambrough, D. M. (1972). Acetylcholine receptors: Distribution and extrajunctional density in rat diaphragm after denervation correlated with acetylcholine sensitivity. *J. Gen. Physiol.* 60, 248–262.

55. Heidmann, O., Buonanno, A., Geoffroy, B., Robert, B., Guenet, J-L., Merlie, J. P. and Changeux, J. P. (1986). Chromosomal localization of muscle nicotinic acetylcholine receptor genes in the mouse. *Science* 234, 866–868.

56. Heinemann, S., Goldman, D., Boulter, J., and Patrick, J. (1986). Molecular biology of the muscle land neural acetylcholine receptors. In *Nicotinic Acetylcholine Receptor: Structure and Function*, NATO ASI Series H, Volume 3, A. Maelicke, ed. (Berlin: Springer-Verlag), pp. 359–387.

57. Herkenham, M., and Nauta, W. J. H. (1977). Afferent connections of the habenular nuclei in the rat: A horseradish peroxidase study, with a note on the fiber of passage problem. *J. Comp. Neurol.* 173, 123–146.

58. Herkenham, M., and Nauta, W. J. H. (1979). Efferent connections of the habenular nuclei in the rat. *J. Comp. Neurol.* 187, 19–48.

59. Hermans-Borgmeyer, I., Zopf, D., Ryseck, R. P., Hovemann, B., Betz, H., and Gundelfinger, E. D. (1986). Primary structure of a developmentally regulated nicotinic acetylcholine receptor protein from Drosophila. *EMBO J.* 5, 1503–1508.

60. Higgins, L. S. and Berg, D. K. (1987). *J. Neurosci.* 7, 1792.

61. Houser, C. R., Crawford, G. D., Barber, R. P., Salvaterra, P. M., and Vaughn, J. E. (1983). Organization and morphological characteristics of cholinergic neurons: an immunocytochemical study with a monoclonal antibody to choline acetyltransferase. *Brain Res.* 266, 97–119.

62. Hucho, F., Oberthur, W., and Lottspeich, F. (1986). *FEBS Lett.* 205, 137–142.

63. Huganir, R. L., Delcour, A. H., Greengard, P., and Hess, G. P. (1986). Phosphorylation of the nicotinic acetylcholine receptor regulates its rate of desensitization. *Nature* 321, 774–776.

64. Huynn, T. V., Young, R. A., and Davis, R. W. (1985). Constructing and screening cDNA libraries in λgt10 and λgt11. In *DNA Cloning: A Practical Approach*, Volume 1, D. M. Glover, ed. (Oxford: IRL Press), pp. 49–78.

65. Ichikawa, T., and Hirata, Y. (1986). Organization of choline acetyltransferase containing structures in the forebrain of the rat. *J. Neurosci.* 6, 281–292.

66. Imoto, K., et al. (1986). *Nature* 324, 670–674.

67. Jaynes, J. B., Chamberlain, J. S., Buskin, J. N., Johnson, J. E. and Hauschka, S. D. (1986). Transcriptional regulation of the muscle creatine kinase gene and regulated expression in transfected mouse myoblasts. *Mol. Cell. Biol.* 6(8), 2855–2864.

68. Kao, P. N., Dwork, A. J., Kaldany, R. J., Silver, M. L., Wideman, J., Stein, S., and Karlin, A. (1984). Identification of two alpha-subunit half-cystines specifically labeled by an affinity reagent for the acetylcholine binding site. *J. Biol. Chem.* 259, 1162–1165.

69. Kao, P. N. and Karlin, A. (1986). Acetylcholine receptor binding site contains a disulfide crosslink between adjacent half-cystinyl residues. *J. Biol. Chem.* 261, 8085–8088.

70. Karlin, A. (1969). Chemical modification of the active site of the acetylcholine receptor. *J. Gen. Phys.* 54, 245s–264s.

71. Karlin, A., DiPaola, M., Kao, P. N., and Lobel, P. (1986). Functional sistes and transient states of the nicotinic acetylcholine receptor. In, *Proteins of Excitable Membrane* (B. Hille and D. M. Famrough, eds.), John Wiley Inc., New York.

72. Kemp, G., Bently, L., McNamee, M. G., and Morley, B. J. (1985). Purification and characterization of the α-bungarotoxin binding protein from rat brain. *Brain Res.* 347, 274–283.

73. Klarsfeld, A., Daubas, P., Bourachot, B. and Changeux, J. P. (1987). A 5'-flanking region of the chicken acetylcholine receptor α-subunit gene confers tissue specificity and developmental control of expression in transfected cells. *Mol. Cell. Biol.* 7(2), 951–955.

74. Kozak, M. (1981). *Nucleic Acids Res.* 9, 5233–5252.

75. Kozak, M. (1984). *Nucleic Acids Res.* 12, 857.

76. Kurosaki, T., Fukada, K., Konno, T., Mori, Y., Tanaka, K-i., Mishina, M., and Numa, S. (1987). *FEBS Lett.* 214, 253–258.

77. Kyte, J., and Doolittle, R. F. (1982). A simple method for displaying the hydropathic character of a protein. *J. Mol. Biol.* 157, 105–132.

78. Lamour, Y., Dutar, P., and Jobert, A. (1982). Spread of acetylcholine sensitivity in the necocortex following lesion of the nucleus basalis. *Brain Res.* 252, 377–381.

79. Leff, S. E., Rosenfeld, M. G. and Evans, R. M. (1986). Complex transcriptional units: diversity in gene expression by alternative RNA processing. *Ann. Rev. Biochem.* 55, 1091–1117.

80. Lichtensteiger, W., Hefti, F., Felix, D., Huwyler, T., Melamed, E., and Schlumpf, M. (1982). Stimulation of nigrostriatal dopamine neurons by nicotine. *Neuropharmacology* 21, 963–968.

81. Marshall, R. D. (1974). *Biochem. Soc. Symp.* 40, 17.

82. Mauron, A., Nef, P., Oneyser, C., Stalder, R., Alliod, C., and Ballivet, M. (1985). Structure of chicken genes encoding the nicotinic acetylcholine receptor subunits and their variants. Society for Neuroscience, 15th Annual Meeting, Abstract 55.10, p. 171.

83. Martin, B. R. (1986). Nicotine receptors in the central nervous system. In *The Receptors,* Volume 3, P. M. Conn, ed. (Orlando, Fla.: Academic Press), pp. 393–415.

84. Maxam, A. M. and Gilbert, W. (1977) . *Proc. Natl. Acad. Sci., USA* 74, 560 (1977)

85. McCarthy, M. P., Earnest, J. P., Young, E. F., Choe, S., and Stroud, R. M. (1986). The molecular neurobiology of the acetylcholine receptor. *Ann. Rev. Neurosci.* 9:383–413.

86. McCormick, D. A. and Prince, D. A. (1987). Acetylcholine causes rapid nicotinic excitation in the medial habenular nucleus of guinea pig, in vitro. *J. Neurosci.* 7,742–752.

87. McCutchan, J. H. and Pagano, J. S. (1968). Enhancement of the infectivity of simian virus 40 deoxyribonucleic acid with diethylaminoethyl-dextran. *J. Natl. Cancer Inst.* 41, 351–357.

88. Melton, D. A., Kreig, P. A., Rebagliati, M. R., Maniatis, T., Zinn, K., and Green, M. R. (1984). Efficient in vitro synthesis of biologically active RNA and RNA hybridization probes from plasmids containing a bacteriophage SP6 promoter. *Nucl. Acids. Res.* 12, 7035–7056.

89. Merlie, J. P., Isenberg, K. E., Russell, S. D., and Sanes, J. R. (1984). Denervation supersensitivity in skeletal muscle: analysis with a cloned cDNA probe. *J. Cell Biol.* 99, 332–335.

90. Messing, J., Gronenborn, B., Muller-Hill, B., and Hofschneider, P. H. (1977). *Proc. Natl. Acad. Sci., USA* 74, 3642–3646.

91. Michler, A. and Sakmann, B. (1980). Receptor stability and channel conversion in the subsynaptic membrane of the developing mammalian neuromuscular junction. *Dev. Biol.* 80, 1–17.

92. Minty, A. and Kedes, L. (1986). Upstream regions of the human cardiac actin gene that modulate its transcription in muscle cells: presence of an evolutionarily conserved repeated motif. *Mol. Cell Biol.* 6(6), 2125–2136.

93. Mishina, M., et al. (1984). *Nature* 307, 604.

94. Mishina, M., Takai, T., Imoto, K., Noda, M., Takahashi, T., Numa, S., Methfessel, C. and Sakmann, B. (1986). Molecular distinction between fetal and adult forms of muscle acetylcholine receptor. *Nature* 321, 406–411.

95. Mulac-Jericevic, B., and Atassi, M. Z. (1986). Segment alpha 182–198 of *Torpedo californica* acetylcholine receptor contains a second toxin-binding region and binds anti-receptor antibodies. *FEBS Lett.* 199, 68–74.

96. Nef, P., Mauron, A., Stalder, R., Alliod, C. and Ballivet M. (1984). Structure linkage and sequence of the two genes encoding the delta and gamma subunits of the nicotinic acetylcholine receptor. *Proc. Natl. Acad. Sci., USA* 81, 7975–7979.

97. Nef, P., Oneyser, C., Barkas, T., and Ballivet, M. (1986). Acetylcholine receptor related genes expressed in the nervous system. In *Nicotinic Acetylcholine Receptor: Structure and Function.* A Maelicke, ed., Springer-Verlag, pp. 417–422.

98. Nef, P., Oneyser, C., Alliod, C., Couturier, S., and Ballivet, M. (1988) *EMBO J..* 7, 595–601.

99. Neumann, D., Barchan, D., Safran, A., Gershoni, J. M., and Fuchs, S. (1986). Mapping of the α-bungarotoxin binding sitge within the alpha subunit of the acetylcholine receptor. *Proc. Natl. Acad. Sci., USA* 83, 3008–3011.

100. Noda, M., Furutani, Y., Takahashi, H., Toyosato, M., Tanabe, T., Shimizu, S., Kikyotani, S., Kayano, T., Hirose, T., Inayama, S., and Numa, S. (1983b). Cloning and sequence analysis of calf cDNA and human genomic DNA encoding alpha-subunit precursor of muscle acetylcholline receptor subunits. *Nature* 302, 818–823.

101. Noda, M., Takahashi, H., Tanabe, T., Toyosato, M., Furutani,. Y., Hirose, T., Asai, M., Inayama, S., Miyata, T., and Numa, S. (1982). Primary structure of a-subunit precursor of *Torpedo californica* acetylcholine receptor deduced from cDNA sequence. *Nature* 299, 793–797.

102. Noda, M., Takahashi, H., Tanabe, T., Toyosato, M., Kikyotani, S., Furutani, Y., Hirose, T., Takashima, H., Inyama, S., Miyata, T. and Numa, S. (1983a). *Nature* 302, 528–532.

103. Oswald, R. E., and Freeman, J. A. (1980). Alpha-bungarotoxin binding and central nervous system nicotinic acetylcholine receptors. *Neuroscience* 6, 1–14.

104. Padgett, R. A., Grabowski, P. J., Konarska, M. M., Seiler, S. and Sharp, P. A. (1986). Splicing of messenger RNA precursors. *Ann. Rev. Biochem.* 55, 1119–1150.

105. Patrick, J., Ballivet, M., Boas, L., Claudio, T., Forrest, J., Ingraham, H., Mason, P., Stengelin, S., Ueno, S., and Heinemann, S. (1983). Molecular cloning of the acetylcholine receptor. *Cold Spring Harbor Symposia on Quantitative Biology*, Vo. XLVIII. Pages 71–79.

106. Patrick, J., and Stallcup, W. (1977a). Immunological distinction between acetylcholine receptor and the α-bungarotoxin-binding component on sympatahetic neurons. *Proc. Natl. Acad. Sci., USA* 74, 4689–4692.

107. Patrick, J. and Stallcup, W. B. (1977b). α-Bungarotoxin binding and cholinergic receptor function on a rat sympathetic nerve line. *J. Biol. Chem.* 252, 8629–8633.

108. Pearson, R. C. A., Galter, K. C., and Powell, T. P. S. (1983). The cortical relationships of certain basal ganglia and the cholinergic basal forebrain nuclei. *Brain Res.* 261, 327–330.

109. Perlman, D., and Halvorson, H. W. (1983). A putative signal peptidase recognition site and sequence in eukaryotic and prokaryotic signal peptides. *J. Mol. Biol.* 167, 391–409.

110. Popot, J. L., Changeux, J. P. (1984) *Physiological Revs.* 64, 1162–239.

111. Rang, H. P. (1981). *J. Physiol.* 311, 23–55.

112. Ravdin, P. M. and Berg, D. K. (1979). Inhibition of neuronal acetylcholine sensitivity by a-toxins from *Bungarus multicinctus* venom. *Proc. Natl. Acad. Sci., USA* 76, 2072–2076.

113. Rigby, P. W. J., Diekmann, M., Rhodes, C. and Berg, P. (1977). Labelling deoxyribonucleic acid to high specific activity in vivo by nick translation with DNA polymerase I. *J. Mol. Biol.* 113, 237–251.

114. Rimm, D. L., Horness, D., Kucera, J. and Blattner, F. R. (1980). Construction of coliphage λ Charon vectors with BamHI cloning sites. *Gene* 12, 301–309.

115. Rotter, A., and Jacobowitz, D. M. (1981). Neurochemical identification of cholinergic forebrain projection sites of the nucleus tegnentalis dorsalis lateralis. *Brain Res. Bull.* 6, 525–529.

116. Safran, A., Neumann, D., and Fuchs, S. (1986). Analysis of acetylcholine receptor phosphorylation sites using antibodies to synthetic peptides and monoclonal antibodies. *EMBO J.* 5, 3175–3178.

117. Sakmann, B. and Brenner, H. R. (1978). Change in synaptic channel gating during neuromuscular development. *Nature* 276, 401–402.

118. Sakurai, Y., Takano, Y., Kohjimoto, Y., Honda, K., and Kamiya, H. O. (1982). Enhancement of [$^3$H]dopamine release and its [$^3$H]metabolites in rat striatum by nicotinic drugs. *Brain Res.* 242, 99–106.

119. Sanger, F., Nicklen, S., and Coulson, A. R. (1977). DNA sequencing with chain-terminating inhibitors. *Proc. Natl. Acad. Sci., USA* 74, 5463–5467.

120. Sasavage, N. L., Smith, M., Gillam, S., Woychick, R. P., and Rottman, F. M. (1982). Variation in the polyadenylation site of bovine prolactin MRNA. *Proc. Natl. Acad. Sci., USA* 79, 223–227.

121. Schiffer, M., and Edmundson, A. B. (1967). Use of helical wheels to represent the structures of proteins and to identify segments with helical potential. *Biophys. J.* 7, 121–135.

122. Schofield, P. R., Darlison, M. G., Fujita, N., Burt, D. R., Stephenson, F. A., Rodriguez, H., Rhee, L. M., Ramachandran, J., Reale, V., Glencorse, T. A., Seeburg, P. H., and Barnard, E. A. (1987). Sequence and functional expression of the $GABA_A$ receptor shows a ligand-gated receptor superfamily. *Nature* 328, 221–227.

123. Schubert, D., Harris, A. J., Devine, C. and Heinemann, S. (1974). Characterization of a unique muscle cell line. *J.Cell Biol.* 61, 398–413.

124. Schuetze, S. M. and Role, L. W. (1987). Developmental regulation of nicotinic acetylcholine receptors. *Ann. Rev. Neurosci.* 10, 403–457.

125. Sebbane, R., Clokey, G., Merlie, J. P., Tzartos, S. and Lindstrom, J. (1983). Characterization of the mRNA for mouse muscle acetylcholine receptor α-subunit by quantitative translation in vitro. *J. Biol. Chem.* 258, 3294–3303.

126. Shibahara, S., Kubo, T., Perski, H. J., Takahashi, H., Noda, M. and Numa, S. (1985). Cloning and sequencing analysis of human genomic DNA encoding gamma subunit precursor of muscle acetylcholine receptor. *Eur. J. Biochem.* 146, 349–359.

127. Sierra, F., Pittet, A.-C., Schibler, U. (1986). *Mol. Cell. Biol.* 6, 4067.

128. Smith, M. A., Stollberg, J., Lindstrom, J. M., and Berg, D. K. (1985). Characterization of a component in chick ciliary ganglia that cross-reacts with monoclonal antibodies to muscle and electric organ acetylcholine receptor. *J. Neurosci.* 5, 2726–2731.

129. Southern, E. M. (1975). Detection of specific sequences among DNA fragments separated by gel electrophoresis. *J. Mol. Biol.* 98, 503–517.

130. Stroud, R. M. and Finer-Moore, J. (1985). Acetylcholine receptor structure, function, and evolution. *Ann. Rev. Cell Biol.* 1, 317–351.

131. Sugiyama, H., and Yamashita, Y. (1986). Characterization of putative nicotinic acetylcholine receptors solubilized from rat brains. *Brain Res.* 373, 22–26.

132. Swanson, L. W., Lindstrom, J., Tzartos, S., Schmued, L. C., O'Leary, D. M., and Cowan, W. M. (1983). Immunohistochemical localization of monoclonal antibodies to the nicotinic acetylcholine receptor in chick midbrain. *Proc. Natl. Acad. Sci., USA* 80, 4532–4536.

133. Schoepfer, R., Whiting, P., Esch, F., Blacher, R., Shimasaki, S., and Lindstrom, I. (1988) *Neuron* 1, 241–248.

134. Swanson, L. W., Sawchenko, P. E., Rivier, J., and Vale, W. W. (1983a). *Neuroendochrinology* 36, 165–186.

135. Swanson, L. W., Simmons, D., Whiting, P. J., and Lindstrom, J. (1987). Immunohistochemical localization of neuronal nicotinic receptors in the rodent central nervous system. *J. Neurosci.* 7, 3334–3342.

136. Takai, T., Noda, M., Mishina, M., Shimizu, S., Furutani, Y., Kayano, T., Ikeda, T., Kubo, T., Takahashi, H., Takahashi, T., Kuno, M. and Numa, S. (1985). Cloning, sequencing and expression of cDNA for a novel subunit of acetylcholine receptor from calf muscle. *Nature* 315, 761–764.

137. Vicini, S. and Schuetze, S. M. (1985). Gating properties of acetylcholine receptors at developing rat endplates. *J. Neurosci.* 5, 2212–2224.

138. Viera, J., and Messing, J. (1982). *Gene* 19, 259–268.

139. Von Heijne, G. (1983). Patterns of amino acids near signal-sequence cleavage sites. *Eur. J. Biochem.* 133, 17–21.

140. Von Heijne, G. (1986). A new method for predicting signal sequence cleavage sites. *Nucl. Acids Res.* 14, 4683–4691.

141. Wada, K., Ballivet, M., Boulter, J., Connolly, J., Wada, E., Deneris, E. S., Swanson, L. W., Heinemann, S., and Patrick, J. (1988). Isolation and functional expression of a gene and cDNA encoding the alpha2 subunit of a rat neuronal nicotinic acetylcholine receptor. *Science* 240, 330–334.

142. Wada, E., Wada, K., 8oulter, I., Deneris, E., Heinemann, S., Patrick, I., and Swanson, L. W. (1989) *I. Neurol. Comp.,* in press.

143. Weiher, H., Konig, M. and Gruss, P. (1983). Multiple point mutations affecting the Simian Virus 40 enhancer. *Science* 219, 626–631.

144. Weill, C. L., McNamee, M. G., and Karlin, A. (1974). Affinity-labeling of purified acetylcholine receptor from *Torpedo californica. Biochem. Biophys. Res. Commun.* 61, 997–1003.

145. Whiting, P., Esch, F., Shimasaki, S., and Lindstrom, J. (1987). Neuronal nicotinic acetylcholine receptor b-subunit is coded for by the cDNA clone $a_4$. *FEBS Lett.* 219, 459–463.

146. Whiting, P., and Lindstrom, J. (1986a). Purification and characterization of a nicotinic acetylcholine receptor from chick brain. *Biochemistry* 25, 2082–2093.

147. Whiting, P., and Lindstrom, J. (1986b). Pharmacological properties of immuno-isolated neuronal nicotinic receptors. *J. Neurosci.* 6, 3061–3069.

148. Whiting, P., and Lindstrom, J. (1987a). Purification and characterization of a nicotinic acetylcholine receptor from rat brain. *Proc. Natl. Acad. Sci., USA* 84, 595–599.

149. Whiting, P., and Lindstrom, J. (1987b). Affinity labelling of neuronal acetylcholine receptors localizes acetylcholine-binding sites to their b-subunits. *FEBS Lett.* 213, 55–60.

150. Whiting, P., Schoepfer, R., Swanson, L. W., Simmons, D., Lindstrom, J. M. (1987). *Nature* 327, 515.

151. Wilbur, W. J., and Lipman, D. J. (1983). Rapid similarity searches of nucleic acid and protein data banks. *Proc. Natl. Acad. Sci., USA* 80, 726–730.

152. Wilson, P. T., Lentz, T. L., and Hawrot, E. (1985). Determination of the primary amino acid sequence specifying the alpha-subunit of the acetylcholine receptor for *Torpedo californica. Proc. Natl. Acad. Sci., USA* 82, 8790–8794.

153. Wonnacott, S. (1986). α-Bungarotoxin binds to low-affinity nicotine binding sites in rat brain. *J. Neurochem.* 47, 1706–1712.

154. Yaffe, E. and Saxel, O., (1977). Serial passaging and differentiation of myogenic cells isolated from dystrophic mouse muscle. *Nature* 270, 725–727.

SPECIFICATION SUMMARY

From the foregoing description, one of ordinary skill in the art can understand that the present invention is the discovery and isolation of DNA segments encoding a family of new mammalian neuronal nicotinic acetylcholine receptors that are expressed in the brain and nerve cells. The new mammalian neuronal nicotinic acetylcholine receptors include individual alpha2, alpha3, alpha4.1, alpha4.2, alpha5, beta2, beta3 and beta4 receptor subunits, plus functional subunit combinations including but not limited to alpha2+beta2,alpha3+beta2, alpha4+beta2, alpha2+beta4, alpha3+beta4, and alpha4+beta4 subunits.

Both the receptor subunit genes and proteins of the present invention can be used for drug design and screening. For example, the cDNA clones encoding the alpha2, alpha3, alpha4, alpha5, beta2, beta3 and beta4 receptor subunits can be transcribed in vitro to produce mRNA. This mRNA, either from a single subunit clone or from a combination of clones, can then be injected into oocytes where it will direct the synthesis of the receptor molecule(s). Alternatively, the clones may be placed downstream appropriate gene regulatory elements and inserted into the genome of eukaryotic cells. This will result in transformed cell lines expressing one specific receptor subtype, or combinations of subtypes. The derived cell lines can then be produced in quantity for reproducible quantitative analysis of the effects of drugs on receptor function.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A substantially pure double-stranded DNA wherein the sense strand encodes the primary amino acid sequence of an alpha5 neuronal nicotinic acetylcholine receoptor polypeptide as set forth in FIGS 25A to 25C.

2. A substantially pure double-stranded DNA of claim 1 wherein said alpha subunit is encoded by DNA sequence PC1321, ATCC No. (67652).

3. Cells transformed by the substantially pure DNA of claim 1.

4. A vector containing the nucleic acid of claim 1.

5. The vector of claim 4, which is PC 1321 (ATTC No. 67625).

6. Substantially pure nucleic acid comprising the DNA sequence as set forth in FIGS. 25A to 25C or a nucleic acid complementary thereto.

7. A RNA complementary to the nucleic acid of claim 6.

8. Substantially pure nucleic acid comprising DNA sequences that are functionally equivalent to the DNA sequence PC1321, ATTC No. 67652.

9. Substantially pure nucleic acid comprising DNA sequences that are functionally equivalent to the DNA sequence set forth in FIGS. 25A to 25C.

10. mRNA transcribed from the nucleic acid set forth in FIGS. 25A to 25C.

11. Isolated nucleic acid that hybridizes under stringent conditions to nucleic acid sequences encoding polypeptide set forth in FIGS. 25A to 25C or complements thereof.

12. A method for screening drug substances to determine those drug substances which function as agonists for nicotinic acetylcholine receptors, and method comprising:

contacting a receptor with a drug substance wherein said receptor is comprised of a substantially pure neuronal nicotinic acetylcholine receptor comprising at least one alpha receptor subunit and at least one beta subunit, wherein said alpha receptor subunit is alpha5, and said beta subunit(s) is selected from the group consisting of beta2, beta3 and beta4 and measuring the response of said receptor to said drug substance.

13. A method according to claim 12 wherein the response measured is an electrophysiological response.

14. A method according to claim 13 wherein said electrophysiological response is measured by the voltage clamp technique.

15. A method according to claim 12 wherein said receptor subunits are expressed in oocytes.

16. A method for screening drug substances to determine those drug substances which function as antagonists for nicotinic acetylcholine receptors, said method comprising:

contacting a receptor comprised of a substantially pure neuronal nicotinic acetylcholine receptor comprising at least one alpha receptor subunit and at least one beta subunit, wherein said alpha receptor subunit is alpha5 and said beta subunit(s) is selected from the group consisting of beta2, beta3 and beta4, with:
a fixed concentration of an agonist for a neuronal nicotinic acetylcholine receptor, and increasing concentrations of said drug substance, and measuring the change in response of said receptor in the presence of said drug substance.

17. A method according to claim 16 wherein the response measured is an electrophysiological response.

18. A method according to claim 17 wherein said electrophysiological response is measured by the voltage clamp technique.

19. A method according to claim 16 wherein said receptor subunits are expressed in oocytes.

20. A method to identify drug substances which are capable of binding to nicotinic acetylcholine receptors, said method comprising carrying out a competitive binding assay wherein said drug substance is contacted with neuronal nicotinic acetylcholine receptor subunit alpha5 in the presence of at least one agonist for neuronal nicotinic acetylcholine receptors, and determining whether or not said drug substance affects the ability of said agonist to bind to said receptor subunit.

21. A method according to claim 20 wherein said agonist is nicotine.

* * * * *